US006818752B2

(12) United States Patent
Rozzell, Jr. et al.

(10) Patent No.: US 6,818,752 B2
(45) Date of Patent: Nov. 16, 2004

(54) SYNTHETIC GENES FOR ENHANCED EXPRESSION

(75) Inventors: J. David Rozzell, Jr., Burbank, CA (US); Peter Bui, El Monte, CA (US); Ling Hua, Arcadia, CA (US)

(73) Assignee: BioCatalytics, Inc., Pasadena, CA (US)

( * ) Notice: Subject to any disclaimer, the term of this patent is extended or adjusted under 35 U.S.C. 154(b) by 115 days.

(21) Appl. No.: 09/734,237

(22) Filed: Dec. 8, 2000

(65) Prior Publication Data

US 2003/0064432 A1 Apr. 3, 2003

Related U.S. Application Data

(63) Continuation-in-part of application No. 09/494,921, filed on Jan. 31, 2000, now Pat. No. 6,366,860.

(51) Int. Cl.[7] .......................... C07H 21/04; C12P 19/34; C12N 9/00
(52) U.S. Cl. ...................... 536/23.1; 435/91.1; 435/183
(58) Field of Search ................................ 435/91.1, 183, 435/6, 91.2; 536/23.1, 24.3; 530/300

(56) References Cited

U.S. PATENT DOCUMENTS

| | | | |
|---|---|---|---|
| 5,861,154 A | | 1/1999 | Soda et al. |
| 5,863,788 A | | 1/1999 | Soda et al. |
| 5,891,704 A | | 4/1999 | Yuying |
| 6,498,026 B2 | * | 12/2002 | Delagrave et al. .......... 435/190 |
| 2001/0051369 A1 | * | 12/2001 | Delagrave et al. .......... 435/190 |

OTHER PUBLICATIONS

SantaLucia, "A unified view of polymer, dumbell, and oligonucleotide DNA nearest–neighbor thermodynamics," PNAS, 1998, vo 95, pp. 1460–1465.*
Wen, et al.; "Rat ornithine decarboxylase gene nucleotide sequence potential regulatory elements and comparison to the mouse gene"; Database Biosis on STN, AN 1989:334579; Journal of Biological Chemistry; 1989, vol. 264, No. 15, pp. 9016–9021. (Abstract).
Ayte, et al.; "Structural characterization of the 3' noncoding region of the gene encoding rat mitochondria 3–hydroxy–3–methylglutaryl–coenzyme A synthase"; Gene. 1993, vol. 123, No. 2, pp. 267–270. (Abstract).
Hickok, et al.; "Human ornithine decarboxylase–encoding loci nucleotide sequence of the expressed gene and characterization of a pseudogene"; Gene (AMST); 1990; vol. 93, No. 2, pp. 257–264. (Abstract).

Wahlfors et al.; "Human Spermidine synthase cloning and primary structure"; Database Biosis on STN, AN 1990:448407; DNA Cell Biology; 1990, vol. 9, No. 2, pp. 103–110. (Abstract).
Yao, et al.; "Bovine ornithine decarboxylase gene: cloning, structure and polymorphisms"; DNA Sequence; Database Medline on STN, AN 1999450166; Mar. 1998; vol. 8, No. 4, pp. 203–213. (Abstract).
Zahn, K., Overexpression of an mRNA Dependent on Rare Codons Inhibits Protein Synthesis and Cell Growth, *Journal of Bacteriology*, May 1996, p 2926–2933.
Kita et al., "Cloning of the Aldehye Reductase Gene from a Red Yeast, *Sporobolomyces salmonicolor*, and Characterization of the Gene and Its Product," *Applied and Environmental Microbiology*, vol. 62, No. 7 (Jul. 1996) pp. 2303–2310.
Kita et al., "Cloning, Overexpression, and Mutagenesis of the *Sporobolomyces salmonicolor* AKU4429 Gene Encoding a New Aldehyde Reductase, Which Catalyzes the Stereoselective Reduction of Ethyl 4–Chloro–3–Oxobutanoate to Ethyl (*S*)–4–Chloro–3–Hydroxybutanoate," *Applied and Environmental Microbiology*, vol. 65, No. 12 (Dec. 1999) pp. 5207–5211.
Moore et al., "Cloning and expression of pig kidney dopa decarboxylase: comparison of the naturally occurring and recombinant enzymes," *Biochem. J.*, vol. 315 (1996) pp. 249–256.
Kane, J. F., Effects of Rare Codon Clusters on High–Level Expression of Heterologous Proteins in *Escherichia coli*, Current Opinion in Biotechnology Ltd ISSN, vol. 6 p 494–500.
Nakayama, T. et al., Purification of Bacterial L–Methionine γ–Lyase, Analytical Biochemistry, vol. 138, p 421–424.

* cited by examiner

*Primary Examiner*—Kenneth R. Horlick
*Assistant Examiner*—Young J. Kim
(74) *Attorney, Agent, or Firm*—Christie, Parker & Hale, LLP

(57) ABSTRACT

A synthetic nucleic acid sequence is disclosed, comprising a non-naturally occurring polymer of nucleic acids, having a biological function encoded by the sequence and known from a starting nucleic acid sequence, and having a difference in sequence of at least about 5% between the nucleic acids of the synthetic sequence and the starting sequence. The difference between the nucleic acid sequences results in a different free energy of folding for the synthetic sequence as compared to the starting sequence, such that the synthetic sequence would be expressed better in a selected heterologous host cell than the starting sequence would be if expressed in the same heterologous host cell.

1 Claim, 10 Drawing Sheets

Figure 1A – SEQ ID No. 3, with residual bases from restriction sites included.

```
c atg GGT cac ggc tcc aac aaA ctG ccG ggC ttt gcT acc cgC
gcT atC cac caC ggT taT gac ccG cag gaT cac ggT ggT gca ctg
gtT ccG ccg gtT tac cag acT gcT acT ttc acc ttc ccG acc gtT
gaa tac ggc gct gcg tgc ttt gcT ggc gaA cag gcT ggT cac ttc
tac TCC cgT atc tcc aac ccG acc ctG aac ctg ctg gaa gca cgT
atg gcA tcT ctg gaa ggc ggc gaA gcT ggT ctg gcg ctg gcA tcT
ggT atg ggC gcg atc acC tcT acC ctG tgg acC ctg ctg cgT ccG
ggt gac gaA gtT ctg ctg ggc aac acc ctg taT ggT tgT acT ttt
gcT ttc ctg cac cac ggT atc ggT gaA ttc ggC gtT aaA ctg ccT
caC gtA gaT atg gct gac ctg cag gca ctg gaA gcg gcT atg acC
ccg gcT acc cgT gtT atc taC ttc gaA tcC ccg gcT aac ccg aac
atg cac atg gcT gaC atc gcA ggT gtT gcT aaA atC gcT cgT atg
cac ggc gcT acc gtA gtT gtT gaT aac acc tac tgT acT ccg tac
ctg caA cgT ccG ctg gaA ctg ggc gcT gac ctg gtT gtT cac tcC
gcT acT aaA tac ctg TCC ggc caC ggc gac atc act gct ggc a.C
gtA gtA ggc TCC cag gca ctg gtT gac cgt atC cgt ctg caA ggT
ctG aaA gac atg acc ggc gcT gtT ctG tcC ccG caC gac gcA gca
ctg Ctg atg cgT ggT atc aag acc ctG aac ctg cgT atg gac cgT
cac tgT gcT aac gct cag gtA ctg gcT gaA ttc ctG gcT cgT cag
ccg cag gtA gaA ctg atc caC taT ccg ggc ctg gcT TCC ttc ccg
cag tac acT ctg gcA cgT cag cag atg TCC cag ccg ggc ggT atg
atc gcT ttc gaa ctG aag ggT ggc atc ggC gcT ggT cgT cgT ttc
atg aac gcT ctg caG ctg ttc TCC cgT gcg gtT TCC ctg ggT gaC
gcT gaA tcC ctg gcg cag cac ccg gca TCC atg act caC tcc TCC
taC acT ccG gaA gaA cgt gcg caC tac ggc atc tcc gaA ggC ctg
gtT cgT Ctg tcT gtT ggT ctg gaa gac atc gaT gaT ctg ctg gcA
gaC gtT caG cag gcT ctG aag gcT agC gcT tga GGA TCC
```

Figure 1B – SEQ ID No. 4, with residual bases from restriction sites included.

```
c atg GGT cac ggc tcc aac aaA ctG ccG ggC ttt gcT acc cgC
gcT atC cac caC ggT taT gac ccG cag gaT cac ggT ggT gca ctg
gtT ccG ccg gtT tac cag acT gcT acT ttc acc ttc ccG acc gtT
gaa tac ggc gct gcg tgc ttt gcT ggc gaA cag gcT ggT cac ttc
tac TCC cgT atc tcc aac ccG acc ctG aac ctg ctg gaa gca cgT
atg gcA tcT ctg gaa ggc ggc gaA gcT ggT ctg gcg ctg gcA tcT
ggT atg ggC gcg atc acC tcT acC ctG tgg acC ctg ctg cgT ccG
ggt gac gaA gtT ctg ctg ggc aac acc ctg taT ggT tgT acT ttt
gcT ttc ctg cac cac ggT atc ggT gaA ttc ggC gtT aaA ctg cgT
caC gtA gaT atg gct gac ctg cag
```

Figure 1C – SEQ ID No. 6, with residual bases from restriction sites included.

```
ctg cag gca ctg gaA gcg gcT atg acC ccg gcT acc cgT gtT atc
tac ttc gaA tcC ccg gcT aac ccG aac atg cac atg gcT gaC atc
gcA ggT gtT gcT aaA atC gcT cgT aag cac ggc gcT acc gtA gtT
gtT gaT aac acc tac tgT acT ccg tac ctg caA cgT ccG ctg gaA
ctg ggc gcT gac ctg gtT gtT caC tcC gcT acT aaA tac ctg TCC
ggc caC ggc gac atc act gct ggc atC gtA gtA ggc TCC cag gca
ctg gtT gac cgt atC cgt ctg caA ggT ctG aaA gac atg acc ggc
gcT gtT ctG tcC ccG caC gac gcA gca ctg Ctg atg cgT ggT acc
aag acc ctG aac ctg cgT atg gac cgT cac tgT gcT aac gct cag
gtA ctg gcT gaA ttc
```

Figure 1D – SEQ ID No. 8, with residual bases from restriction sites included.

```
gaA ttc ctG gcT cgT cag ccg cag gtA gaA ctg atc caC taT ccg
ggc ctg gcT TCC ttc ccg cag tac acT ctg gcA cgT cag cag atg
TCC cag ccg ggc ggT atg atc gcT ttc gaa ctG aag ggT ggc atc
ggC gcT ggT cgT cgT ttc atg aac gcT ctg caG ctg ttc TCC cgT
gcg gtT TCC ctg ggT gaC gcT gaA tcC ctg gcg cag cac ccg gca
TCC atg act caC tcc TCC taC acT ccG gaA gaA cgt gcg caC tac
ggc atc tcc gaA ggC ctg gtT cgT Ctg tcT gtT ggT ctg gaa gac
atc gaT gaT ctg ctg gcA gac gtT caG cag gcT ctG aag gcT agC
gcT tga GGA TCC
```

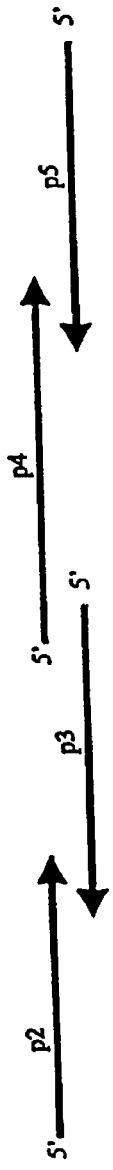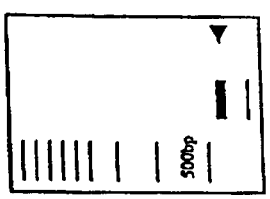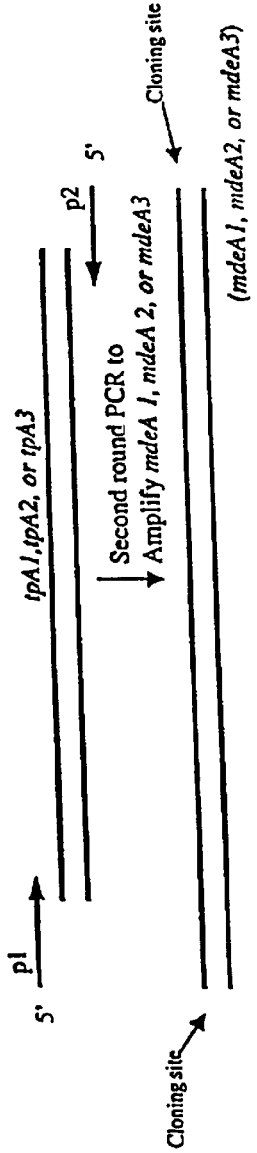
Figure 2A
Figure 2B
P1 = mdePr1-1, mdePr2-1, or mdePr3-1
P2 = mdePr1-2, mdePr2-2, or mdePr3-2
P3 = mdePr1-3, mdePr2-3, or mdePr3-3
P4 = mdePr1-4, mdePr2-4, or mdePr3-4
P5 = mdePr1-5, mdePr2-5, or mdePr3-5
P6 = mdePr1-6, mdePr2-6, or mdePr3-6

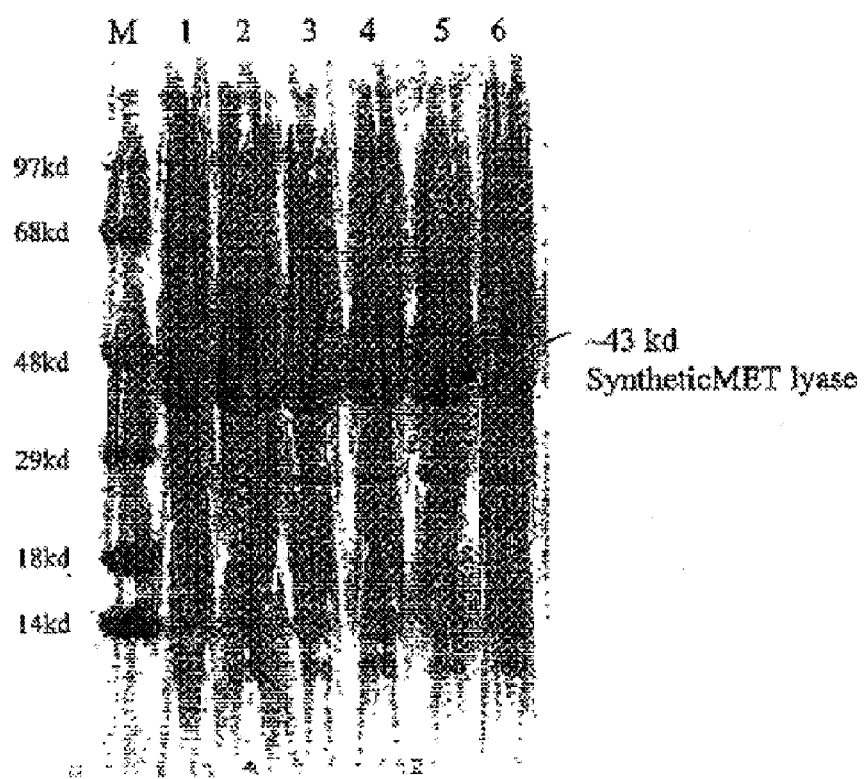
Figure 4A: THE INDUCTION OF THE SYNTHETIC *P. putida* METHIONINE-GAMMA-LYASE BL21/pTM

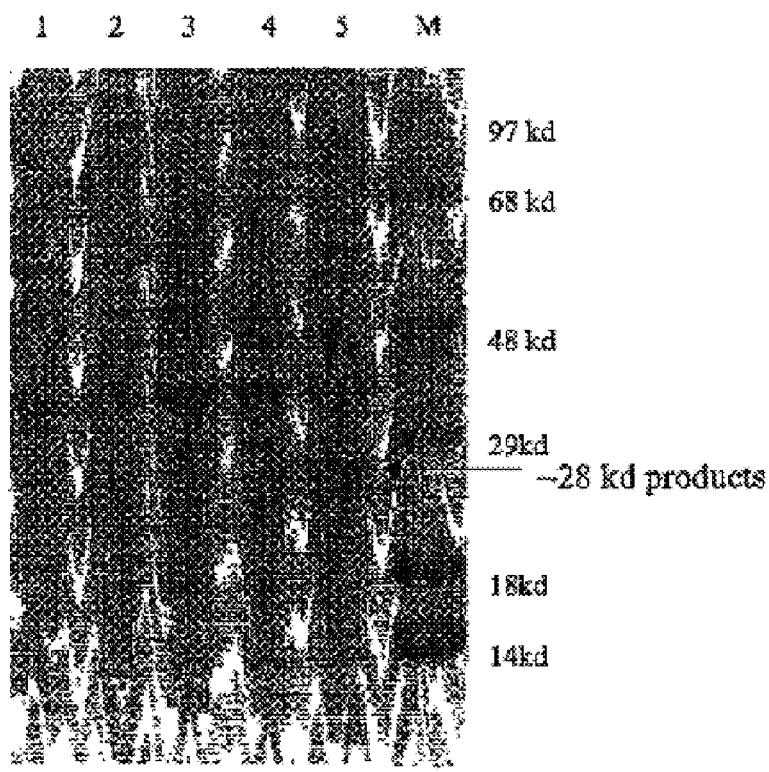
Figure 4B: The induction of native *P. putida* Methionine lyase (pSIT-mdcA)

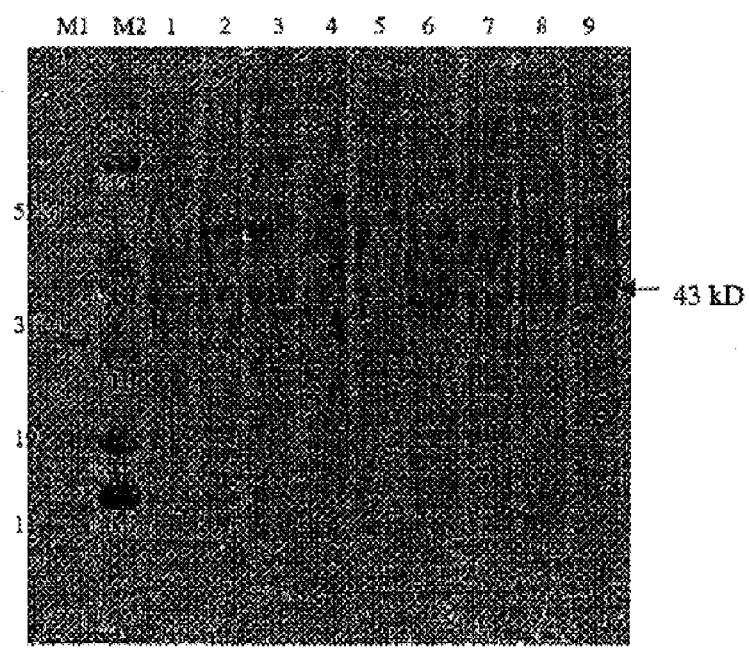
Figure 5: The Induction of the *P. putida* Naphthalene Dioxygenase and the *T. vaginalis* methionine -gamma- lyase (*mgl I*)

SEQUENCE LISTING

```
<160> NUMBER OF SEQ ID NOS: 79

<210> SEQ ID NO 1
<211> LENGTH: 1197
<212> TYPE: DNA
<213> ORGANISM: Pseudomonas putida

<400> SEQUENCE: 1
atgcacggct ccaacaagct cccaggattt gccacccgcg ccattcacca tggctacgac      60
ccccaggacc acggcggcgc actggtgcca ccggtctacc agaccgcgac gttcaccttc     120
cccaccgtgg aatacggcgc tgcgtgcttt gccggcgagc aggccgggca tttctacagc     180
cgcatctcca accccaccct caacctgctg aagcacgca tggcctcgct ggaaggcggc      240 gaggccggc tggcgctggc ctcgggcatg ggggcgatca cgtccacgct atggacactg      300
ctgcgccccg gtgacgaggt gctgctgggc aacaccctgt acggctgcac ctttgccttc     360
ctgcaccacg gcatcggcga gttcggggtc aagctgcgcc atgtggacat ggccgacctg     420
caggcactgg aggcggccat gacgccggcc acccgggtga tctatttcga gtcgccggcc     480
aaccccaaca tgcacatggc cgatatcgcc ggcgtggcga agattgcacg caagcacggc     540
gcgaccgtgg tggtcgacaa cacctactgc acgccgtacc tgcaacggcc actggagctg     600
ggcgccgacc tggtggtgca ttcggccacc aagtacctga gcggccatgg cgacatcact     660
gctggcattg tggtgggcag ccaggcactg gtggaccgta tacgtctgca gggcctcaag     720
gacatgaccg gtgcggtgct ctcgccccat gacgccgcac tgttgatgcg cggcatcaag     780
accctcaacc tgcgcatgga ccgccactgc gccaacgctc aggtgctggc cgagttcctc     840
gcccggcagc cgcaggtgga gctgatccat tacccggcc tggcgagctt cccgcagtac     900
accctggccc gccagcagat gagccagccg ggcggcatga tcgccttcga actcaagggc     960
ggcatcggtc ccgggcggcg gttcatgaac gccctgcaac tgttcagccg cgcggtgagc    1020
ctgggcgatg ccgagtcgct ggcgcagcac ccggcaagca tgactcattc cagctatacc    1080
ccagaggagc gtgcgcatta cggcatctcc gagggctgg tgcggttgtc ggtggggctg    1140
gaagacatcg acgacctgct ggccgatgtg caacaggcac tcaaggcgag tgcctga      1197

<210> SEQ ID NO 2
<211> LENGTH: 399
<212> TYPE: PRT
<213> ORGANISM: Artificial Sequence
<220> FEATURE:
<223> OTHER INFORMATION: Pseudomonas putida methionine gamma-lyase amino
      acid sequence, with a non-naturally occurring glycine residue
      inserted at position 2

<400> SEQUENCE: 2

Met Gly His Gly Ser Asn Lys Leu Pro Gly Phe Ala Thr Arg Ala Ile
1               5                   10                  15

His His Gly Tyr Asp Pro Gln Asp His Gly Gly Ala Leu Val Pro Pro
                20                  25                  30

Val Tyr Gln Thr Ala Thr Phe Thr Phe Pro Thr Val Glu Tyr Gly Ala
            35                  40                  45
```

```
Ala Cys Phe Ala Gly Glu Gln Ala Gly His Pro Tyr Ser Arg Ile Ser
     50                  55                  60

Asn Pro Thr Leu Asn Leu Leu Gln Ala Arg Met Ala Ser Leu Glu Gly
 65                  70                  75                  80

Gly Glu Ala Gly Leu Ala Leu Ala Ser Gly Met Gly Ala Ile Thr Ser
                 85                  90                  95

Thr Leu Tyr Thr Leu Leu Arg Pro Gly Asp Glu Val Leu Leu Gly Asn
            100                 105                 110

Thr Leu Tyr Gly Cys Thr Phe Ala Phe Leu His His Gly Ile Gly Glu
            115                 120                 125

Phe Gly Val Lys Leu Arg His Val Asp Met Ala Asp Leu Gln Ala Leu
        130                 135                 140

Glu Ala Ala Met Thr Pro Ala Thr Arg Val Ile Tyr Phe Glu Ser Pro
145                 150                 155                 160

Ala Asn Pro Asn Met His Met Ala Asp Ile Ala Gly Val Ala Lys Ile
                165                 170                 175

Ala Arg Lys His Gly Ala Thr Val Val Val Asp Asn Thr Tyr Cys Thr
            180                 185                 190

Pro Tyr Leu Gln Arg Pro Leu Gln Leu Gly Ala Asp Leu Val Val His
            195                 200                 205

Ser Ala Thr Lys Tyr Leu Ser Gly His Gly Asp Ile Thr Ala Gly Ile
210                 215                 220

Val Val Gly Ser Gln Ala Leu Val Asp Arg Ile Arg Leu Gln Gly Leu
225                 230                 235                 240

Lys Asp Met Thr Gly Ala Val Leu Ser Pro His Asp Ala Ala Leu Leu
                245                 250                 255

Met Arg Gly Ile Lys Thr Leu Asn Leu Arg Met Asp Arg His Cys Ala
            260                 265                 270

Asn Ala Gln Val Leu Ala Glu Phe Leu Ala Arg Gln Pro Gln Val Glu
            275                 280                 285

Leu Ile His Tyr Pro Gly Leu Ala Ser Phe Pro Gln Tyr Thr Leu Ala
290                 295                 300

Arg Gln Gln Met Ser Gln Pro Gly Gly Met Ile Ala Phe Glu Leu Lys
305                 310                 315                 320

Gly Gly Ile Gly Ala Gly Arg Arg Phe Met Asn Ala Leu Gln Leu Phe
                325                 330                 335

Ser Arg Ala Val Ser Leu Gly Asp Ala Glu Ser Leu Ala Gln His Pro
            340                 345                 350

Ala Ser Met Thr His Ser Ser Tyr Thr Pro Glu Glu Arg Ala His Tyr
            355                 360                 365

Gly Ile Ser Glu Gly Leu Val Arg Leu Ser Val Gly Leu Glu Asp Ile
    370                 375                 380

Asp Asp Leu Leu Ala Asp Val Gln Gln Ala Leu Lys Ala Ser Ala
385                 390                 395

<210> SEQ ID NO 3
<211> LENGTH: 1202
<212> TYPE: DNA
<213> ORGANISM: Artificial sequence
<220> FEATURE:
<223> OTHER INFORMATION: Pseudomonas putida methionine gamma-lyase
      sequence, with glycine codon inserted to incorporate restriction
      site and numerous naturally occurring codons changed to codons
      more commonly used in enteric bacteria

<400> SEQUENCE: 3
```

```
catgggtcac ggctccaaca aactgccggg ctttgctacc cgcgctatcc accacggtta    60
tgacccgcag gatcacggtg gtgcactggt tccgccggtt taccagactg ctactttcac   120
cttcccgacc gttgaatacg cgcgctgcgtg ctttgctggc gaacaggctg gtcacttcta   180
ctcccgtatc tccaacccga ccctgaacct gctggaagca cgtatggcat ctctggaagg   240
cggcgaagct ggtctggcgc tggcatctgg tatgggcgcg atcacctcta ccctgtggac   300
cctgctgcgt ccgggtgacg aagttctgct gggcaacacc ctgtatggtt gtacttttgc   360
tttcctgcac cacggtatcg gtgaattcgg cgttaaactg cgtcacgtag atatggctga   420
cctgcaggca ctggaagcgg ctatgacccc ggctacccgt gttatctact tcgaatcccc   480
ggctaacccg aacatgcaca tggctgacat cgcaggtgtt gctaaaatcg ctcgtaagca   540
cggcgctacc gtagttgttg ataacaccta ctgtactccg tacctgcaac gtccgctgga   600
actgggcgct gacctggttg ttcactccgc tactaaatac ctgtccggcc acggcgacat   660
cactgctggc atcgtagtag ctcccaggc actggttgac cgtatccgtc tgcaaggtct   720
gaaagacatg accggcgctg ttctgtcccc gcacgacgca gcactgctga tgcgtggtat   780
caagaccctg aacctgcgta tggaccgtca ctgtgctaac gctcaggtac tggctgaatt   840
cctggctcgt cagccgcagg tagaactgat ccactatccg ggcctggctt ccttcccgca   900
gtacactctg gcacgtcagc agatgtccca gccgggcggt atgatcgctt cgaactgaa   960 gggtggcatc ggcgctggtc gtcgtttcat gaacgctctg cagctgttct cccgtgcggt  1020
ttccctgggt gacgctgaat ccctggcgca gcacccggca tccatgactc actcctccta  1080
cactccggaa gaacgtgcgc actacggcat ctccgaaggc ctggttcgtc tgtctgttgg  1140
tctggaagac atcgatgatc tgctggcaga cgttcagcag gctctgaagg ctagcgcttg  1200
ag                                                                 1202
```

<210> SEQ ID NO 4
<211> LENGTH: 426
<212> TYPE: DNA
<213> ORGANISM: Artificial sequence
<220> FEATURE:
<223> OTHER INFORMATION: Cloning fragment of SEQ ID NO. 3

<400> SEQUENCE: 4

```
catgggtcac ggctccaaca aactgccggg ctttgctacc cgcgctatcc accacggtta    60
tgacccgcag gatcacggtg gtgcactggt tccgccggtt taccagactg ctactttcac   120
cttcccgacc gttgaatacg cgcgctgcgt ctttgctggc gaacaggctg gtcacttcta   180
ctcccgtatc tccaacccga ccctgaacct gctggaagca cgtatggcat ctctggaagg   240
cggcgaagct ggtctggcgc tggcatctgg tatgggcgcg atcacctcta ccctgtggac   300
cctgctgcgt ccgggtgacg aagttctgct gggcaacacc ctgtatggtt gtacttttgc   360
tttcctgcac cacggtatcg gtgaattcgg cgttaaactg cgtcacgtag atatggctga   420
cctgca                                                             426
```

<210> SEQ ID NO 5
<211> LENGTH: 441
<212> TYPE: DNA
<213> ORGANISM: Artificial sequence
<220> FEATURE:
<223> OTHER INFORMATION: Cloning fragment of SEQ ID NO. 3

<400> SEQUENCE: 5

```
caagaggcca tgggtcacgg ctccaacaaa ctgccgggct tgctacccg cgctatccac    60
```

-continued

| | |
|---|---|
| cacggttatg acccgcagga tcacggtggt gcactggttc cgccggttta ccagactgct | 120 |
| actttcacct tcccgaccgt tgaatacggc gctgcgtgct ttgctggcga acaggctggt | 180 |
| cacttctact cccgtatctc aacccgacc ctgaacctgc tggaagcacg tatggcatct | 240 |
| ctggaaggcg gcgaagctgg tctggcgctg gcatctggta tgggcgcgat cacctctacc | 300 |
| ctgtggaccc tgctgcgtcc gggtgacgaa gttctgctgg caacaccct gtatggttgt | 360 |
| acttttgctt tcctgcacca cggtatcggt gaattcggcg ttaaactgcg tcacgtagat | 420 |
| atggctgacc tgcaggcact g | 441 |

<210> SEQ ID NO 6
<211> LENGTH: 410
<212> TYPE: DNA
<213> ORGANISM: Artificial sequence
<220> FEATURE:
<223> OTHER INFORMATION: Cloning fragment of SEQ ID NO. 3

<400> SEQUENCE: 6

| | |
|---|---|
| ggcactggaa gcggctatga ccccggctac ccgtgttatc tacttcgaat ccccggctaa | 60 |
| cccgaacatg cacatggctg acatcgcagg tgttgctaaa atcgctcgta agcacggcgc | 120 |
| taccgtagtt gttgataaca cctactgtac tccgtacctg caacgtccgc tggaactggg | 180 |
| cgctgacctg gttgttcact ccgctactaa atacctgtcc ggccacggcg acatcactgc | 240 |
| tggcatcgta gtaggctccc aggcactggt tgaccgtatc cgtctgcaag gtctgaaaga | 300 |
| catgaccggc gctgttctgt ccccgcacga cgcagcactg ctgatgcgtg gtatcaagac | 360 |
| cctgaacctg cgtatggacc gtcactgtgc taacgctcag gtactggctg | 410 |

<210> SEQ ID NO 7
<211> LENGTH: 430
<212> TYPE: DNA
<213> ORGANISM: Artificial sequence
<220> FEATURE:
<223> OTHER INFORMATION: Cloning fragment of SEQ ID NO. 3

<400> SEQUENCE: 7

| | |
|---|---|
| gctgacctgc aggcactgga agcggctatg accccggcta cccgtgttat ctacttcgaa | 60 |
| tccccggcta acccgaacat gcacatggct gacatcgcag gtgttgctaa atcgctcgt | 120 |
| aagcacggcg ctaccgtagt tgttgataac acctactgta ctccgtacct gcaacgtccg | 180 |
| ctggaactgg gcgctgacct ggttgttcac tccgctacta aatacctgtc cggccacggc | 240 |
| gacatcactg ctggcatcgt agtaggctcc caggcactgg ttgaccgtat ccgtctgcaa | 300 |
| ggtctgaaag acatgaccgg cgctgttctg tccccgcacg acgcagcact gctgatgcgt | 360 |
| ggtatcaaga ccctgaacct gcgtatggac cgtcactgtg ctaacgctca ggtactggct | 420 |
| gaattcctgg | 430 |

<210> SEQ ID NO 8
<211> LENGTH: 366
<212> TYPE: DNA
<213> ORGANISM: Artificial sequence
<220> FEATURE:
<223> OTHER INFORMATION: Cloning fragment of SEQ ID NO. 3

<400> SEQUENCE: 8

| | |
|---|---|
| aattcctggc tcgtcagccg caggtagaac tgatccacta tccgggcctg gcttccttcc | 60 |
| cgcagtacac tctggcacgt cagcagatgt cccagccggg cggtatgatc gctttcgaac | 120 |

```
tgaagggtgg catcggcgct ggtcgtcgtt tcatgaacgc tctgcagctg ttctcccgtg    180
cggtttccct gggtgacgct gaatccctgg cgcagcaccc ggcatccatg actcactcct    240
cctacactcc ggaagaacgt gcgcactacg gcatctccga aggcctggtt cgtctgtctg    300
ttggtctgga agacatcgat gatctgctgg cagacgttca gcaggctctg aaggctagcg    360
cttgag                                                               366
```

<210> SEQ ID NO 9
<211> LENGTH: 383
<212> TYPE: DNA
<213> ORGANISM: Artificial sequence
<220> FEATURE:
<223> OTHER INFORMATION: Cloning fragment of SEQ ID NO. 3

<400> SEQUENCE: 9

```
tcttaatgaa ttcctggctc gtcagccgca ggtagaactg atccactatc cgggcctggc    60
ttccttcccg cagtacactc tggcacgtca gcagatgtcc cagccgggcg gtatgatcgc    120
tttcgaactg aagggtggca tcggcgctgg tcgtcgtttc atgaacgctc tgcagctgtt    180
ctcccgtgcg gtttcctgg gtgacgctga atccctggcg cagcacccgg catccatgac    240
tcactcctcc tacactccgg aagaacgtgc gcactacggc atctccgaag gcctggttcg    300
tctgtctgtt ggtctggaag acatcgatga tctgctggca gacgttcagc aggctctgaa    360
ggctagcgct tgaggatcca cca                                            383
```

<210> SEQ ID NO 10
<211> LENGTH: 33
<212> TYPE: DNA
<213> ORGANISM: Artificial Sequence
<220> FEATURE:
<223> OTHER INFORMATION: Primer/template derived from SEQ ID NO. 3

<400> SEQUENCE: 10

```
caagaggcca tgggtcacgg ctccaacaaa ctg                                  33
```

<210> SEQ ID NO 11
<211> LENGTH: 114
<212> TYPE: DNA
<213> ORGANISM: Artificial Sequence
<220> FEATURE:
<223> OTHER INFORMATION: Primer/template derived from SEQ ID NO. 3

<400> SEQUENCE: 11

```
cacggctcca acaaactgcc gggctttgct acccgcgcta tccaccacgg ttatgacccg    60
caggatcacg gtggtgcact ggttccgccg gtttaccaga ctgctacttt cacc          114
```

<210> SEQ ID NO 12
<211> LENGTH: 116
<212> TYPE: DNA
<213> ORGANISM: Artificial Sequence
<220> FEATURE:
<223> OTHER INFORMATION: Primer/template derived from SEQ ID NO. 3

<400> SEQUENCE: 12

```
gcttccagca ggttcagggt cgggttggag atacgggagt agaagtgacc agcctgttcg    60
ccagcaaagc acgcagcgcc gtattcaacg gtcgggaagg tgaaagtagc agtctg        116
```

<210> SEQ ID NO 13
<211> LENGTH: 117
<212> TYPE: DNA
<213> ORGANISM: Artificial Sequence

```
<220> FEATURE:
<223> OTHER INFORMATION: Primer/template derived from SEQ ID NO. 3

<400> SEQUENCE: 13
ctgaacctgc tggaagcacg tatggcatct ctggaaggcg gcgaagctgg tctggcgctg      60
gcatctggta tgggcgcgat cacctctacc ctgtggaccc tgctgcgtcc gggtgac        117

<210> SEQ ID NO 14
<211> LENGTH: 116
<212> TYPE: DNA
<213> ORGANISM: Artificial Sequence
<220> FEATURE:
<223> OTHER INFORMATION: Primer/template derived from SEQ ID NO. 3

<400> SEQUENCE: 14
gccatatcta cgtgacgcag tttaacgccg aattcaccga taccgtggtg caggaaagca      60
aaagtacaac catacagggt gttgcccagc agaacttcgt cacccggacg cagcag         116

<210> SEQ ID NO 15
<211> LENGTH: 33
<212> TYPE: DNA
<213> ORGANISM: Artificial Sequence
<220> FEATURE:
<223> OTHER INFORMATION: Primer/template derived from SEQ ID NO. 3

<400> SEQUENCE: 15
cagtgcctgc aggtcagcca tatctacgtg acg                                   33

<210> SEQ ID NO 16
<211> LENGTH: 33
<212> TYPE: DNA
<213> ORGANISM: Artificial Sequence
<220> FEATURE:
<223> OTHER INFORMATION: Primer/template derived from SEQ ID NO. 3

<400> SEQUENCE: 16
gctgacctgc aggcactgga agcggctatg acc                                   33

<210> SEQ ID NO 17
<211> LENGTH: 114
<212> TYPE: DNA
<213> ORGANISM: Artificial Sequence
<220> FEATURE:
<223> OTHER INFORMATION: Primer/template derived from SEQ ID NO. 3

<400> SEQUENCE: 17
ctggaggctg ctatgacccc ggctacccgt gttatctact tcgaatcccc ggctaacccg      60
aacatgcaca tggctgacat cgcaggtgtt gctaaaatcg ctcgtaagca cggc            114

<210> SEQ ID NO 18
<211> LENGTH: 115
<212> TYPE: DNA
<213> ORGANISM: Artificial Sequence
<220> FEATURE:
<223> OTHER INFORMATION: Primer/template derived from SEQ ID NO. 3

<400> SEQUENCE: 18
ggtatttagt agcggagtga acaaccaggt cagcgcccag ttccagcgga cgttgcaggt      60
acggagtaca gtaggtgtta tcaacaacta cggtagcgcc gtgcttacga gcgat          115

<210> SEQ ID NO 19
<211> LENGTH: 111
<212> TYPE: DNA
```

```
<213> ORGANISM: Artificial Sequence
<220> FEATURE:
<223> OTHER INFORMATION: Primer/template derived from SEQ ID NO. 3

<400> SEQUENCE: 19
cactccgcta ctaaatacct gtccggccac ggcgacatca ctgctggcat cgtagtaggc      60
tcccaggcac tggttgaccg tatccgtctg caaggtctga agacatgac c               111

<210> SEQ ID NO 20
<211> LENGTH: 115
<212> TYPE: DNA
<213> ORGANISM: Artificial Sequence
<220> FEATURE:
<223> OTHER INFORMATION: Primer/template derived from SEQ ID NO. 3

<400> SEQUENCE: 20
gtacctgagc gttagcacag tgacggtcca tacgcaggtt cagggtcttg ataccacgca      60
tcagcagtgc tgcgtcgtgc ggggacagaa cagcgccggt catgtctttc agacc           115

<210> SEQ ID NO 21
<211> LENGTH: 33
<212> TYPE: DNA
<213> ORGANISM: Artificial Sequence
<220> FEATURE:
<223> OTHER INFORMATION: Primer/template derived from SEQ ID NO. 3

<400> SEQUENCE: 21
ccaggaattc agccagtacc tgagcgttag cac                                   33

<210> SEQ ID NO 22
<211> LENGTH: 31
<212> TYPE: DNA
<213> ORGANISM: Artificial Sequence
<220> FEATURE:
<223> OTHER INFORMATION: Primer/template derived from SEQ ID NO. 3

<400> SEQUENCE: 22
tcttaatgaa ttcctggctc gtcagccgca g                                     31

<210> SEQ ID NO 23
<211> LENGTH: 105
<212> TYPE: DNA
<213> ORGANISM: Artificial Sequence
<220> FEATURE:
<223> OTHER INFORMATION: Primer/template derived from SEQ ID NO. 3

<400> SEQUENCE: 23
ctggctcgtc agccgcaggt agaactgatc cactatccgg gcctggcttc cttcccgcag      60
tacactctgg cacgtcagca gatgtcccag ccgggcggta tgatc                      105

<210> SEQ ID NO 24
<211> LENGTH: 106
<212> TYPE: DNA
<213> ORGANISM: Artificial Sequence
<220> FEATURE:
<223> OTHER INFORMATION: Primer/template derived from SEQ ID NO. 3

<400> SEQUENCE: 24
cgtcacccag ggaaaccgca cgggagaaca gctgcagagc gttcatgaaa cgacgaccag      60
cgccgatgcc acccttcagt tcgaaagcga tcatgccacc cggctg                     106

<210> SEQ ID NO 25
<211> LENGTH: 106
```

```
<212> TYPE: DNA
<213> ORGANISM: Artificial Sequence
<220> FEATURE:
<223> OTHER INFORMATION: Primer/template derived from SEQ ID NO. 3

<400> SEQUENCE: 25
gcggtttccc tgggtgacgc tgaatccctg gcgcagcacc cggcatccat gactcactcc    60
tcctacactc cggaagaacg tgcgcactac ggcatctccg aaggcc                  106

<210> SEQ ID NO 26
<211> LENGTH: 98
<212> TYPE: DNA
<213> ORGANISM: Artificial Sequence
<220> FEATURE:
<223> OTHER INFORMATION: Primer/template derived from SEQ ID NO. 3

<400> SEQUENCE: 26
caagcgctag ccttcagagc ctgctgaacg tctgccagca gatcatcgat gtcttccaga    60
ccaacagaca gacgaaccag gccttcggag atgccgta                           98

<210> SEQ ID NO 27
<211> LENGTH: 32
<212> TYPE: DNA
<213> ORGANISM: Artificial Sequence
<220> FEATURE:
<223> OTHER INFORMATION: Primer/template derived from SEQ ID NO. 3

<400> SEQUENCE: 27
tggtggatcc tcaagcgcta gccttcagag cc                                 32

<210> SEQ ID NO 28
<211> LENGTH: 1197
<212> TYPE: DNA
<213> ORGANISM: Artificial Sequence
<220> FEATURE:
<223> OTHER INFORMATION: Methionine gamma-lyase gene derived from
      Pseudomonas putida, having all arginine codons replaced with
      arginine codons found most commonly in E. coli

<400> SEQUENCE: 28
atgcacggct ccaacaagct cccaggattt gccacccgcg ccattcacca tggctacgac    60
ccccaggacc acgcggcgc actggtgcca ccggtctacc agaccgcgac gttcaccttc    120
cccaccgtgg aatacggcgc tgcgtgcttt gccggcgagc aggccgggca tttctacagc    180
cgcatctcca accccaccct caacctgctg gaagcacgca tggcctcgct ggaaggcggc    240
gaggccgggc tggcgctggc ctcgggcatg ggggcgatca cgtccacgct atggacactg    300
ctgcgccccg gtgacgaggt gctgctgggc aacaccctgt acggctgcac ctttgccttc    360
ctgcaccacg gcatcggcga gttcggggtc aagctgcgcc atgtggacat ggccgacctg    420
caggcactgg aggcggccat gacgccggcc accgtgtga tctatttcga gtcgccggcc    480
aaccccaaca tgcacatggc cgatatcgcc ggcgtggcga agattgcacg caagcacggc    540
gcgaccgtgg tggtcgacaa cacctactgc acgccgtacc tgcaacgtcc actggagctg    600
ggcgccgacc tggtggtgca ttcggccacc aagtacctga gcggccatgg cgacatcact    660
gctggcattg tggtgggcag ccaggcactg gtggaccgta cgtctgca gggcctcaag    720 gacatgaccg gtgcggtgct ctcgccccat gacgccgcac tgttgatgcg cggcatcaag    780
accctcaacc tgcgcatgga ccgccactgc gccaacgctc aggtgctggc cgagttcctc    840
gcccgtcagc cgcaggtgga gctgatccat tacccggggc tggcgagctt cccgcagtac    900
```

```
accctggccc gccagcagat gagccagccg ggcggcatga tcgccttcga actcaagggc    960
ggcatcggtg ccgggcgtcg tttcatgaac gccctgcaac tgttcagccg cgcggtgagc   1020
ctgggcgatg ccgagtcgct ggcgcagcac ccggcaagca tgactcattc cagctatacc   1080
ccagaggagc gtgcgcatta cggcatctcc gaggggctgg tgcgtttgtc ggtggggctg   1140
gaagacatcg acgacctgct ggccgatgtg caacaggcac tcaaggcgag tgcctga      1197
```

<210> SEQ ID NO 29
<211> LENGTH: 1197
<212> TYPE: DNA
<213> ORGANISM: Artificial Sequence
<220> FEATURE:
<223> OTHER INFORMATION: Methionine gamma-lyase gene derived from
      Pseudomonas putida having all rare arginine, leucine, isoleucine,
      and proline codons replaced with respective corresponding codons
      found most commonly in E. coli

<400> SEQUENCE: 29

```
atgcacggct ccaacaagct cccaggattt gccacccgcg ccattcacca tggctacgac     60
ccgcaggacc acggcggcgc actggtgcca ccggtctacc agaccgcgac gttcaccttc    120
ccgaccgtgg aatacggcgc tgcgtgcttt gccggcgagc aggccgggca tttctacagc    180
cgcatctcca acccgaccct caacctgctg gaagcacgca tggcctcgct ggaaggcggc    240
gaggccgggc tggcgctggc ctcgggcatg ggggcgatca cgtccacgct gtggacactg    300
ctgcgcccgg gtgacgaggt gctgctgggc aaccccctgt acggctgcac ctttgccttc    360
ctgcaccacg gcatcggcga gttcggggtc aagctgcgcc atgtggacat ggccgacctg    420
caggcactgg aggcggccat gacgccggcc acccgtgtga tctatttcga gtcgccggcc    480
aacccgaaca tgcacatggc cgatatcgcc ggcgtggcga agattgcacg caagcacggc    540
gcgaccgtgg tggtcgacaa cacctactgc acgccgtacc tgcaacgtcc actggagctg    600
ggcgccgacc tggtggtgca ttcggccacc aagtacctga gcggccatgg cgacatcact    660
gctggcattg tggtgggcag ccaggcactg gtggaccgta tccgtctgca gggcctcaag    720
gacatgaccg tgcggtgct ctcgccgcat gacgccgcac tgttgatgcg cggcatcaag    780
accctcaacc tgcgcatgga ccgccactgc gccaacgctc aggtgctggc cgagttcctc    840
gcccgtcagc gcaggtgga gctgatccat tacccgggcc tggcgagctt cccgcagtac    900
accctggccc gccagcagat gagccagccg ggcggcatga tcgccttcga actcaagggc    960
ggcatcggtg ccgggcgtcg tttcatgaac gccctgcaac tgttcagccg cgcggtgagc   1020
ctgggcgatg ccgagtcgct ggcgcagcac ccggcaagca tgactcattc cagctatacc   1080
ccagaggagc gtgcgcatta cggcatctcc gaggggctgg tgcgtttgtc ggtggggctg   1140
gaagacatcg acgacctgct ggccgatgtg caacaggcac tcaaggcgag tgcctga      1197
```

<210> SEQ ID NO 30
<211> LENGTH: 1200
<212> TYPE: DNA
<213> ORGANISM: Artificial Sequence
<220> FEATURE:
<223> OTHER INFORMATION: Methionine gamma-lyase gene derived from
      Pseudomonas putida having all codons replaced with respective
      corresponding codons found most commonly in E. coli

<400> SEQUENCE: 30

```
atgggtcacg gctccaacaa actgccgggt tttgctaccc gtgctatcca ccacggctac     60
gacccgcagg accacggcgg cgcactggtt ccgccggttt accagaccgc gaccttcacc    120
```

-continued

```
ttcccgaccg ttgaatacgg cgctgcgtgc tttgctggcg aacaggctgg tcacttctac       180
tcccgtatct ccaacccgac cctgaacctg ctggaagcac gtatggcttc cctggaaggc       240
ggcgaagctg gtctggcgct ggcttccggc atgggtgcga tcacctccac cctgtggacc       300
ctgctgcgtc cgggtgacga agttctgctg gcaacaccc tgtacggctg cacctttgct       360
ttcctgcacc acggcatcgg cgaattcggt gttaagctgc gtcacgttga catggctgac       420
ctgcaggcac tggaagcggc tatgacccccg ctacccgtg ttatctactt cgaatccccg      480
gctaacccga acatgcacat ggctgaaatc gctggcgttg cgaagatcgc acgtaagcac      540
ggcgcgaccg ttgttgttga caacacctac tgcaccccgt acctgcaacg tccgctggaa      600
ctgggcgctg acctggttgt tcactccgct accaagtacc tgtccggcca cggcgacatc      660
actgctggca tcgttgttgg ctcccaggca ctggttgacc gtatccgtct gcaaggcctg      720
aaggacatga ccggtgcggt tctgtccccg cacgacgctg cactgctgat cgtggcatc      780
aagaccctga acctgcgtat ggaccgtcac tgcgctaacg ctcaggttct ggctgaattc      840
ctggctcgtc agccgcaggt tgaactgatc cactacccgg gcctggcgtc cttcccgcag      900
tacaccctgg ctcgtcagca gatgtcccag ccgggcggca tgatcgcttt cgaactgaag      960
ggcggcatcg gtgctggtcg tcgtttcatg aacgctctgc agctgttctc ccgtgcggtt     1020
tccctgggcg aagctgaatc cctggcgcag cacccggcat ccatgactca ctcctcctac     1080
accccggaag aacgtgcgca ctacggcatc tccgaaggtc tggttcgtct gtccgttggt     1140
ctggaagaca tcgacgacct gctggctgaa gttcagcagg cactgaaggc gagtgcttga    1200
```

<210> SEQ ID NO 31
<211> LENGTH: 972
<212> TYPE: DNA
<213> ORGANISM: Sporidiobolus salmonicolor

<400> SEQUENCE: 31

```
atggtcggca ctactacccct caacactggc gcttccctcg agctcgtcgg ctacggcacg        60
tggcaggcag caccgggcga ggtgggccag ggcgtcaagg tcgccatcga gactggatac       120
cgtcacctcg accttgccaa ggtctactcg aaccaacctg aggttggtgc cgccatcaag       180
gaggctggcg tcaagcgcga ggacctcttc atcacctcga agctctggaa caactcgcac       240
cgcccggagc aggtcgagcc tgcccttgac gacaccctca aggagctcgg cctcgagtac       300
ctcgaccttt acctcattca ctggcccgtc gcgttcccgc cgagggcga catcacccag       360
aacctcttcc cgaaggccaa cgacaaggag gtcaagctcg acctggaggt cagcctcgtc       420
gacacgtgga aggcgatggt caagcttctc gacactggca aggtcaaggc gatcggcgtt       480
tccaacttcg acgcgaagat ggtcgacgcc atcatcgagg ctaccggcgt gacccctcc       540
gtcaaccaga tcgagcgtca ccctctcctt ctccagcccg agctcatcgc ccaccacaag       600
gccaagaaca ttcacattac cgcatactct cctctcggta caacaccgt cggcgcgcct       660
cttcttgtcc agcacccgga gatcaagcgc atcgccgaga gaacggctg cacgcccgct       720
caggtcctca ttgcctgggc catcgttggc ggccactcgg ttatccccaa gtcggtcacc       780
ccctcccgca ttggcgagaa cttcaagcag gtctcgctct cgcaggagga cgtcgatgcc       840
gtcagcaagc tcggcgaggg ttcggccgcg aggcgctaca acatcccctg cacgtactcg       900
cccaagtggg acatcaacgt ctttggcgag gaggacgaga gtcgtgcaa gaacgccgtg       960
aagatcaagt ag                                                           972
```

<210> SEQ ID NO 32
<211> LENGTH: 322
<212> TYPE: PRT
<213> ORGANISM: Sporidiobolus salmonicolor

<400> SEQUENCE: 32

Met Val Gly Thr Thr Thr Leu Asn Thr Gly Ala Ser Leu Glu Leu Val
1               5                   10                  15

Gly Tyr Gly Thr Trp Gln Ala Ala Pro Gly Glu Val Gly Gln Gly Val
            20                  25                  30

Lys Val Ala Ile Glu Thr Gly Tyr Arg His Leu Asp Leu Ala Lys Val
        35                  40                  45

Tyr Ser Asn Gln Pro Glu Val Gly Ala Ala Ile Lys Glu Ala Gly Val
    50                  55                  60

Lys Arg Glu Asp Leu Phe Ile Thr Ser Lys Leu Trp Asn Asn Ser His
65                  70                  75                  80

Arg Pro Glu Gln Val Glu Pro Ala Leu Asp Asp Thr Leu Lys Glu Leu
                85                  90                  95

Gly Leu Glu Tyr Leu Asp Leu Tyr Leu Ile Trp Pro Val Ala Phe Pro
            100                 105                 110

Pro Glu Gly Asp Ile Thr Gln Asn Leu Phe Pro Lys Ala Asn Asp Lys
        115                 120                 125

Glu Val Lys Leu Asp Leu Glu Val Ser Leu Val Asp Thr Trp Lys Ala
    130                 135                 140

Met Val Lys Leu Leu Asp Thr Gly Lys Val Lys Ala Ile Gly Val Ser
145                 150                 155                 160

Asn Phe Asp Ala Lys Met Val Asp Ala Ile Ile Glu Ala Thr Gly Val
                165                 170                 175

Thr Pro Ser Val Asn Gln Ile Glu Arg His Pro Leu Leu Leu Gln Pro
            180                 185                 190

Glu Leu Ile Ala His His Lys Ala Lys Asn Ile His Ile Thr Ala Tyr
        195                 200                 205

Ser Pro Leu Gly Asn Asn Thr Val Gly Ala Pro Leu Leu Val Gln His
    210                 215                 220

Pro Glu Ile Lys Arg Ile Ala Glu Lys Asn Gly Cys Thr Pro Ala Gln
225                 230                 235                 240

Val Leu Ile Ala Trp Ala Ile Val Gly Gly His Ser Val Ile Pro Lys
                245                 250                 255

Ser Val Thr Pro Ser Arg Ile Gly Glu Asn Phe Lys Gln Val Ser Leu
            260                 265                 270

Ser Gln Glu Asp Val Asp Ala Val Ser Lys Leu Gly Glu Gly Ser Gly
        275                 280                 285

Arg Arg Arg Tyr Asn Ile Pro Cys Thr Tyr Ser Pro Lys Trp Asp Ile
    290                 295                 300

Asn Val Phe Gly Glu Glu Asp Glu Lys Ser Cys Lys Asn Ala Val Lys
305                 310                 315                 320

Ile Lys

<210> SEQ ID NO 33
<211> LENGTH: 972
<212> TYPE: DNA
<213> ORGANISM: Artificial sequence
<220> FEATURE:
<223> OTHER INFORMATION: Synthetic gene derived from Sporidiobolus
      salmonicolor NADPH-Dependent Aldehyde Reductase 1, having numerous
      codons replaced with others encoding the same amino acids to
      reduce the free energy of folding

<400> SEQUENCE: 33

```
atggttggta ctactactct gaacactggt gcatctctgg aactggtagg ttatggtact      60
tggcaagctg ctccgggcga agtaggtcaa ggtgtaaaag tagctatcga aactggttat     120
cgtcatctgg atctggcaaa agtatactct aaccagccgg aagtaggtgc agcaatcaag     180
gaagctggcg ttaaacgtga ggatctgttt atcacttcta aactgtggaa caactcccac     240
cgtccggaac aggtagaacc ggctctggat gatactctga agaactggg cctggagtat      300
ctggacctgt acctgatcca ctggccggta gcatttccgc cggaaggtga tatcactcag     360
aacctgttcc cgaaagctaa cgataaagaa gtaaaactgg acctggaagt ttctctggta     420
gacacttgga agcaatggt aaaactgctg gatactggta agttaaagc tatcggtgtt       480
tccaactttg acgcaaaaat ggttgacgct atcatcgaag caactggcgt aactccgtct     540
gttaaccaga tcgaacgtca cccgctgctg ctgcagccag agctgatcgc acaccacaaa     600
gctaaaaaca tccacatcac cgcatactcc ccgctgggta caacaccgt aggcgcaccg      660
ctgctggtac aacacccgga aatcaaacgt atcgctgaaa aaacggctg tactccggct      720
caggtactga tcgcatgggc tatcgtaggt ggtcattctg ttatcccgaa atccgtaact     780
ccgtctcgta ttggcgaaaa cttcaaacag gtttctctgt ctcaggaaga tgttgatgct     840
gtttctaagc tgggcgaagg ttccggtcgt cgtcgttata acatcccgtg cacttattcc     900
ccgaagtggg atatcaacgt tttcggtgaa gaagatgaaa atcctgtaa aaacgctgtt      960
aaaatcaaat aa                                                         972
```

<210> SEQ ID NO 34
<211> LENGTH: 1032
<212> TYPE: DNA
<213> ORGANISM: Sporidiobolus salmonicolor

<400> SEQUENCE: 34

```
atggccaaaa tcgacaacgc tgtgcttccc gagggctcgc tcgtgctcgt caccggcgcc      60
aacggcttcg tcgcttcgca cgtcgtcgaa cagctccttg aacacggtta caaggtccgt     120
ggtacggctc gtagtgcctc caaacttgcc aacctgcaga agcgctggga tgccaagtac     180
cccggtcgct tcgagacggc cgtggtcgag gacatgctca acagggagc ttacgacgaa      240
gtgatcaagg gcgccgccgg agttgcgcac atcgcttccg tcgtgtcctt ctcgaacaag     300
tacgacgagg ttgtcacccc cgccatcgga ggcacccctca acgctctccg tgccgccgct   360
gccacgccct ctgtcaagcg cttcgtcctc acctcctcga ccgtttcagc gcttatcccc     420
aagccgaatg tcgaggggat ctacctcgac gagaagtcct ggaacctcga gagcatcgac     480
aaggccaaga ctctccctga aagcgacccc cagaagtcgc tctgggtcta cgccgcgagc     540
aagaccgagg cggagcttgc cgcttggaaa ttcatggacg agaacaagcc gcacttcacc     600
ctcaacgccg tcctccccaa ctacacgatt ggacgatct tcgaccccga gacccagtcc      660
ggctcgactt cgggctggat gatgagtctc ttcaatggcg aagtttcccc cgccctcgct     720
ctgatgcccc ctcagtacta cgtgtcggcc gtcgacattg gtctcctgca cctcgggtgc     780
ttggttctgc cccagatcga gcgccgccgc gtctacggca ccgccggcac gttcgactgg     840
aacacggtcc tcgcgacgtt ccgcaagctg tacccgagca agacgttccc ggccgacttc     900
cccgaccagg gccaggacct ctccaagttc gacacggccc cgagcctcga gatcctcaag     960
agtttgggca ggcccgggtg gaggtcgatc gaggagagca tcaaggacct cgtcggctcc    1020
```

-continued gaaaccgctt ga 1032

<210> SEQ ID NO 35
<211> LENGTH: 343
<212> TYPE: PRT
<213> ORGANISM: Sporidiobolus salmonicolor

<400> SEQUENCE: 35

Met Ala Lys Ile Asp Asn Ala Val Leu Pro Glu Gly Ser Leu Val Leu
1               5                   10                  15

Val Thr Gly Ala Asn Gly Phe Val Ala Ser His Val Val Glu Gln Leu
            20                  25                  30

Leu Glu His Gly Tyr Lys Val Arg Gly Thr Ala Arg Ser Ala Ser Lys
        35                  40                  45

Leu Ala Asn Leu Gln Lys Arg Trp Asp Ala Lys Tyr Pro Gly Arg Phe
    50                  55                  60

Glu Thr Ala Val Glu Asp Met Leu Lys Gln Gly Ala Tyr Asp Glu
65                  70                  75                  80

Val Ile Lys Gly Ala Ala Gly Val Ala His Ile Ala Ser Val Val Ser
                85                  90                  95

Phe Ser Asn Lys Tyr Asp Glu Val Val Thr Pro Ala Ile Gly Gly Thr
            100                 105                 110

Leu Asn Ala Leu Arg Ala Ala Ala Thr Pro Ser Val Lys Arg Phe
        115                 120                 125

Val Leu Thr Ser Ser Thr Val Ser Ala Leu Ile Pro Lys Pro Asn Val
130                 135                 140

Glu Gly Ile Tyr Leu Asp Glu Lys Ser Trp Asn Leu Glu Ser Ile Asp
145                 150                 155                 160

Lys Ala Lys Thr Leu Pro Glu Ser Asp Pro Gln Lys Ser Leu Trp Val
                165                 170                 175

Tyr Ala Ala Ser Lys Thr Glu Ala Glu Leu Ala Ala Trp Lys Phe Met
            180                 185                 190

Asp Glu Asn Lys Pro His Phe Thr Leu Asn Ala Val Leu Pro Asn Tyr
        195                 200                 205

Thr Ile Gly Thr Ile Phe Asp Pro Glu Thr Gln Ser Gly Ser Thr Ser
    210                 215                 220

Gly Trp Met Met Ser Leu Phe Asn Gly Glu Val Ser Pro Ala Leu Ala
225                 230                 235                 240

Leu Met Pro Pro Gln Tyr Tyr Val Ser Ala Val Asp Ile Gly Leu Leu
                245                 250                 255

His Leu Gly Cys Leu Val Leu Pro Gln Ile Glu Arg Arg Val Tyr
            260                 265                 270

Gly Thr Ala Gly Thr Phe Asp Trp Asn Thr Val Leu Ala Thr Phe Arg
        275                 280                 285

Lys Leu Tyr Pro Ser Lys Thr Phe Pro Ala Asp Phe Pro Asp Gln Gly
    290                 295                 300

Gln Asp Leu Ser Lys Phe Asp Thr Ala Pro Ser Leu Glu Ile Leu Lys
305                 310                 315                 320

Ser Leu Gly Arg Pro Gly Trp Arg Ser Ile Glu Glu Ser Ile Lys Asp
                325                 330                 335

Leu Val Gly Ser Glu Thr Ala
            340

<210> SEQ ID NO 36
<211> LENGTH: 1032

<212> TYPE: DNA
<213> ORGANISM: Artificial Sequence
<220> FEATURE:
<223> OTHER INFORMATION: Synthetic gene derived from Sporidiobolus
    salmonicolor NADPH-Dependent Aldehyde Reductase 2, having numerous
    codons replaced with others encoding the same amino acids to
    reduce the free energy of folding, and an ala to gly mutation at
    amino acid position 2

<400> SEQUENCE: 36

```
atggctaaaa tcgataacgc agttctgccg gaaggttccc tggttctggt taccggtgct      60
aacggtttcg ttggttccca cgttgttgaa cagctgctgg aacacggtta caaagttcgt     120
ggtaccgctc gttccgcttc aaactggct aacctgcaga acgttggga cgctaaatac       180
ccgggtcgtt tcgaaaccgc tgttgttgaa gacatgctga acagggtgc ttacgacgaa      240
gttatcaaag gtgctgctgg tgttgctcac atcgcttccg ttgtttcctt ctccaacaaa     300
tacgacgaag ttgttacccc ggctatcggt ggtaccctga cgctctgcg tgctgctgct     360
gctaccccgt ccgttaaacg tttcgttctg acctcctcca ccgtttccgc tctgatcccg     420
aaaccgaacg ttgaaggtat ctacctggac gaaaaatcct ggaacctgga atccatcgac    480
aaagctaaaa ccctgccgga atccgacccg cagaaatccc tgtgggtata cgctgcatcc    540
aagaccgaag ctgaactggc tgcatggaaa tttatggatg agaacaagcc acacttcact    600
ctgaacgctg tactgccaaa ctacactatt ggcactatct tcgatccgga aactcagtcc    660
ggttccacct ccggttggat gatgtccctg tttaacggcg aggtttcccc ggctctggct    720
ctgatgccac cgcagtacta cgtttccgct gttgatattg cctgctgca cctgggttgc    780
ctggttctgc acaaatcga acgtcgtcgt gtttacggta ctgctggtac tttcgattgg    840
aacaccgttc tggctacctt ccgtaaactg tacccgtcca aaaccttccc ggctgacttc    900
ccagatcaag gtcaggacct gtctaaattc gacaccgctc cgtccctgga aattctgaaa    960
tctctgggtc gcccaggttg gcgttccatc gaagaatcca tcaaagacct ggttggttcc   1020
gaaaccgctt aa                                                       1032
```

<210> SEQ ID NO 37
<211> LENGTH: 343
<212> TYPE: PRT
<213> ORGANISM: Artificial Sequence
<220> FEATURE:
<223> OTHER INFORMATION: Synthetic protein derived from Sporidiobolus
    salmonicolor NADPH-Dependent Aldehyde Reductase 2, having an ala
    to gly mutation at amino acid position 2

<400> SEQUENCE: 37

```
Met Ala Lys Ile Asp Asn Ala Val Leu Pro Glu Gly Ser Leu Val Leu
1               5                  10                  15

Val Thr Gly Ala Asn Gly Phe Val Gly Ser His Val Val Glu Gln Leu
            20                  25                  30

Leu Glu His Gly Tyr Lys Val Arg Gly Thr Ala Arg Ser Ala Ser Lys
        35                  40                  45

Leu Ala Asn Leu Gln Lys Arg Trp Asp Ala Lys Tyr Pro Gly Arg Phe
    50                  55                  60

Glu Thr Ala Val Val Glu Asp Met Leu Lys Gln Gly Ala Tyr Asp Glu
65                  70                  75                  80

Val Ile Lys Gly Ala Ala Gly Val Ala His Ile Ala Ser Val Val Ser
                85                  90                  95

Phe Ser Asn Lys Tyr Asp Glu Val Val Thr Pro Ala Ile Gly Gly Thr
            100                 105                 110
```

Leu Asn Ala Leu Arg Ala Ala Ala Thr Pro Ser Val Lys Arg Phe
            115                 120                 125

Val Leu Thr Ser Ser Thr Val Ser Ala Leu Ile Pro Lys Pro Asn Val
    130                 135                 140

Glu Gly Ile Tyr Leu Asp Glu Lys Ser Trp Asn Leu Glu Ser Ile Asp
145                 150                 155                 160

Lys Ala Lys Thr Leu Pro Glu Ser Asp Pro Gln Lys Ser Leu Trp Val
                165                 170                 175

Tyr Ala Ala Ser Lys Thr Glu Ala Glu Leu Ala Ala Trp Lys Phe Met
            180                 185                 190

Asp Glu Asn Lys Pro His Phe Thr Leu Asn Ala Val Leu Pro Asn Tyr
        195                 200                 205

Thr Ile Gly Thr Ile Phe Asp Pro Glu Thr Gln Ser Gly Ser Thr Ser
    210                 215                 220

Gly Trp Met Met Ser Leu Phe Asn Gly Glu Val Ser Pro Ala Leu Ala
225                 230                 235                 240

Leu Met Pro Pro Gln Tyr Tyr Val Ser Ala Val Asp Ile Gly Leu Leu
                245                 250                 255

His Leu Gly Cys Leu Val Leu Pro Gln Ile Glu Arg Arg Val Tyr
            260                 265                 270

Gly Thr Ala Gly Thr Phe Asp Trp Asn Thr Val Leu Ala Thr Phe Arg
        275                 280                 285

Lys Leu Tyr Pro Ser Lys Thr Phe Pro Ala Asp Phe Pro Asp Gln Gly
    290                 295                 300

Gln Asp Leu Ser Lys Phe Asp Thr Ala Pro Ser Leu Glu Ile Leu Lys
305                 310                 315                 320

Ser Leu Gly Arg Pro Gly Trp Arg Ser Ile Glu Glu Ser Ile Lys Asp
                325                 330                 335

Leu Val Gly Ser Glu Thr Ala
            340

<210> SEQ ID NO 38
<211> LENGTH: 942
<212> TYPE: DNA
<213> ORGANISM: Saccharomyces cerevisiae

<400> SEQUENCE: 38
atgggtcctg ctacgttaaa gaattcttct gctacattaa aactaaatac tggtgcctcc      60
attccagtgt tgggtttcgg cacttggcgt tccgttgaca taacggttta ccattctgta     120
attgcagctt tgaaagctgg atacagacac attgatgctg cggctatcta tttgaatgaa     180
gaagaagttg caggctat taaagattcc ggagtccctc gtgaggaaat ttttattact     240
actaagcttt ggggtacgga caacgtgat ccggaagctg ctctaaacaa gtctttgaaa     300
agactaggct tggattatgt tgacctatat ctgatgcatt ggccagtgcc tttgaaaacc     360
gacagagtta ctgatggtaa cgttctgtgc attccaacat agaagatgg cactgttgac     420 atcgatacta aggaatggaa tttttatcaag acgtgggagt tgatgcaaga gttgccaaag     480
acgggcaaaa ctaaagccgt tggtgtctct aattttttcta ttaacaacat taagaatta     540 ttagaatctc caaataacaa ggtggtacca gctactaatc aaattgaaat tcatccattg     600
ctaccacaag acgaattgat tgccttttgt aaggaaaagg gtattgttgt tgaagcctac     660
tcaccatttg ggagtgctaa tgctccttta ctaaaagagc aagcaattat tgatatggct     720
aaaaagcacg gcgttgagcc agcacagctt attatcagtt ggagtattca agaggctac     780

```
gttgttctgg ccaaatcggt taatcctgaa agaattgtat ccaattttaa gattttcact      840
ctgcctgagg atgatttcaa gactattagt aacctatcca aagtgcatgg tacaaagaga      900
gtcgttgata tgaagtgggg atccttccca attttccaat ga                        942
```

```
<210> SEQ ID NO 39
<211> LENGTH: 313
<212> TYPE: PRT
<213> ORGANISM: Saccharomyces cerevisiae

<400> SEQUENCE: 39
```

```
Met Gly Pro Ala Thr Leu Lys Asn Ser Ser Ala Thr Leu Lys Leu Asn
1               5                   10                  15

Thr Gly Ala Ser Ile Pro Val Leu Gly Phe Gly Thr Trp Arg Ser Val
            20                  25                  30

Asp Asn Asn Gly Tyr His Ser Val Ile Ala Ala Leu Lys Ala Gly Tyr
        35                  40                  45

Arg His Ile Asp Ala Ala Ile Tyr Leu Asn Glu Glu Val Gly
    50                  55                  60

Arg Ala Ile Lys Asp Ser Gly Val Pro Arg Glu Glu Ile Phe Ile Thr
65                  70                  75                  80

Thr Lys Leu Trp Gly Thr Glu Gln Arg Asp Pro Glu Ala Ala Leu Asn
                85                  90                  95

Lys Ser Leu Lys Arg Leu Gly Leu Asp Tyr Val Asp Leu Tyr Leu Met
            100                 105                 110

His Trp Pro Val Pro Leu Lys Thr Asp Arg Val Thr Asp Gly Asn Val
        115                 120                 125

Leu Cys Ile Pro Thr Leu Glu Asp Gly Thr Val Asp Ile Asp Thr Lys
    130                 135                 140

Glu Trp Asn Phe Ile Lys Thr Trp Glu Leu Met Gln Glu Leu Pro Lys
145                 150                 155                 160

Thr Gly Lys Thr Lys Ala Val Gly Val Ser Asn Phe Ser Ile Asn Asn
                165                 170                 175

Ile Lys Glu Leu Leu Glu Ser Pro Asn Asn Lys Val Val Pro Ala Thr
            180                 185                 190

Asn Gln Ile Glu Ile His Pro Leu Leu Pro Gln Asp Glu Leu Ile Ala
        195                 200                 205

Phe Cys Lys Glu Lys Gly Ile Val Val Glu Ala Tyr Ser Pro Phe Gly
    210                 215                 220

Ser Ala Asn Ala Pro Leu Leu Lys Glu Gln Ala Ile Ile Asp Met Ala
225                 230                 235                 240

Lys Lys His Gly Val Glu Pro Ala Gln Leu Ile Ile Ser Trp Ser Ile
                245                 250                 255

Gln Arg Gly Tyr Val Val Leu Ala Lys Ser Val Asn Pro Glu Arg Ile
            260                 265                 270

Val Ser Asn Phe Lys Ile Phe Thr Leu Pro Glu Asp Phe Lys Thr
        275                 280                 285

Ile Ser Asn Leu Ser Lys Val His Gly Thr Lys Arg Val Val Asp Met
    290                 295                 300

Lys Trp Gly Ser Phe Pro Ile Phe Gln
305                 310
```

```
<210> SEQ ID NO 40
<211> LENGTH: 942
<212> TYPE: DNA
```

<213> ORGANISM: Artificial Sequence
<220> FEATURE:
<223> OTHER INFORMATION: Synthetic gene derived from Saccharomyces
      cerevisiae YPR1 putative reductase, having glycine codon inserted
      after the initiating methionine codon

<400> SEQUENCE: 40

```
atgggtccgg caactctgaa gaactcttct gcaactctga aactgaacac tggtgcatct      60
atcccggttc tgggtttcgg tacttggcgt tctgttgaca caacggtta ccactccgtt     120
atcgcagcac tgaaagcagg ttaccgtcac atcgacgcag cagcaatcta cctgaacgaa     180
gaagaagtag gtcgtgcaat caaagactcc ggtgttccgc gtgaagaaat ctttatcact     240
actaaactgt ggggtactga acagcgtgac ccggaagcag cactgaacaa atctctgaaa     300
cgtctgggtc tggactacgt agacctgtac ctgatgcact ggccggtacc gctgaaaact     360
gaccgtgtta ctgatggtaa cgttctgtgt attccgactc tggaagacgg tactgtagac     420
atcgacacta aggaatggaa cttcatcaag acttgggaac tgatgcagga actgccgaaa     480
actggtaaaa ctaaagcagt aggtgtttcc aacttctcta tcaacaacat caagaactg     540
ctggaatctc cgaacaacaa agtagtaccg gcaactaacc agatcgaaat ccacccgctg     600
ctgccgcagg acgaactgat cgcattctgc aaagagaaag gtatcgtagt agaagcatac     660
tctccgttcg gctctgcaaa cgcaccgctg ctgaaagaac aggcaatcat cgacatggca     720
aagaaacacg gtgtagaacc ggcacagctg atcatctctt ggtctatcca gcgtggttac     780
gtagtactgg caaaatctgt aaacccggaa cgtatcgtat ctaacttcaa aatcttcact     840
ctgccggaag acgacttcaa aactatctct aacctgtcca agttcacgg tactaaacgt     900
gtagtagaca tgaaatgggg ttcttttccc g atcttccagt aa                      942
```

<210> SEQ ID NO 41
<211> LENGTH: 939
<212> TYPE: DNA
<213> ORGANISM: Saccharomyces cerevisiae

<400> SEQUENCE: 41

```
atgcctgcta ctttacatga ttctacgaaa atcctttctc taaatactgg agcccaaatc      60
cctcaaatag gtttaggtac gtggcagtcg aaagagaacg atgcttataa ggctgtttta     120
accgctttga agatggcta ccgacacatt gatactgctg ctatttaccg taatgaagac     180
caagtcggtc aagccatcaa ggattcaggt gttcctcggg aagaaatctt tgttactaca     240
aagttatggt gtacacaaca ccacgaacct gaagtagcgc tggatcaatc actaaagagg     300
ttaggattgg actacgtaga cttatatttg atgcattggc ctgccagatt agatccagcc     360
tacatcaaaa atgaagacat cttgagtgtg ccaacaaaga aggatggttc tcgtgcagtg     420
gatatcacca attggaattt catcaaaacc tgggaattaa tgcaggaact accaaagact     480
ggtaaaacta aggccgttgg agtctccaac ttttctataa ataacctgaa agatctatta     540
gcatctcaag gtaataagct tacgccagct gctaaccaag tcgaaataca tccattacta     600
cctcaagacg aattgattaa tttttgtaaa agtaaaggca ttgtggttga agcttattct     660
ccgttaggta gtaccgatgc tccactattg aaggaaccgg ttatccttga aattgcgaag     720
aaaaataacg ttcaacccgg acacgttgtt attagctggc acgtccaaag aggttatgtt     780
gtcttgccaa aatctgtgaa tcccgatcga atcaaaacga acaggaaaat atttactttg     840
tctactgagg actttgaagc tatcaataac atatcgaagg aaaagggcga aaaaggggtt     900
gtacatccaa attggtctcc tttcgaagta ttcaagtaa                             939
```

<210> SEQ ID NO 42
<211> LENGTH: 312
<212> TYPE: PRT
<213> ORGANISM: Saccharomyces cerevisiae

<400> SEQUENCE: 42

```
Met Pro Ala Thr Leu His Asp Ser Thr Lys Ile Leu Ser Leu Asn Thr
  1               5                  10                  15

Gly Ala Gln Ile Pro Gln Ile Gly Leu Gly Thr Trp Gln Ser Lys Glu
             20                  25                  30

Asn Asp Ala Tyr Lys Ala Val Leu Thr Ala Leu Lys Asp Gly Tyr Arg
         35                  40                  45

His Ile Asp Thr Ala Ala Ile Tyr Arg Asn Glu Asp Gln Val Gly Gln
     50                  55                  60

Ala Ile Lys Asp Ser Gly Val Pro Arg Glu Glu Ile Phe Val Thr Thr
 65                  70                  75                  80

Lys Leu Trp Cys Thr Gln His His Glu Pro Glu Val Ala Leu Asp Gln
                 85                  90                  95

Ser Leu Lys Arg Leu Gly Leu Asp Tyr Val Asp Leu Tyr Leu Met His
            100                 105                 110

Trp Pro Ala Arg Leu Asp Pro Ala Tyr Ile Lys Asn Glu Asp Ile Leu
        115                 120                 125

Ser Val Pro Thr Lys Lys Asp Gly Ser Arg Ala Val Asp Ile Thr Asn
130                 135                 140

Trp Asn Phe Ile Lys Thr Trp Glu Leu Met Gln Glu Leu Pro Lys Thr
145                 150                 155                 160

Gly Lys Thr Lys Ala Val Gly Val Ser Asn Phe Ser Ile Asn Asn Leu
                165                 170                 175

Lys Asp Leu Leu Ala Ser Gln Gly Asn Lys Leu Thr Pro Ala Ala Asn
            180                 185                 190

Gln Val Glu Ile His Pro Leu Leu Pro Gln Asp Glu Leu Ile Asn Phe
        195                 200                 205

Cys Lys Ser Lys Gly Ile Val Val Glu Ala Tyr Ser Pro Leu Gly Ser
    210                 215                 220

Thr Asp Ala Pro Leu Leu Lys Glu Pro Val Ile Leu Glu Ile Ala Lys
225                 230                 235                 240

Lys Asn Asn Val Gln Pro Gly His Val Val Ile Ser Trp His Val Gln
                245                 250                 255

Arg Gly Tyr Val Val Leu Pro Lys Ser Val Asn Pro Asp Arg Ile Lys
            260                 265                 270

Thr Asn Arg Lys Ile Phe Thr Leu Ser Thr Glu Asp Phe Glu Ala Ile
        275                 280                 285

Asn Asn Ile Ser Lys Glu Lys Gly Glu Lys Arg Val Val His Pro Asn
    290                 295                 300

Trp Ser Pro Phe Glu Val Phe Lys
305                 310
```

<210> SEQ ID NO 43
<211> LENGTH: 942
<212> TYPE: DNA
<213> ORGANISM: Artificial Sequence
<220> FEATURE:
<223> OTHER INFORMATION: Synthetic gene derived from Saccharomyces
      cerevisiae GCY1 reductase, having numerous codons replaced with
      others encoding the same amino acids to reduce the free energy of
      folding, and a ggc insertion after the initiating atg

<400> SEQUENCE: 43

```
atgggcccag ctactctgca cgactctacc aaaattctgt ctctgaacac cggtgctcaa      60
atcccgcaaa tcggcctggg tacttggcaa tctaaagaaa acgacgcata caaggctgtt     120
ctgactgctc tgaaggatgg ctatcgtcac attgatactg ctgctattta tcgtaacgag     180
gaccaggtag gtcaggcaat caaggactct ggcgttccgc gtgaggaaat cttcgtaact     240
accaaactgt ggtgcactca gcatcatgaa ccggaagtag cactggatca atctctgaag     300
cgtctgggtc tggactatgt tgatctgtac ctgatgcatt ggccggcgcg cctggaccca     360
gcgtatatta aaaacgaaga tatcctgtct gttccgacta agaaagacgg ctctcgtgct     420
gttgacatca ctaactggaa cttcatcaag acctgggaac tgatgcagga actgccgaag     480
actggtaaaa ctaaagctgt tggcgtatct aacttctcca tcaacaacct gaaggacctg     540
ctggcatccc agggcaacaa gctgactccg gctgctaacc aagtagagat ccacccgctg     600
ctgccgcagg acgaactgat caacttctgt aaatctaaag gcattgtagt tgaagcatat     660
tctccgctgg ttctaccga tgcgccactg ctgaaagagc cggtaatcct ggagatcgcg     720
aagaaaaaca acgtacaacc aggtcatgta gtaatctctt ggcacgtaca gcgcggctac     780
gtagttctgc cgaagtctgt aaacccggat cgtatcaaaa ctaaccgtaa aatctttacc     840
ctgtccaccg aagatttcga agcaatcaac aacatctcca aggaaaaggg cgagaaacgt     900
gtagttcacc caaactggtc cccgtttgaa gtattcaagt aa                        942
```

<210> SEQ ID NO 44
<211> LENGTH: 313
<212> TYPE: PRT
<213> ORGANISM: Artificial Sequence
<220> FEATURE:
<223> OTHER INFORMATION: Synthetic protein derived from Saccharomyces cerevisiae GCY1 reductase, having a glycine inserted at position 2 in the amino acid sequence

<400> SEQUENCE: 44

```
Met Gly Pro Ala Thr Leu His Asp Ser Thr Lys Ile Leu Ser Leu Asn
1               5                   10                  15
Thr Gly Ala Gln Ile Pro Gln Ile Gly Leu Gly Thr Trp Gln Ser Lys
            20                  25                  30
Glu Asn Asp Ala Tyr Lys Ala Val Leu Thr Ala Leu Lys Asp Gly Tyr
        35                  40                  45
Arg His Ile Asp Thr Ala Ala Ile Tyr Arg Asn Glu Asp Gln Val Gly
    50                  55                  60
Gln Ala Ile Lys Asp Ser Gly Val Pro Arg Glu Glu Ile Phe Val Thr
65                  70                  75                  80
Thr Lys Leu Trp Cys Thr Gln His His Glu Pro Glu Val Ala Leu Asp
                85                  90                  95
Gln Ser Leu Lys Arg Leu Gly Leu Asp Tyr Val Asp Leu Tyr Leu Met
            100                 105                 110
His Trp Pro Ala Arg Leu Asp Pro Ala Tyr Ile Lys Asn Glu Asp Ile
        115                 120                 125
Leu Ser Val Pro Thr Lys Lys Asp Gly Ser Arg Ala Val Asp Ile Thr
    130                 135                 140
Asn Trp Asn Phe Ile Lys Thr Trp Glu Leu Met Gln Glu Leu Pro Lys
145                 150                 155                 160
Thr Gly Lys Thr Lys Ala Val Gly Val Ser Asn Phe Ser Ile Asn Asn
                165                 170                 175
```

Leu Lys Asp Leu Leu Ala Ser Gln Gly Asn Lys Leu Thr Pro Ala Ala
            180                 185                 190

Asn Gln Val Glu Ile His Pro Leu Pro Gln Asp Glu Leu Ile Asn
        195                 200                 205

Phe Cys Lys Ser Lys Gly Ile Val Val Glu Ala Tyr Ser Pro Leu Gly
        210                 215                 220

Ser Thr Asp Ala Pro Leu Leu Lys Glu Pro Val Ile Leu Glu Ile Ala
225                 230                 235                 240

Lys Lys Asn Asn Val Gln Pro Gly His Val Val Ile Ser Trp His Val
                245                 250                 255

Gln Arg Gly Tyr Val Val Leu Pro Lys Ser Val Asn Pro Asp Arg Ile
            260                 265                 270

Lys Thr Asn Arg Lys Ile Phe Thr Leu Ser Thr Glu Asp Phe Glu Ala
        275                 280                 285

Ile Asn Asn Ile Ser Lys Glu Lys Gly Glu Lys Arg Val Val His Pro
        290                 295                 300

Asn Trp Ser Pro Phe Glu Val Phe Lys
305                 310

<210> SEQ ID NO 45
<211> LENGTH: 1029
<212> TYPE: DNA
<213> ORGANISM: Saccharomyces cerevisiae

<400> SEQUENCE: 45
atgtcagttt tcgtttcagg tgctaacggg ttcattgccc aacacattgt cgatctcctg      60
ttgaaggaag actataaggt catcggttct gccagaagtc aagaaaaggc cgagaattta     120
acggaggcct ttggtaacaa cccaaaattc tccatggaag ttgtcccaga catatctaag     180
ctggacgcat tgaccatgt tttccaaaag cacggcaagg atatcaagat agttctacat     240
acggcctctc cattctgctt tgatatcact gacagtgaac gcgatttatt aattcctgct     300
gtgaacggtg ttaagggaat tctccactca attaaaaaat acgccgctga ttctgtagaa     360
cgtgtagttc tcacctcttc ttatgcagct gtgttcgata tggcaaaaga aaacgataag     420
tctttaacat ttaacgaaga atcctggaac ccagctacct gggagagttg ccaaagtgac     480
ccagttaacg cctactgtgg ttctaagaag tttgctgaaa agcagcttgg gaatttcta     540
gaggagaata gagactctgt aaaattcgaa ttaactgccg ttaacccagt ttacgttttt     600
ggtccgcaaa tgtttgacaa agatgtgaaa aaacacttga acacatcttg cgaactcgtc     660
aacagcttga tgcatttatc accagaggac aagataccgg aactatttgg tggatacatt     720
gatgttcgtg atgttgcaaa ggctcattta gttgccttcc aaaagaggga acaattggt     780
caaagactaa tcgtatcgga ggccagattt actatgcagg atgttctcga tatccttaac     840
gaagacttcc ctgttctaaa aggcaatatt ccagtgggga accaggttc tggtgctacc     900
cataacaccc ttggtgctac tcttgataat aaaaagagta agaaattgtt aggtttcaag     960
ttcaggaact tgaaagagac cattgacgac actgcctccc aaattttaaa atttgagggc    1020
agaatataa                                                              1029

<210> SEQ ID NO 46
<211> LENGTH: 342
<212> TYPE: PRT
<213> ORGANISM: Saccharomyces cerevisiae

<400> SEQUENCE: 46

```
Met Ser Val Phe Val Ser Gly Ala Asn Gly Phe Ile Ala Gln His Ile
1               5                   10                  15

Val Asp Leu Leu Lys Glu Asp Tyr Lys Val Ile Gly Ser Ala Arg
            20                  25                  30

Ser Gln Glu Lys Ala Glu Asn Leu Thr Glu Ala Phe Gly Asn Asn Pro
        35                  40                  45

Lys Phe Ser Met Glu Val Val Pro Asp Ile Ser Lys Leu Asp Ala Phe
    50                  55                  60

Asp His Val Phe Gln Lys His Gly Lys Asp Lys Ile Val Leu His
65                  70                  75                  80

Thr Ala Ser Pro Phe Cys Phe Asp Ile Thr Asp Ser Glu Arg Asp Leu
                85                  90                  95

Leu Ile Pro Ala Val Asn Gly Val Lys Gly Ile Leu His Ser Ile Lys
            100                 105                 110

Lys Tyr Ala Ala Asp Ser Val Glu Arg Val Val Leu Thr Ser Ser Tyr
        115                 120                 125

Ala Ala Val Phe Asp Met Ala Lys Glu Asn Asp Lys Ser Leu Thr Phe
130                 135                 140

Asn Glu Glu Ser Trp Asn Pro Ala Thr Trp Glu Ser Cys Gln Ser Asp
145                 150                 155                 160

Pro Val Asn Ala Tyr Cys Gly Ser Lys Lys Phe Ala Glu Lys Ala Ala
                165                 170                 175

Trp Glu Phe Leu Glu Glu Asn Arg Asp Ser Val Lys Phe Glu Leu Thr
            180                 185                 190

Ala Val Asn Pro Val Tyr Val Phe Gly Pro Gln Met Phe Asp Lys Asp
        195                 200                 205

Val Lys Lys His Leu Asn Thr Ser Cys Glu Leu Val Asn Ser Leu Met
    210                 215                 220

His Leu Ser Pro Glu Asp Lys Ile Pro Glu Leu Phe Gly Gly Tyr Ile
225                 230                 235                 240

Asp Val Arg Asp Val Ala Lys Ala His Leu Val Ala Phe Gln Lys Arg
                245                 250                 255

Glu Thr Ile Gly Gln Arg Leu Ile Val Ser Glu Ala Arg Phe Thr Met
            260                 265                 270

Gln Asp Val Leu Asp Ile Leu Asn Glu Asp Phe Pro Val Leu Lys Gly
        275                 280                 285

Asn Ile Pro Val Gly Lys Pro Gly Ser Gly Ala Thr His Asn Thr Leu
    290                 295                 300

Gly Ala Thr Leu Asp Asn Lys Lys Ser Lys Lys Leu Leu Gly Phe Lys
305                 310                 315                 320

Phe Arg Asn Leu Lys Glu Thr Ile Asp Asp Thr Ala Ser Gln Ile Leu
                325                 330                 335

Lys Phe Glu Gly Arg Ile
            340

<210> SEQ ID NO 47
<211> LENGTH: 1032
<212> TYPE: DNA
<213> ORGANISM: Artificial Sequence
<220> FEATURE:
<223> OTHER INFORMATION: Synthetic gene derived from Saccharomyces
      cerevisiae GRE2 reductase, having numerous codons replaced with
      others encoding the same amino acids to reduce the free energy of
      folding, and a ggc insertion at position 2 in the amino acid
      sequence
```

<400> SEQUENCE: 47

```
atgggctctg tatttgtatc tggcgctaac ggttttatcg ctcaacacat cgtcgatctg      60
ctgctgaaag aagattacaa agttatcggt tccgcacgtt cccaggaaaa agctgaaaac     120
ctgactgaag catttggtaa caacccgaag ttctctatgg aagtagtacc ggacatttct     180
aaactggacg cattcgacca cgtattccaa aagcacggta aggatatcaa gatcgtactg     240
cacactgcat ctccattctg ttttgacatc actgattctg agcgcgacct gctgattccg     300
gctgttaacg gtgttaaagg tattctgcac tctattaaga aatatgctgc tgattccgta     360
gaacgcgtag ttctgacttc ctcttatgct gcagtattcg atatggctaa agagaacgac     420
aaatccctga cttttaacga agaatcttgg aacccggcta cctgggaatc ttgccagtct     480
gacccggtta acgcttattg tggctctaag aagtttgctg aaaaagctgc ttgggaattc     540
ctggaagaaa accgtgactc tgtaaagttc gagctgaccg ctgtaaaccc ggtatacgtt     600
tttggcccgc agatgttcga taagatgta aagaagcacc tgaacacttc ctgtgaactg     660
gtaaactctc tgatgcacct gtctccagaa gataaaatcc cggagctgtt cggcggttac     720
atcgacgttc gtgacgtagc aaaagcacat ctggtagctt tccagaagcg tgagactatc     780
ggccagcgtc tgattgtttc cgaggctcgt ttcaccatgc aggatgttct ggatattctg     840
aacgaagact tcccggtact gaaggtaac attccggtgg gtaaaccagg ctctggtgca     900
actcataaca ctctgggtgc aactctggat aacaagaagt ctaagaaact gctgggtttt     960
aaattccgta acctgaaaga aactattgac gacactgcat ctcagatcct gaaattcgaa    1020
ggtcgcatct aa                                                         1032
```

<210> SEQ ID NO 48
<211> LENGTH: 343
<212> TYPE: PRT
<213> ORGANISM: Artificial Sequence
<220> FEATURE:
<223> OTHER INFORMATION: Synthetic protein derived from Saccharomyces cerevisiae Gre2 reductase, having a glycine inserted at position 2 in the amino acid sequence

<400> SEQUENCE: 48

```
Met Gly Ser Val Phe Val Ser Gly Ala Asn Gly Phe Ile Ala Gln His
1               5                   10                  15

Ile Val Asp Leu Leu Lys Glu Asp Tyr Lys Val Ile Gly Ser Ala
            20                  25                  30

Arg Ser Gln Glu Lys Ala Glu Asn Leu Thr Glu Ala Phe Gly Asn Asn
        35                  40                  45

Pro Lys Phe Ser Met Glu Val Val Pro Asp Ile Ser Lys Leu Asp Ala
    50                  55                  60

Phe Asp His Val Phe Gln Lys His Gly Lys Asp Ile Lys Ile Val Leu
65                  70                  75                  80

His Thr Ala Ser Pro Phe Cys Phe Asp Ile Thr Asp Ser Glu Arg Asp
                85                  90                  95

Leu Leu Ile Pro Ala Val Asn Gly Val Lys Gly Ile Leu His Ser Ile
            100                 105                 110

Lys Lys Tyr Ala Ala Asp Ser Val Glu Arg Val Leu Thr Ser Ser
        115                 120                 125

Tyr Ala Ala Val Phe Asp Met Ala Lys Glu Asn Asp Lys Ser Leu Thr
    130                 135                 140

Phe Asn Glu Glu Ser Trp Asn Pro Ala Thr Trp Glu Ser Cys Gln Ser
145                 150                 155                 160
```

```
Asp Pro Val Asn Ala Tyr Cys Gly Ser Lys Lys Phe Ala Glu Lys Ala
                165                 170                 175

Ala Trp Glu Phe Leu Glu Glu Asn Arg Asp Ser Val Lys Phe Glu Leu
            180                 185                 190

Thr Ala Val Asn Pro Val Tyr Val Phe Gly Pro Gln Met Phe Asp Lys
        195                 200                 205

Asp Val Lys Lys His Leu Asn Thr Ser Cys Glu Leu Val Asn Ser Leu
    210                 215                 220

Met His Leu Ser Pro Glu Asp Lys Ile Pro Glu Leu Phe Gly Tyr
225                 230                 235                 240

Ile Asp Val Arg Asp Val Ala Lys Ala His Leu Val Ala Phe Gln Lys
                245                 250                 255

Arg Glu Thr Ile Gly Gln Arg Leu Ile Val Ser Glu Ala Arg Phe Thr
            260                 265                 270

Met Gln Asp Val Leu Asp Ile Leu Asn Glu Asp Phe Pro Val Leu Lys
        275                 280                 285

Gly Asn Ile Pro Val Gly Lys Pro Gly Ser Gly Ala Thr His Asn Thr
    290                 295                 300

Leu Gly Ala Thr Leu Asp Asn Lys Lys Ser Lys Lys Leu Leu Gly Phe
305                 310                 315                 320

Lys Phe Arg Asn Leu Lys Glu Thr Ile Asp Asp Thr Ala Ser Gln Ile
                325                 330                 335

Leu Lys Phe Glu Gly Arg Ile
            340
```

<210> SEQ ID NO 49
<211> LENGTH: 987
<212> TYPE: DNA
<213> ORGANISM: Artificial Sequence
<220> FEATURE:
<223> OTHER INFORMATION: Essentially encodes the native GRE3 reductase
      gene from Saccharomyces cerevisiae, but has a codon for isoleucine
      inserted after the initiating methionine codon to incorporate a
      restriction site

<400> SEQUENCE: 49

```
atgatttctt cactggttac tcttaataac ggtctgaaaa tgccctagt cggcttaggg    60
tgctggaaaa ttgacaaaaa agtctgtgcg aatcaaattt atgaagctat caaattaggc   120
taccgtttat tcgatggtgc ttgcgactac ggcaacgaaa aggaagttgg tgaaggtatc   180
aggaaagcca tctccgaagg tcttgtttct agaaaggata tatttgttgt ttcaaagtta   240
tggaacaatt ttcaccatcc tgatcatgta aaattagctt taagaagac cttaagcgat    300
atgggacttg attatttaga cctgtattat attcacttcc caatcgcctt caaatatgtt   360
ccatttgaag agaaataccc tccaggattc tatacgggcg cagatgacga agaaaaggt    420
cacatcaccg aagcacatgt accaatcata gatacgtacc gggctctgga agaatgtgtt   480
gatgaaggct tgattaagtc tattggtgtt ccaactttc agggaagctt gattcaagat   540
ttattacgtg gttgtagaat caagcccgtg gctttgcaaa ttgaacacca tccttatttg   600
actcaagaac acctagttga gttttgtaaa ttacacgata tccaagtagt tgcttactcc   660
tccttcggtc ctcaatcatt cattgagatg gacttacagt tggcaaaaac cacgccaact   720
ctgttcgaga tgatgtaat caagaaggtc tcacaaaacc atccaggcag taccacttcc   780
caagtattgc ttagatgggc aactcagaga ggcattgccg tcattccaaa atcttccaag   840
aaggaaaggt tacttggcaa cctagaaatc gaaaaaaagt tcacttaac ggagcaagaa    900
```

```
ttgaaggata tttctgcact aaatgccaac atcagattta atgatccatg gacctggttg    960
gatggtaaat tccccacttt tgcctga                                         987
```

<210> SEQ ID NO 50
<211> LENGTH: 328
<212> TYPE: PRT
<213> ORGANISM: Artificial Sequence
<220> FEATURE:
<223> OTHER INFORMATION: Essentially encodes the native GRE3 reductase
    protein from Saccharomyces cerevisiae, but has an isoleucine
    inserted after the initiating methionine

<400> SEQUENCE: 50

```
Met Ile Ser Ser Leu Val Thr Leu Asn Asn Gly Leu Lys Met Pro Leu
1               5                   10                  15

Val Gly Leu Gly Cys Trp Lys Ile Asp Lys Lys Val Cys Ala Asn Gln
            20                  25                  30

Ile Tyr Glu Ala Ile Lys Leu Gly Tyr Arg Leu Phe Asp Gly Ala Cys
        35                  40                  45

Asp Tyr Gly Asn Glu Lys Glu Val Gly Glu Gly Ile Arg Lys Ala Ile
50                  55                  60

Ser Glu Gly Leu Val Ser Arg Lys Asp Ile Phe Val Val Ser Lys Leu
65                  70                  75                  80

Trp Asn Asn Phe His His Pro Asp His Val Lys Leu Ala Leu Lys Lys
                85                  90                  95

Thr Leu Ser Asp Met Gly Leu Asp Tyr Leu Asp Leu Tyr Tyr Ile His
            100                 105                 110

Phe Pro Ile Ala Phe Lys Tyr Val Pro Phe Glu Glu Lys Tyr Pro Pro
        115                 120                 125

Gly Phe Tyr Thr Gly Ala Asp Asp Glu Lys Lys Gly His Ile Thr Glu
130                 135                 140

Ala His Val Pro Ile Ile Asp Thr Tyr Arg Ala Leu Glu Glu Cys Val
145                 150                 155                 160

Asp Glu Gly Leu Ile Lys Ser Ile Gly Val Ser Asn Phe Gln Gly Ser
                165                 170                 175

Leu Ile Gln Asp Leu Leu Arg Gly Cys Arg Ile Lys Pro Val Ala Leu
            180                 185                 190

Gln Ile Glu His His Pro Tyr Leu Thr Gln Glu His Leu Val Glu Phe
        195                 200                 205

Cys Lys Leu His Asp Ile Gln Val Val Ala Tyr Ser Ser Phe Gly Pro
210                 215                 220

Gln Ser Phe Ile Glu Met Asp Leu Gln Leu Ala Lys Thr Thr Pro Thr
225                 230                 235                 240

Leu Phe Glu Asn Asp Val Ile Lys Lys Val Ser Gln Asn His Pro Gly
                245                 250                 255

Ser Thr Thr Ser Gln Val Leu Leu Arg Trp Ala Thr Gln Arg Gly Ile
            260                 265                 270

Ala Val Ile Pro Lys Ser Ser Lys Glu Arg Leu Leu Gly Asn Leu
        275                 280                 285

Glu Ile Glu Lys Lys Phe Thr Leu Thr Glu Gln Glu Leu Lys Asp Ile
290                 295                 300

Ser Ala Leu Asn Ala Asn Ile Arg Phe Asn Asp Pro Trp Thr Trp Leu
305                 310                 315                 320

Asp Gly Lys Phe Pro Thr Phe Ala
                325
```

<210> SEQ ID NO 51
<211> LENGTH: 987
<212> TYPE: DNA
<213> ORGANISM: Artificial Sequence
<220> FEATURE:
<223> OTHER INFORMATION: Synthetic gene derived from Saccharomyces cerevisiae GRE3 reductase, having numerous codons replaced with others encoding the same amino acids to reduce the free energy of folding, and a ggc codon insertion after the initiating atg

<400> SEQUENCE: 51

```
atgggctctt ctctggtaac tctgaacaac ggtctgaaaa tgccgctggt aggcctgggc      60
tgctggaaaa tcgataagaa agtatgtgct aaccaaattt atgaggctat caaactgggc     120
tatcgcctgt tcgacggtgc ttgcgactat ggtaacgaga aggaagttgg tgaaggcatc     180
cgtaaagcta tctctgaagg tctggtatct cgtaaggata tctttgtagt atctaagctg     240
tggaacaact tcatcaccc ggatcacgta aaactggcac tgaagaaaac cctgtctgat     300
atgggtctgg attatctgga tctgtactat atccactttc cgatcgcatt taaatacgta     360
ccgttcgaag aaaaatatcc gccgggcttt tacactggtg cagacgacga aagaagggt     420
cacatcactg aagctcacgt accgatcatc gacacttacc gtgctctgga ggaatgtgta     480
gacgaaggtc tgatcaaatc tatcggtgta tctaacttcc agggttctct gatccaggat     540
ctgctgcgtg gttgccgtat caagccggtt gctctgcaaa ttgaacacca cccgtacctg     600
acccaggaac acctggttga attctgcaaa ctgcacgata tccaagtagt agcatactct     660
tctttcggtc cgcagtcttt catcgaaatg gacctgcagc tggctaagac cacccccgact    720
ctgttcgaaa acgacgtaat caagaaagta tctcagaacc accgggctc tactacctct     780
caggtactgc tgcgttgggc tactcagcgt ggcatcgctg ttatcccgaa atcttctaag     840
aaagaacgtc tgctgggtaa cctggaaatc gaaaagaaat tcactctgac cgaacaggaa     900
ctgaaagata tctctgctct gaacgctaac atccgtttca cgatccgtg gacctggctg     960
gatggtaaat tcccgacttt cgcttaa                                         987
```

<210> SEQ ID NO 52
<211> LENGTH: 328
<212> TYPE: PRT
<213> ORGANISM: Artificial Sequence
<220> FEATURE:
<223> OTHER INFORMATION: Synthetic protein derived from Saccharomyces cerevisiae Gre3 reductase, having a glycine inserted at position 2 in the amino acid sequence

<400> SEQUENCE: 52

```
Met Gly Ser Ser Leu Val Thr Leu Asn Asn Gly Leu Lys Met Pro Leu
 1               5                  10                  15

Val Gly Leu Gly Cys Trp Lys Ile Asp Lys Lys Val Cys Ala Asn Gln
             20                  25                  30

Ile Tyr Glu Ala Ile Lys Leu Gly Tyr Arg Leu Phe Asp Gly Ala Cys
         35                  40                  45

Asp Tyr Gly Asn Glu Lys Glu Val Gly Glu Gly Ile Arg Lys Ala Ile
     50                  55                  60

Ser Glu Gly Leu Val Ser Arg Lys Asp Ile Phe Val Val Ser Lys Leu
 65                  70                  75                  80

Trp Asn Asn Phe His His Pro Asp His Val Lys Leu Ala Leu Lys Lys
                 85                  90                  95

Thr Leu Ser Asp Met Gly Leu Asp Tyr Leu Asp Leu Tyr Tyr Ile His
```

```
                100             105             110
Phe Pro Ile Ala Phe Lys Tyr Val Pro Phe Glu Glu Lys Tyr Pro Pro
            115                 120                 125

Gly Phe Tyr Thr Gly Ala Asp Asp Glu Lys Lys Gly His Ile Thr Glu
130             135                 140

Ala His Val Pro Ile Ile Asp Thr Tyr Arg Ala Leu Glu Glu Cys Val
145                 150                 155                 160

Asp Glu Gly Leu Ile Lys Ser Ile Gly Val Ser Asn Phe Gln Gly Ser
                165                 170                 175

Leu Ile Gln Asp Leu Leu Arg Gly Cys Arg Ile Lys Pro Val Ala Leu
            180                 185                 190

Gln Ile Glu His His Pro Tyr Leu Thr Gln Glu His Leu Val Glu Phe
        195                 200                 205

Cys Lys Leu His Asp Ile Gln Val Val Ala Tyr Ser Ser Phe Gly Pro
210                 215                 220

Gln Ser Phe Ile Glu Met Asp Leu Gln Leu Ala Lys Thr Thr Pro Thr
225                 230                 235                 240

Leu Phe Glu Asn Asp Val Ile Lys Lys Val Ser Gln Asn His Pro Gly
                245                 250                 255

Ser Thr Thr Ser Gln Val Leu Leu Arg Trp Ala Thr Gln Arg Gly Ile
            260                 265                 270

Ala Val Ile Pro Lys Ser Ser Lys Glu Arg Leu Leu Gly Asn Leu
        275                 280                 285

Glu Ile Glu Lys Lys Phe Thr Leu Thr Glu Gln Glu Leu Lys Asp Ile
    290                 295                 300

Ser Ala Leu Asn Ala Asn Ile Arg Phe Asn Asp Pro Trp Thr Trp Leu
305                 310                 315                 320

Asp Gly Lys Phe Pro Thr Phe Ala
                325

<210> SEQ ID NO 53
<211> LENGTH: 1461
<212> TYPE: DNA
<213> ORGANISM: Sus scrofa

<400> SEQUENCE: 53
atgaatgcca gcgatttccg tcgacgcggc aaagaaatgg tggattacat ggcggattac      60
ctggaaggca tcgaaggtcg tcaggtgtac ccggatgtgc agccggggta cctgcgtccg     120
ctgatcccgg cgaccgcccc gcaggaaccg gataccttcg aagatatcct gcaggatgtg     180
gaaaaaatca tcatgccggg ggtgaccaca tggcacagcc gtacttcttc gcgtacttc     240 ccgaccgcca gcagctaccc ggcgatgctg cggatatgcg tgtgcggtgc gatcggatgc     300
atcggtttca gctgggcggc tagcccggcg tgcaccgaac tcgagaccgt gatgatggat     360
tggctgggca aaatgctcca gcttccggaa gcgttcctgg cgggcgaagc cggtgaaggc     420
ggcggcgtga tccagggtag cgccagcgaa gccaccctgg tggcgctgct ggcggcgcgt     480
accaaagtgg tgcgacgtct gcaagcggcg agcccgggcc tgacccaggg cgcggtgctg     540
gaaaaactag tggcgtacgc gagtgatcag gcgcacagca gcgtggaacg tgccggcctg     600
atcggcggcg tgaaactgaa agcgatcccg agcgatggca aattcgcgat gcgtgcgagc     660
gcgctgcagg aggccctgga gagagacaag gctgccggcc tgattccttt cttcgtggtg     720
gctacgctgg ggaccacatc gtgctgctcc tttgacaatc tcttagaagt gggacccatc     780
tgtcacgaag aggacatatg gctgcacgtg gatgctgcct acgcaggcag tgccttcatc     840
```

```
tgccctgagt tccggcacct gctgaatgga gtggagtttg cagattcatt taactttaat    900
ccccacaaat ggctcttggt gaattttgac tgctcggcta tgtgggtgaa aaggagaacg    960
gacctgactg gagccttcaa attggacccc gtgtacttaa agcacagcca ccagggctcg   1020
gggcttatca cggactacag gcactggcag ctgccactgg gtcggcgatt ccggtccctg   1080
aaaatgtggt ttgtttttag gatgtacgga gtcaagggac tgcaggccta tatccgcaag   1140
cacgtgcagc tgtctcatga gtttgaggca tttgtgcttc aggatccacg ctttgaagtc   1200
tgtgccgaag tcaccctggg gctggtgtgt tccggctga agggctccga cggactgaat   1260
gaagcgcttc tggaaaggat aaacagcgcc aggaaaatcc acttggttcc ctgtcgcctg   1320
aggggccagt tcgtgctgcg gttcgccatc tgctcgcgca aggtggagtc gggccacgtg   1380
cggctggcct gggagcacat ccgagggctg gcggccgagc tgctggccgc ggaggaggga   1440
aaggcagaga tcaaaagttg a                                              1461
```

<210> SEQ ID NO 54
<211> LENGTH: 486
<212> TYPE: PRT
<213> ORGANISM: Sus scrofa

<400> SEQUENCE: 54

```
Met Asn Ala Ser Asp Phe Arg Arg Arg Gly Lys Glu Met Val Asp Tyr
1               5                   10                  15

Met Ala Asp Tyr Leu Glu Gly Ile Glu Gly Arg Gln Val Tyr Pro Asp
            20                  25                  30

Val Gln Pro Gly Tyr Leu Arg Pro Leu Ile Pro Ala Thr Ala Pro Gln
        35                  40                  45

Glu Pro Asp Thr Phe Glu Asp Ile Leu Gln Asp Val Glu Lys Ile Ile
    50                  55                  60

Met Pro Gly Val Thr His Trp His Ser Pro Tyr Phe Phe Ala Tyr Phe
65                  70                  75                  80

Pro Thr Ala Ser Ser Tyr Pro Ala Met Leu Ala Asp Met Leu Cys Gly
                85                  90                  95

Ala Ile Gly Cys Ile Gly Phe Ser Trp Ala Ala Ser Pro Ala Cys Thr
            100                 105                 110

Glu Leu Glu Thr Val Met Met Asp Trp Leu Gly Lys Met Leu Gln Leu
        115                 120                 125

Pro Glu Ala Phe Leu Ala Gly Glu Ala Gly Glu Gly Gly Val Ile
    130                 135                 140

Gln Gly Ser Ala Ser Glu Ala Thr Leu Val Ala Leu Leu Ala Ala Arg
145                 150                 155                 160

Thr Lys Val Val Arg Arg Leu Gln Ala Ala Ser Pro Gly Leu Thr Gln
                165                 170                 175

Gly Ala Val Leu Glu Lys Leu Val Ala Tyr Ala Ser Asp Gln Ala His
            180                 185                 190

Ser Ser Val Glu Arg Ala Gly Leu Ile Gly Gly Val Lys Leu Lys Ala
        195                 200                 205

Ile Pro Ser Asp Gly Lys Phe Ala Met Arg Ala Ser Ala Leu Gln Glu
    210                 215                 220

Ala Leu Glu Arg Asp Lys Ala Ala Gly Leu Ile Pro Phe Phe Val Val
225                 230                 235                 240

Ala Thr Leu Gly Thr Thr Ser Cys Cys Ser Phe Asp Asn Leu Leu Glu
                245                 250                 255
```

```
Val Gly Pro Ile Cys His Glu Glu Asp Ile Trp Leu His Val Asp Ala
            260                 265                 270

Ala Tyr Ala Gly Ser Ala Phe Ile Cys Pro Glu Phe Arg His Leu Leu
        275                 280                 285

Asn Gly Val Glu Phe Ala Asp Ser Phe Asn Phe Asn Pro His Lys Trp
    290                 295                 300

Leu Leu Val Asn Phe Asp Cys Ser Ala Met Trp Val Lys Arg Arg Thr
305                 310                 315                 320

Asp Leu Thr Gly Ala Phe Lys Leu Asp Pro Val Tyr Leu Lys His Ser
                325                 330                 335

His Gln Gly Ser Gly Leu Ile Thr Asp Tyr Arg His Trp Gln Leu Pro
            340                 345                 350

Leu Gly Arg Arg Phe Arg Ser Leu Lys Met Trp Phe Val Phe Arg Met
            355                 360                 365

Tyr Gly Val Lys Gly Leu Gln Ala Tyr Ile Arg Lys His Val Gln Leu
    370                 375                 380

Ser His Glu Phe Glu Ala Phe Val Leu Gln Asp Pro Arg Phe Glu Val
385                 390                 395                 400

Cys Ala Glu Val Thr Leu Gly Leu Val Cys Phe Arg Leu Lys Gly Ser
                405                 410                 415

Asp Gly Leu Asn Glu Ala Leu Leu Glu Arg Ile Asn Ser Ala Arg Lys
            420                 425                 430

Ile His Leu Val Pro Cys Arg Leu Arg Gly Gln Phe Val Leu Arg Phe
            435                 440                 445

Ala Ile Cys Ser Arg Lys Val Glu Ser Gly His Val Arg Leu Ala Trp
        450                 455                 460

Glu His Ile Arg Gly Leu Ala Ala Glu Leu Leu Ala Ala Glu Glu Gly
465                 470                 475                 480

Lys Ala Glu Ile Lys Ser
                485
```

<210> SEQ ID NO 55
<211> LENGTH: 1464
<212> TYPE: DNA
<213> ORGANISM: Artificial Sequence
<220> FEATURE:
<223> OTHER INFORMATION: Synthetic gene derived from Sus scrofa
    L-aromatic amino acid decarboxylase, having numerous codons
    replaced with others encoding the same amino acids to reduce free
    energy of folding, and a gly codon inserted after the initiating
    met codon

<400> SEQUENCE: 55

```
atgggtaacg cttccgattt ccgtcgtcgt ggcaaagaaa tggtagacta catggcagat    60
tatctggaag gtatcgaagg ccgtcaagtt tacccggacg ttcagccagg ctatctgcgt   120
ccgctcatcc agctaccgc accgcaagaa ccggacacct tgaagacat cctgcaagac   180 gtagaaaaga tcatcatgcc aggtgtaacc cactggcact ctccgtactt tttcgcatac   240
ttcccgactg catcctccta cccggctatg ctggctgaca tgctgtgtgg tgctatcggc   300
tgtatcggct tttcctgggc tgcatctccg gcatgcactg agctggaaac cgttatgatg   360
gattggctgg gtaaaatgct gcagctgcca gaggcatttc tggctggtga ggctggtgag   420
ggtggtggtg taattcaagg ctctgcgtcc gaagctactc tggttgctct gctggctgct   480
cgtactaaag ttgttcgtcg tctgcaagct gcatctccgg gtctgactca gggtgctgtt   540
ctggagaaac tggtagcgta tgcttctgat caggctcact cttccgttga gcgtgctggt   600
```

```
ctgattggtg gtgttaagct gaaagctatt ccgtccgatg gtaagttcgc tatgcgtgca    660
tccgctctgc aagaagctct ggaacgtgac aaagctgctg gtctgattcc gttcttcgtt    720
gttgctaccc tgggtactac ctcttgctgt tctttcgaca acctgctgga agttggtccg    780
atctgtcacg aggaggacat ctggctgcac gttgacgcag catatgctgg ctctgctttt    840
atctgtccgg aattccgtca cctgctgaac ggcgttgagt tcgctgattc tttcaacttc    900
aacccgcaca agtggctgct ggttaacttt gattgctcgg ctatgtgggt aaaacgtcgc    960
actgatctga ccggtgcatt taaactggac ccggtatatc tgaagcattc tcaccagggt   1020
tccggcctga ttaccgatta tcgtcattgg cagctgccgc tgggtcgtcg ttttcgttcg   1080
ctgaagatgt ggttcgtatt ccgtatgtac ggcgttaaag gtctgcaagc atacatccgt   1140
aaacacgttc aactgtcgca cgagttcgaa gctttcgtac tgcaggaccc gcgttttgaa   1200
gtttgcgctg aagttaccct gggcctggtt tgcttccgtc tgaagggttc tgatggtctg   1260
aacgaagctc tgctggagcg tattaactcg gctcgtaaaa tccacctggt tccgtgtcgt   1320
ctgcgtggtc agttcgttct gcgcttcgct atttgttcgc gtaaggtaga gtctggtcat   1380
gttcgtctgg catgggagca catccgtggt ctggctgctg aactgctggc tgctgaagaa   1440
ggtaaggctg aaatcaaatc ctaa                                           1464
```

<210> SEQ ID NO 56
<211> LENGTH: 487
<212> TYPE: PRT
<213> ORGANISM: Artificial Sequence
<220> FEATURE:
<223> OTHER INFORMATION: Synthetic protein derived from Sus scrofa
    L-aromatic amino acid decarboxylase, having a glycine inserted at
    position 2 in the amino acid sequence

<400> SEQUENCE: 56

```
Met Gly Asn Ala Ser Asp Phe Arg Arg Arg Gly Lys Glu Met Val Asp
1               5                   10                  15

Tyr Met Ala Asp Tyr Leu Glu Gly Ile Glu Gly Arg Gln Val Tyr Pro
            20                  25                  30

Asp Val Gln Pro Gly Tyr Leu Arg Pro Leu Ile Pro Ala Thr Ala Pro
        35                  40                  45

Gln Glu Pro Asp Thr Phe Glu Asp Ile Leu Gln Asp Val Glu Lys Ile
    50                  55                  60

Ile Met Pro Gly Val Thr His Trp His Ser Pro Tyr Phe Phe Ala Tyr
65                  70                  75                  80

Phe Pro Thr Ala Ser Ser Tyr Pro Ala Met Leu Ala Asp Met Leu Cys
                85                  90                  95

Gly Ala Ile Gly Cys Ile Gly Phe Ser Trp Ala Ala Ser Pro Ala Cys
            100                 105                 110

Thr Glu Leu Glu Thr Val Met Met Asp Trp Leu Gly Lys Met Leu Gln
        115                 120                 125

Leu Pro Glu Ala Phe Leu Ala Gly Glu Ala Gly Glu Gly Gly Gly Val
    130                 135                 140

Ile Gln Gly Ser Ala Ser Glu Ala Thr Leu Val Ala Leu Leu Ala Ala
145                 150                 155                 160

Arg Thr Lys Val Val Arg Arg Leu Gln Ala Ala Ser Pro Gly Leu Thr
                165                 170                 175

Gln Gly Ala Val Leu Glu Lys Leu Val Ala Tyr Ala Ser Asp Gln Ala
            180                 185                 190

His Ser Ser Val Glu Arg Ala Gly Leu Ile Gly Gly Val Lys Leu Lys
```

-continued 195                 200                 205
Ala Ile Pro Ser Asp Gly Lys Phe Ala Met Arg Ala Ser Ala Leu Gln
    210                 215                 220

Glu Ala Leu Glu Arg Asp Lys Ala Ala Gly Leu Ile Pro Phe Phe Val
225                 230                 235                 240

Val Ala Thr Leu Gly Thr Thr Ser Cys Cys Ser Phe Asp Asn Leu Leu
                245                 250                 255

Glu Val Gly Pro Ile Cys His Glu Glu Asp Ile Trp Leu His Val Asp
                260                 265                 270

Ala Ala Tyr Ala Gly Ser Ala Phe Ile Cys Pro Glu Phe Arg His Leu
            275                 280                 285

Leu Asn Gly Val Glu Phe Ala Asp Ser Phe Asn Phe Asn Pro His Lys
    290                 295                 300

Trp Leu Leu Val Asn Phe Asp Cys Ser Ala Met Trp Val Lys Arg Arg
305                 310                 315                 320

Thr Asp Leu Thr Gly Ala Phe Lys Leu Asp Pro Val Tyr Leu Lys His
                325                 330                 335

Ser His Gln Gly Ser Gly Leu Ile Thr Asp Tyr Arg His Trp Gln Leu
            340                 345                 350

Pro Leu Gly Arg Arg Phe Arg Ser Leu Lys Met Trp Phe Val Phe Arg
            355                 360                 365

Met Tyr Gly Val Lys Gly Leu Gln Ala Tyr Ile Arg Lys His Val Gln
    370                 375                 380

Leu Ser His Glu Phe Glu Ala Phe Val Leu Gln Asp Pro Arg Phe Glu
385                 390                 395                 400

Val Cys Ala Glu Val Thr Leu Gly Leu Val Cys Phe Arg Leu Lys Gly
                405                 410                 415

Ser Asp Gly Leu Asn Glu Ala Leu Leu Glu Arg Ile Asn Ser Ala Arg
            420                 425                 430

Lys Ile His Leu Val Pro Cys Arg Leu Arg Gly Gln Phe Val Leu Arg
        435                 440                 445

Phe Ala Ile Cys Ser Arg Lys Val Glu Ser Gly His Val Arg Leu Ala
    450                 455                 460

Trp Glu His Ile Arg Gly Leu Ala Ala Glu Leu Leu Ala Ala Glu Glu
465                 470                 475                 480

Gly Lys Ala Glu Ile Lys Ser
                485

<210> SEQ ID NO 57
<211> LENGTH: 1098
<212> TYPE: DNA
<213> ORGANISM: Candida boidinii

<400> SEQUENCE: 57
atgggtaaga ttgtcttagt tctttatgat gctggtaagc acgctgctga tgaagaaaaa      60
ttatatggtt gtactgaaaa taaattaggt attgctaatt ggttaaaaga tcaaggtcat     120
gaactaatta ctacttctga taagaaggt gaaacaagtg aattggataa acatatccca     180
gatgctgata ttatcatcac cactcctttc catcctgctt atatcactaa ggaaagactt     240
gacaaggcta gaactttaaa attagtcgtt gtcgctggtg ttggttctga tcacattgat     300
ttagattata ttaatcaaac aggtaagaaa atctcagtcc tggaagttac aggttctaat     360
gttgtctctg ttgctgaaca cgttgtcatg accatgcttg tcttggttag aaatttcgtt     420
ccagcacatg aacaaattat taaccacgat tgggaggttg ctgctatcgc taaggatgct     480

-continued

```
tacgatatcg aaggtaaaac tatcgctacc attggtgctg gtagaattgg ttacagagtc    540
ttggaaagat tactcccatt taatccaaaa gaattattat actacgatta tcaagcttta    600
ccaaaagaag ctgaagaaaa agttggtgct agaagagttg aaaatattga agaattagtt    660
gctcaagctg atatcgttac agttaatgct ccattacacg caggtacaaa aggtttaatt    720
aataaggaat tattatctaa atttaaaaaa ggtgcttggt tagtcaatac cgcaagaggt    780
gctatttgtg ttgctgaaga tgttgcagca gctttagaat ctggtcaatt aagaggttac    840
ggtggtgatg tttggttccc acaaccagct ccaaaggatc acccatggag agatatgaga    900
aataaatatg gtgctggtaa tgccatgact cctcactact ctggtactac tttagacgct    960
caaacaagat acgctgaagg tactaaaaat attttggaat cattctttac cggtaaattt   1020
gattacagac cacaagatat tatcttatta aatggtgaat acgttactaa agcttacggt   1080
aaacacgata agaaataa                                                 1098
```

<210> SEQ ID NO 58
<211> LENGTH: 365
<212> TYPE: PRT
<213> ORGANISM: Candida boidinii

<400> SEQUENCE: 58

```
Met Gly Lys Ile Val Leu Val Leu Tyr Asp Ala Gly Lys His Ala Ala
  1               5                  10                  15

Asp Glu Glu Lys Leu Tyr Gly Cys Thr Glu Asn Lys Leu Gly Ile Ala
                 20                  25                  30

Asn Trp Leu Lys Asp Gln Gly His Glu Leu Ile Thr Thr Ser Asp Lys
             35                  40                  45

Glu Gly Glu Thr Ser Glu Leu Asp Lys His Ile Pro Asp Ala Asp Ile
         50                  55                  60

Ile Ile Thr Thr Pro Phe His Pro Ala Tyr Ile Thr Lys Glu Arg Leu
 65                  70                  75                  80

Asp Lys Ala Lys Asn Leu Lys Leu Val Val Val Ala Gly Val Gly Ser
                 85                  90                  95

Asp His Ile Asp Leu Asp Tyr Ile Asn Gln Thr Gly Lys Lys Ile Ser
            100                 105                 110

Val Leu Glu Val Thr Gly Ser Asn Val Val Ser Val Ala Glu His Val
            115                 120                 125

Val Met Thr Met Leu Val Leu Val Arg Asn Phe Val Pro Ala His Glu
        130                 135                 140

Gln Ile Ile Asn His Asp Trp Glu Val Ala Ala Ile Ala Lys Asp Ala
145                 150                 155                 160

Tyr Asp Ile Glu Gly Lys Thr Ile Ala Thr Ile Gly Ala Gly Arg Ile
                165                 170                 175

Gly Tyr Arg Val Leu Glu Arg Leu Leu Pro Phe Asn Pro Lys Glu Leu
            180                 185                 190

Leu Tyr Tyr Asp Tyr Gln Ala Leu Pro Lys Glu Ala Glu Lys Val
        195                 200                 205

Gly Ala Arg Arg Val Glu Asn Ile Glu Glu Leu Val Ala Gln Ala Asp
    210                 215                 220

Ile Val Thr Val Asn Ala Pro Leu His Ala Gly Thr Lys Gly Leu Ile
225                 230                 235                 240

Asn Lys Glu Leu Leu Ser Lys Phe Lys Lys Gly Ala Trp Leu Val Asn
                245                 250                 255
```

-continued

```
Thr Ala Arg Gly Ala Ile Cys Val Ala Glu Asp Val Ala Ala Ala Leu
            260                 265                 270

Glu Ser Gly Gln Leu Arg Gly Tyr Gly Gly Asp Val Trp Phe Pro Gln
        275                 280                 285

Pro Ala Pro Lys Asp His Pro Trp Arg Asp Met Arg Asn Lys Tyr Gly
    290                 295                 300

Ala Gly Asn Ala Met Thr Pro His Tyr Ser Gly Thr Thr Leu Asp Ala
305                 310                 315                 320

Gln Thr Arg Tyr Ala Glu Gly Thr Lys Asn Ile Leu Glu Ser Phe Phe
                325                 330                 335

Thr Gly Lys Phe Asp Tyr Arg Pro Gln Asp Ile Ile Leu Leu Asn Gly
            340                 345                 350

Glu Tyr Val Thr Lys Ala Tyr Gly Lys His Asp Lys Lys
        355                 360                 365
```

<210> SEQ ID NO 59
<211> LENGTH: 1098
<212> TYPE: DNA
<213> ORGANISM: Artificial Sequence
<220> FEATURE:
<223> OTHER INFORMATION: Synthetic gene derived from Candida boidinii
    formate dehydrogenase, having numerous codons replaced with others
    encoding the same amino acids to reduce free energy of folding,
    and a gly codon inserted after the initiating met codon to insert
    a restriction site

<400> SEQUENCE: 59

```
atgggcaaaa tcgttctggt tctgtatgac gctggtaaac acgctgctga cgaagaaaaa      60
ctgtacggct gcaccgaaaa caaactgggt atcgctaact ggctgaaaga tcagggtcac     120
gaactgatca ctacctctga caagaaggt gaaacctctg aactggacaa acacatcccg     180
gatgcagata tcatcatcac cactccgttc cacccggctt acatcaccaa agagcgtctg     240
gacaaagcta aaaacctgaa actggtagta gttgctggtg taggttctga ccacatcgac     300
ctggactaca tcaaccagac tggtaaaaaa atctctgtac tggaagtaac tggttctaac     360
gttgtttctg ttgctgaaca cgttgtaatg actatgctgg ttctggttcg taacttcgtt     420
ccggctcacg aacagatcat caaccacgat tgggaagttg cagcaatcgc taaagacgct     480
tatgacatcg aagcaaaac catcgctact atcggcgctg ccgtatcgg ttaccgtgtt     540
ctggaacgtc tgctgccgtt caacccgaaa gaactgctgt actacgacta ccaggctctg     600
ccgaaagaag cagaggagaa agttggtgct cgccgtgtag agaacatcga agagctggta     660
gctcaggctg acatcgttac tgttaacgct ccgctgcacg caggcactaa aggtctgatt     720
aacaaagagc tgctgtctaa attcaaaaaa ggtgcatggc tggttaacac tgcacgtggt     780
gctatctgcg ttgctgaaga cgttgctgct gcactggaat ctggtcagct gcgtggttac     840
ggtggtgacg tatggtttcc gcagccggct ccgaaagatc accgtggcg tgatatgcgt     900
aacaaatatg gcgctggtaa cgcaatgacc ccgcactact ctggtaccac tctggatgct     960
cagacccgtt acgctgaagg tactaaaaac atcctggaat cttccttcac tggtaaattc    1020
gactaccgcc gcaggacat cattctgctg aacggtgaat atgtaactaa agcttacggc    1080
aaacacgaca aaaataa                                                   1098
```

<210> SEQ ID NO 60
<211> LENGTH: 365
<212> TYPE: PRT
<213> ORGANISM: Artificial Sequence
<220> FEATURE:

<223> OTHER INFORMATION: Synthetic protein derived from Candida boidinii
    formate dehydrogenase, having a glycine inserted after the
    initiating methionine

<400> SEQUENCE: 60

```
Met Gly Lys Ile Val Leu Val Leu Tyr Asp Ala Gly Lys His Ala Ala
1               5                   10                  15

Asp Glu Glu Lys Leu Tyr Gly Cys Thr Glu Asn Lys Leu Gly Ile Ala
            20                  25                  30

Asn Trp Leu Lys Asp Gln Gly His Glu Leu Ile Thr Thr Ser Asp Lys
        35                  40                  45

Glu Gly Glu Thr Ser Glu Leu Asp Lys His Ile Pro Asp Ala Asp Ile
    50                  55                  60

Ile Ile Thr Thr Pro Phe His Pro Ala Tyr Ile Thr Lys Glu Arg Leu
65                  70                  75                  80

Asp Lys Ala Lys Asn Leu Lys Leu Val Val Ala Gly Val Gly Ser
                85                  90                  95

Asp His Ile Asp Leu Asp Tyr Ile Asn Gln Thr Gly Lys Lys Ile Ser
            100                 105                 110

Val Leu Glu Val Thr Gly Ser Asn Val Val Ser Val Ala Glu His Val
        115                 120                 125

Val Met Thr Met Leu Val Leu Val Arg Asn Phe Val Pro Ala His Glu
130                 135                 140

Gln Ile Ile Asn His Asp Trp Glu Val Ala Ala Ile Ala Lys Asp Ala
145                 150                 155                 160

Tyr Asp Ile Glu Gly Lys Thr Ile Ala Thr Ile Gly Ala Gly Arg Ile
                165                 170                 175

Gly Tyr Arg Val Leu Glu Arg Leu Leu Pro Phe Asn Pro Lys Glu Leu
            180                 185                 190

Leu Tyr Tyr Asp Tyr Gln Ala Leu Pro Lys Glu Ala Glu Glu Lys Val
        195                 200                 205

Gly Ala Arg Arg Val Glu Asn Ile Glu Glu Leu Val Ala Gln Ala Asp
    210                 215                 220

Ile Val Thr Val Asn Ala Pro Leu His Ala Gly Thr Lys Gly Leu Ile
225                 230                 235                 240

Asn Lys Glu Leu Leu Ser Lys Phe Lys Lys Gly Ala Trp Leu Val Asn
                245                 250                 255

Thr Ala Arg Gly Ala Ile Cys Val Ala Glu Asp Val Ala Ala Ala Leu
            260                 265                 270

Glu Ser Gly Gln Leu Arg Gly Tyr Gly Gly Asp Val Trp Phe Pro Gln
        275                 280                 285

Pro Ala Pro Lys Asp His Pro Trp Arg Asp Met Arg Asn Lys Tyr Gly
    290                 295                 300

Ala Gly Asn Ala Met Thr Pro His Tyr Ser Gly Thr Thr Leu Asp Ala
305                 310                 315                 320

Gln Thr Arg Tyr Ala Glu Gly Thr Lys Asn Ile Leu Glu Ser Phe Phe
                325                 330                 335

Thr Gly Lys Phe Asp Tyr Arg Pro Gln Asp Ile Ile Leu Leu Asn Gly
            340                 345                 350

Glu Tyr Val Thr Lys Ala Tyr Gly Lys His Asp Lys Lys
        355                 360                 365
```

<210> SEQ ID NO 61
<211> LENGTH: 1488
<212> TYPE: DNA

<213> ORGANISM: Pseudomonas putida

<400> SEQUENCE: 61

```
atgtccctgt tgatccgtgg cgccaccgtg gtcacccacg aagagagtta ccccgccgat      60
gtcctgtgtg tcgatggcct gatccgtgcc atcgggccaa acctcgaacc gcccaccgac    120
tgtgaaatcc tcgacggcag cggccagtac ctgatgcccg gcggcatcga cccgcatacc    180
cacatgcagt tgccattcat gggcaccgtg gccagcgagg atttcttcag cggcaccgca    240
gcgggccttg ccggcggcac cacgtcgatc atcgacttcg tcatccccaa cccgcagcag    300
tcattgctgg aggccttcca cacctggcgc ggctgggcgc agaagagcgc cagcgactac    360
ggcttccacg ttgccatcac ctggtggagc gaacaggtgg ctgaagaaat gggcgaactg    420
gtagccaagc atggggtgaa cagcttcaag cacttcatgg cttacaagaa tgcaatcatg    480
gccgccgacg cacccctggt ggccagcttc gagcgctgcc tgcaactggg tgccgtgccc    540
accgtgcatg ccgagaacgg cgaactggtg taccacctgc agaaaaaact gcttgcccag    600
ggcatgaccg gaccagaggc tcacccctt tcgcgccctt cacaagtgga aggtgaagcg    660
gccagccgcg ccatccgtat tgccgaaacc attggtacgc cgctgtatgt ggtgcacatt    720
tccagccgtg aagcactgga tgaaatcacc tatgcacgcg ccaagggcca gccggtttac    780
ggcgaagtct tgcccggcca cctgctgctg acgacagcg tctaccgtga cccggactgg    840
gccactgccg ctggctacgt gatgagcccg ccgttccgcc cgcgcgagca ccaggaggcg    900
ctgtggcgcg gcttgcagtc gggcaacctg cacaccacgg ccaccgacca ctgctgtttc    960
tgcgccgaac agaaagccat gggccgcgac gacttcagtc gcatcccaa cggcaccgcc   1020
ggcatcgaag accgcatggc ggtgctgtgg gatgccggtg tcaacagcgg cgcctgtcg    1080
atgcatgagt tcgttgcgct gacctccacc aacacggcaa aaatcttcaa ccttttccca   1140
cgcaagggcg ccatccgcgt gggtgccgac gccgacctgg tgctgtggga cccgcagggc   1200
actcgcactc tatcggccca gacccaccac cagcgggtgg acttcaatat ctttgaaggc   1260
cgcactgtgc gcggggtccc cagccacacc atcagccagg caaggtgct ctgggccgat    1320
ggcgacctgc gtcgccgagg ccggggcggg gcggtatgtg aacggccgg cgtatccgtc    1380
ggtgtacgag gtgctggggc gacgcgccga acagcagcgc ccgacgcccg ttcagcgctg   1440
aggccattgg ggctgctgcg cagcccatcg ccggcaagcc aaatataa                1488
```

<210> SEQ ID NO 62
<211> LENGTH: 495
<212> TYPE: PRT
<213> ORGANISM: Pseudomonas putida

<400> SEQUENCE: 62

```
Met Ser Leu Leu Ile Arg Gly Ala Thr Val Val Thr His Glu Glu Ser
1               5                   10                  15
Tyr Pro Ala Asp Val Leu Cys Val Asp Gly Leu Ile Arg Ala Ile Gly
            20                  25                  30
Pro Asn Leu Glu Pro Pro Thr Asp Cys Glu Ile Leu Asp Gly Ser Gly
        35                  40                  45
Gln Tyr Leu Met Pro Gly Gly Ile Asp Pro His Thr His Met Gln Leu
    50                  55                  60
Pro Phe Met Gly Thr Val Ala Ser Glu Asp Phe Phe Ser Gly Thr Ala
65                  70                  75                  80
Ala Gly Leu Ala Gly Gly Thr Thr Ser Ile Ile Asp Phe Val Ile Pro
                85                  90                  95
```

-continued

```
Asn Pro Gln Gln Ser Leu Leu Glu Ala Phe His Thr Trp Arg Gly Trp
            100                 105                 110
Ala Gln Lys Ser Ala Ser Asp Tyr Gly Phe His Val Ala Ile Thr Trp
        115                 120                 125
Trp Ser Glu Gln Val Ala Glu Glu Met Gly Glu Leu Val Ala Lys His
    130                 135                 140
Gly Val Asn Ser Phe Lys His Phe Met Ala Tyr Lys Asn Ala Ile Met
145                 150                 155                 160
Ala Ala Asp Asp Thr Leu Val Ala Ser Phe Glu Arg Cys Leu Gln Leu
                165                 170                 175
Gly Ala Val Pro Thr Val His Ala Glu Asn Gly Glu Leu Val Tyr His
            180                 185                 190
Leu Gln Lys Lys Leu Leu Ala Gln Gly Met Thr Gly Pro Glu Ala His
        195                 200                 205
Pro Leu Ser Arg Pro Ser Gln Val Glu Gly Ala Ala Ser Arg Ala
    210                 215                 220
Ile Arg Ile Ala Glu Thr Ile Gly Thr Pro Leu Tyr Val Val His Ile
225                 230                 235                 240
Ser Ser Arg Glu Ala Leu Asp Glu Ile Thr Tyr Ala Arg Ala Lys Gly
                245                 250                 255
Gln Pro Val Tyr Gly Glu Val Leu Pro Gly His Leu Leu Leu Asp Asp
            260                 265                 270
Ser Val Tyr Arg Asp Pro Asp Trp Ala Thr Ala Gly Tyr Val Met
        275                 280                 285
Ser Pro Pro Phe Arg Pro Arg Glu His Gln Glu Ala Leu Trp Arg Gly
    290                 295                 300
Leu Gln Ser Gly Asn Leu His Thr Thr Ala Thr Asp His Cys Cys Phe
305                 310                 315                 320
Cys Ala Glu Gln Lys Ala Met Gly Arg Asp Asp Phe Ser Arg Ile Pro
                325                 330                 335
Asn Gly Thr Ala Gly Ile Glu Asp Arg Met Ala Val Leu Trp Asp Ala
            340                 345                 350
Gly Val Asn Ser Gly Arg Leu Ser Met His Glu Phe Val Ala Leu Thr
        355                 360                 365
Ser Thr Asn Thr Ala Lys Ile Phe Asn Leu Phe Pro Arg Lys Gly Ala
    370                 375                 380
Ile Arg Val Gly Ala Asp Ala Asp Leu Val Leu Trp Asp Pro Gln Gly
385                 390                 395                 400
Thr Arg Thr Leu Ser Ala Gln Thr His His Gln Arg Val Asp Phe Asn
                405                 410                 415
Ile Phe Glu Gly Arg Thr Val Arg Gly Val Pro Ser His Thr Ile Ser
            420                 425                 430
Gln Gly Lys Val Leu Trp Ala Asp Gly Asp Leu Arg Arg Gly Arg
        435                 440                 445
Gly Gly Ala Val Cys Gly Thr Ala Gly Val Ser Val Gly Val Arg Gly
    450                 455                 460
Ala Gly Ala Thr Arg Arg Thr Ala Ala Pro Asp Ala Arg Ser Ala Leu
465                 470                 475                 480
Arg Pro Leu Gly Leu Leu Arg Ser Pro Ser Pro Ala Ser Gln Ile
                485                 490                 495
```

<210> SEQ ID NO 63
<211> LENGTH: 1491

<212> TYPE: DNA
<213> ORGANISM: Artificial Sequence
<220> FEATURE:
<223> OTHER INFORMATION: Synthetic gene derived from Pseudomonas putida
hydantoinase, having numerous codons replaced with others encoding
the same amino acids to reduce free energy of folding, and a gly
codon inserted after the initiating met codon to insert a
restriction site

<400> SEQUENCE: 63

| | | | | | |
|---|---|---|---|---|---|
| atgggctctc | tgctgatccg | tggtgctacc | gttgttaccc | acgaagaatc | ttatccggct | 60 |
| gacgttctgt | gcgttgacgg | tctgatccgt | gctatcggtc | cgaacctgga | accgccgacc | 120 |
| gactgcgaaa | tcctggacgg | ttctggtcag | tacctgatgc | cgggtggtat | cgacccgcat | 180 |
| actcacatgc | agctgccgtt | tatgggtact | gttgcttctg | aagacttctt | ctctggcacc | 240 |
| gctgctggtc | tggctggtgg | taccacctct | atcatcgact | cgttatccc | gaacccgcag | 300 |
| cagtctctgc | tggaagcttt | ccatacttgg | cgtggttggg | ctcagaaatc | tgcatctgac | 360 |
| tacggtttcc | acgttgctat | cacctggtgg | tctgaacagg | ttgctgaaga | atgggcgaa | 420 |
| ctggttgcta | acacggtgt | taactctttc | aaacacttca | tggcttacaa | aaacgcaatt | 480 |
| atggcggctg | acgacactct | ggttgcttct | ttcgaacgct | gtctgcagct | gggcgctgtt | 540 |
| ccgaccgttc | acgctgaaaa | cggcgagctg | gtttatcacc | tgcagaaaaa | actgctggct | 600 |
| cagggtatga | ctggcccgga | agctcacccg | ctgtctcgtc | cgtctcaggt | tgagggcgaa | 660 |
| gctgcttctc | gtgctatccg | tatcgctgaa | accatcggta | ccccgctgta | tgtagttcat | 720 |
| atctcttctc | gtgaagctct | ggatgagatt | acttacgcac | gtgctaaggg | tcagccggtt | 780 |
| tacggtgaag | ttctgccggg | tcatctgctg | ctggatgatt | ctgtataccg | cgatccggac | 840 |
| tgggcaactg | ctgctggtta | cgttatgtcc | ccgccgtttc | gtccgcgtga | gcatcaggag | 900 |
| gcactgtggc | gcggcctgca | gtctggtaac | ctgcatacta | ctgctactga | tcactgttgt | 960 |
| ttctgcgctg | agcagaaggc | tatgggtcgc | gatgacttct | ctcgcattcc | gaacggtact | 1020 |
| gctggcattg | aggaccgtat | ggctgttctg | tgggatgctg | gcgttaactc | tggtcgtctg | 1080 |
| tctatgcacg | aattcgttgc | tctgacctct | actaacactg | ctaaaatctt | caacctgttc | 1140 |
| ccgcgtaaag | gtgcaatccg | cgtaggtgca | gatgctgatc | tggttctgtg | ggatccgcag | 1200 |
| ggcactcgca | ctctgtctgc | tcagactcat | catcagcgtg | ttgacttcaa | catctttgag | 1260 |
| ggccgtactg | ttcgcggtgt | tccgtctcat | accatctctc | agggtaaagt | tctgtgggct | 1320 |
| gacggtgacc | tgcgtcgtcg | tggtcgtggt | ggtgctgttt | gcggtaccgc | tggtgttct | 1380 |
| gttggtgttc | gtggcgctgg | tgctacccgt | cgtactgctg | ctccggatgc | tcgttctgct | 1440 |
| ctgcgtccgc | tgggtctgct | gcgttctccg | tctccggctt | ctcagattta | a | 1491 |

<210> SEQ ID NO 64
<211> LENGTH: 496
<212> TYPE: PRT
<213> ORGANISM: Artificial Sequence
<220> FEATURE:
<223> OTHER INFORMATION: Synthetic protein derived from Pseudomonas
putida hydantoinase, having a glycine residue inserted after the
initiating methionine

<400> SEQUENCE: 64

Met Gly Ser Leu Leu Ile Arg Gly Ala Thr Val Val Thr His Glu Glu
1               5                   10                  15

Ser Tyr Pro Ala Asp Val Leu Cys Val Asp Gly Leu Ile Arg Ala Ile
            20                  25                  30

```
Gly Pro Asn Leu Glu Pro Pro Thr Asp Cys Glu Ile Leu Asp Gly Ser
            35                  40                  45

Gly Gln Tyr Leu Met Pro Gly Gly Ile Asp Pro His Thr His Met Gln
    50                  55                  60

Leu Pro Phe Met Gly Thr Val Ala Ser Glu Asp Phe Phe Ser Gly Thr
65                  70                  75                  80

Ala Ala Gly Leu Ala Gly Gly Thr Thr Ser Ile Ile Asp Phe Val Ile
                85                  90                  95

Pro Asn Pro Gln Gln Ser Leu Leu Glu Ala Phe His Thr Trp Arg Gly
            100                 105                 110

Trp Ala Gln Lys Ser Ala Ser Asp Tyr Gly Phe His Val Ala Ile Thr
            115                 120                 125

Trp Trp Ser Glu Gln Val Ala Glu Glu Met Gly Glu Leu Val Ala Lys
    130                 135                 140

His Gly Val Asn Ser Phe Lys His Phe Met Ala Tyr Lys Asn Ala Ile
145                 150                 155                 160

Met Ala Ala Asp Asp Thr Leu Val Ala Ser Phe Glu Arg Cys Leu Gln
                165                 170                 175

Leu Gly Ala Val Pro Thr Val His Ala Glu Asn Gly Glu Leu Val Tyr
            180                 185                 190

His Leu Gln Lys Lys Leu Leu Ala Gln Gly Met Thr Gly Pro Glu Ala
            195                 200                 205

His Pro Leu Ser Arg Pro Ser Gln Val Glu Gly Glu Ala Ala Ser Arg
            210                 215                 220

Ala Ile Arg Ile Ala Glu Thr Ile Gly Thr Pro Leu Tyr Val Val His
225                 230                 235                 240

Ile Ser Ser Arg Glu Ala Leu Asp Glu Ile Thr Tyr Ala Arg Ala Lys
                245                 250                 255

Gly Gln Pro Val Tyr Gly Glu Val Leu Pro Gly His Leu Leu Leu Asp
            260                 265                 270

Asp Ser Val Tyr Arg Asp Pro Asp Trp Ala Thr Ala Ala Gly Tyr Val
            275                 280                 285

Met Ser Pro Pro Phe Arg Pro Arg Glu His Gln Glu Ala Leu Trp Arg
    290                 295                 300

Gly Leu Gln Ser Gly Asn Leu His Thr Thr Ala Thr Asp His Cys Cys
305                 310                 315                 320

Phe Cys Ala Glu Gln Lys Ala Met Gly Arg Asp Asp Phe Ser Arg Ile
                325                 330                 335

Pro Asn Gly Thr Ala Gly Ile Glu Asp Arg Met Ala Val Leu Trp Asp
            340                 345                 350

Ala Gly Val Asn Ser Gly Arg Leu Ser Met His Glu Phe Val Ala Leu
            355                 360                 365

Thr Ser Thr Asn Thr Ala Lys Ile Phe Asn Leu Phe Pro Arg Lys Gly
    370                 375                 380

Ala Ile Arg Val Gly Ala Asp Ala Asp Leu Val Leu Trp Asp Pro Gln
385                 390                 395                 400

Gly Thr Arg Thr Leu Ser Ala Gln Thr His His Gln Arg Val Asp Phe
                405                 410                 415

Asn Ile Phe Glu Gly Arg Thr Val Arg Gly Val Pro Ser His Thr Ile
            420                 425                 430

Ser Gln Gly Lys Val Leu Trp Ala Asp Gly Asp Leu Arg Arg Arg Gly
            435                 440                 445

Arg Gly Gly Ala Val Cys Gly Thr Ala Gly Val Ser Val Gly Val Arg
```

|  |  |  | 450 |  |  |  | 455 |  |  |  | 460 |  |
|---|---|---|---|---|---|---|---|---|---|---|---|---|
| Gly | Ala | Gly | Ala | Thr | Arg | Arg | Thr | Ala | Ala | Pro | Asp | Ala | Arg | Ser | Ala |
| 465 |  |  |  |  | 470 |  |  |  |  | 475 |  |  |  |  | 480 |
| Leu | Arg | Pro | Leu | Gly | Leu | Leu | Arg | Ser | Pro | Pro | Ala | Ser | Gln | Ile |
|  |  |  |  | 485 |  |  |  |  | 490 |  |  |  |  | 495 |

<210> SEQ ID NO 65
<211> LENGTH: 1683
<212> TYPE: DNA
<213> ORGANISM: Penicillium simplicissimum

<400> SEQUENCE: 65

| atgtccaaga cacaggaatt caggcctttg acactgccac ccaagctgtc gttaagtgac | 60 |
|---|---|
| ttcaatgaat tcatccagga tattattcga atcgttggct ctgaaaatgt tgaagtcatt | 120 |
| agctcgaagg accagattgt tgacggttct tatatgaaac ctacgcacac gcacgatccc | 180 |
| catcatgtca tggaccagga ctacttcctt gcctcagcaa ttgttgctcc tcgcaatgtc | 240 |
| gccgatgtgc agtcgattgt cggacttgcc aataagttct catttcccct ctggcccatc | 300 |
| tctattggaa gaaattccgg atatggcggt gctgcgccac gggttagtgg cagtgtcgtg | 360 |
| ctggacatgg aaagaatat gaacagagtt ctagaagtga acgtggaagg cgcatattgc | 420 |
| gtggtggagc ccggtgtaac ttaccacgac ttgcataatt accttgaggc gaacaatctt | 480 |
| cgagacaaat tatggcttga tgtaccggat cttggtggcg ttctgttct cggcaatgcc | 540 |
| gttgagagag tgtgggcta tacgccttac ggagatcatt ggatgatgca cagtgggatg | 600 |
| gaagtcgtcc ttgcgaatgg cgagcttctt aggactggca tggggctct acctgatcct | 660 |
| aaacgtcccg aaacgatggg gctaaagcca gaagaccagc catggagcaa aatcgctcat | 720 |
| ctgtttcctt atggcttcgg tccctatata gatgggctat tcagccaatc gaatatggga | 780 |
| attgttacca agatcgggat ctggttaatg cccaatccag ggggttatca atcctacttg | 840 |
| atcacactac ccaaagatgg tgatttaaaa caagccgtcg atattattcg tccccttcgt | 900 |
| ctaggcatgg cccttcaaaa tgttcccact attcgccaca ttcttttgga tgcagcggtg | 960 |
| ctcggtgaca agcgatctta ttcatccaag accgaacccc tctccgacga ggaattagac | 1020 |
| aagatcgcga aacagctcaa cttgggacga tggaactttt acggggcgct ctatggacct | 1080 |
| gagccgattc gaagggttct ctgggaaacg attaaagacg cattctcggc gatcccaggc | 1140 |
| gtcaagtttt attttccgga ggacactcct gaaaactccg ttctccgcgt gcgtgataag | 1200 |
| actatgcaag gcattccaac ttacgacgag ctaaagtgga tcgattggct ccctaatggt | 1260 |
| gcgcatctgt tcttctctcc tattgcgaag gtatctggtg aagatgcaat gatgcaatac | 1320 |
| gcagtcacca agaaaaggtg tcaggaggct gggttagatt ttatcggcac tttcacagtc | 1380 |
| ggtatgagag agatgcatca tatcgtttgt attgtgttca acaagaagga cctaatacaa | 1440 |
| aagagaaaag tacagtggct gatgagaacc cttattgatg actgtgctgc aaatggatgg | 1500 |
| ggcgaatatc gaacccatct ggccttcatg gaccaaatta tggaaaccta caactggaac | 1560 |
| aacagcagct tcctaaggtt caatgaggtc ctcaagaatg cggtggatcc taatggcatc | 1620 |
| attgccccgg gaaagtctgg tgtttggccg agtcaataca gtcatgttac ttggaaactg | 1680 |
| taa | 1683 |

<210> SEQ ID NO 66
<211> LENGTH: 560
<212> TYPE: PRT
<213> ORGANISM: Penicillium simplicissimum -continued

<400> SEQUENCE: 66

```
Met Ser Lys Thr Gln Glu Phe Arg Pro Leu Thr Leu Pro Pro Lys Leu
1               5                   10                  15

Ser Leu Ser Asp Phe Asn Glu Phe Ile Gln Asp Ile Ile Arg Ile Val
            20                  25                  30

Gly Ser Glu Asn Val Glu Val Ile Ser Ser Lys Asp Gln Ile Val Asp
        35                  40                  45

Gly Ser Tyr Met Lys Pro Thr His Thr His Asp Pro His His Val Met
    50                  55                  60

Asp Gln Asp Tyr Phe Leu Ala Ser Ala Ile Val Ala Pro Arg Asn Val
65                  70                  75                  80

Ala Asp Val Gln Ser Ile Val Gly Leu Ala Asn Lys Phe Ser Phe Pro
                85                  90                  95

Leu Trp Pro Ile Ser Ile Gly Arg Asn Ser Gly Tyr Gly Gly Ala Ala
            100                 105                 110

Pro Arg Val Ser Gly Ser Val Val Leu Asp Met Gly Lys Asn Met Asn
        115                 120                 125

Arg Val Leu Glu Val Asn Val Glu Gly Ala Tyr Cys Val Val Glu Pro
    130                 135                 140

Gly Val Thr Tyr His Asp Leu His Asn Tyr Leu Glu Ala Asn Asn Leu
145                 150                 155                 160

Arg Asp Lys Leu Trp Leu Asp Val Pro Asp Leu Gly Gly Gly Ser Val
                165                 170                 175

Leu Gly Asn Ala Val Glu Arg Gly Val Gly Tyr Thr Pro Tyr Gly Asp
            180                 185                 190

His Trp Met Met His Ser Gly Met Glu Val Val Leu Ala Asn Gly Glu
        195                 200                 205

Leu Leu Arg Thr Gly Met Gly Ala Leu Pro Asp Pro Lys Arg Pro Glu
    210                 215                 220

Thr Met Gly Leu Lys Pro Glu Asp Gln Pro Trp Ser Lys Ile Ala His
225                 230                 235                 240

Leu Phe Pro Tyr Gly Phe Gly Pro Tyr Ile Asp Gly Leu Phe Ser Gln
                245                 250                 255

Ser Asn Met Gly Ile Val Thr Lys Ile Gly Ile Trp Leu Met Pro Asn
            260                 265                 270

Pro Gly Gly Tyr Gln Ser Tyr Leu Ile Thr Leu Pro Lys Asp Gly Asp
        275                 280                 285

Leu Lys Gln Ala Val Asp Ile Ile Arg Pro Leu Arg Leu Gly Met Ala
    290                 295                 300

Leu Gln Asn Val Pro Thr Ile Arg His Ile Leu Leu Asp Ala Ala Val
305                 310                 315                 320

Leu Gly Asp Lys Arg Ser Tyr Ser Ser Lys Thr Glu Pro Leu Ser Asp
                325                 330                 335

Glu Glu Leu Asp Lys Ile Ala Lys Gln Leu Asn Leu Gly Arg Trp Asn
            340                 345                 350

Phe Tyr Gly Ala Leu Tyr Gly Pro Glu Pro Ile Arg Arg Val Leu Trp
        355                 360                 365

Glu Thr Ile Lys Asp Ala Phe Ser Ala Ile Pro Gly Val Lys Phe Tyr
    370                 375                 380

Phe Pro Glu Asp Thr Pro Glu Asn Ser Val Leu Arg Val Arg Asp Lys
385                 390                 395                 400

Thr Met Gln Gly Ile Pro Thr Tyr Asp Glu Leu Lys Trp Ile Asp Trp
```

405                 410                 415
Leu Pro Asn Gly Ala His Leu Phe Phe Ser Pro Ile Ala Lys Val Ser
            420                 425                 430

Gly Glu Asp Ala Met Met Gln Tyr Ala Val Thr Lys Lys Arg Cys Gln
        435                 440                 445

Glu Ala Gly Leu Asp Phe Ile Gly Thr Phe Thr Val Gly Met Arg Glu
    450                 455                 460

Met His His Ile Val Cys Ile Val Phe Asn Lys Lys Asp Leu Ile Gln
465                 470                 475                 480

Lys Arg Lys Val Gln Trp Leu Met Arg Thr Leu Ile Asp Asp Cys Ala
                485                 490                 495

Ala Asn Gly Trp Gly Glu Tyr Arg Thr His Leu Ala Phe Met Asp Gln
            500                 505                 510

Ile Met Glu Thr Tyr Asn Trp Asn Asn Ser Ser Phe Leu Arg Phe Asn
        515                 520                 525

Glu Val Leu Lys Asn Ala Val Asp Pro Asn Gly Ile Ile Ala Pro Gly
    530                 535                 540

Lys Ser Gly Val Trp Pro Ser Gln Tyr Ser His Val Thr Trp Lys Leu
545                 550                 555                 560

<210> SEQ ID NO 67
<211> LENGTH: 1686
<212> TYPE: DNA
<213> ORGANISM: Artificial Sequence
<220> FEATURE:
<223> OTHER INFORMATION: Synthetic gene derived from Penicillium
    simplicissium vanillyl alcohol oxidase, having numerous codons
    replaced with others encoding the same amino acids to reduce free
    energy of folding and a gly codon inserted after the initiating
    met codon to insert a restriction site

<400> SEQUENCE: 67
atgggctcta aaactcagga gttccgtccg ctgaccctgc cgccgaaact gtctctgtct      60
gattttaacg aattcatcca ggatatcatc cgtatcgttg gttctgaaaa cgttgaagtt     120
atctcttcta agaccagat cgttgacggt tcttacatga aaccgaccca cacccacgac      180
ccgcaccacg ttatggacca ggactacttc ctggcttctg ctatcgttgc tccgcgtaac     240
gttgctgacg ttcagtctat cgttggtctg gctaacaaat tctcttttcc cgctgtggccg    300 atctctatcg tcgtaactc tggttacggt ggtgctgctc cgcgtgtttc tggttctgtt      360
gttctggaca tgggtaaaaa catgaaccgt gttctggaag ttaacgttga aggtgcttac     420
tgcgttgttg aaccgggtgt aacttatcat gacctgcaca actacctgga agctaacaac     480
ctgcgtgaca aactgtggct ggacgtaccg gatctgggtg gtggttctgt tctgggtaac     540
gctgttgaac gtggtgttgg ttacacccg tacggtgatc attggatgat gcactctggc      600
atggaggtag tactggctaa cggtgaactg ctgcgtaccg gtatgggtgc tctgccggac     660
ccgaagcgtc cggaaactat gggtctgaag ccggaggatc agccgtggtc taaaatcgct     720
catctgttcc cgtatggctt tggtccgtac atcgacggtc tgttctctca gtctaacatg     780
ggtatcgtta ccaaaattgg catttggctg atgccgaacc cgggtggtta ccagtcttac     840
ctgattactc tgccgaaaga tggcgacctg aaacaggctg ttgatatcat tcgcccgctg     900
cgtctgggta tggctctgca gaacgttccg actatccgcc acatcctgct ggacgctgca     960
gtactgggtg acaaacgttc ctactcctct aaaactgaac cgctgtctga cgaagaactg    1020
gacaaaatcg ctaaacagct gaacctgggt cgttggaact tctacggtgc tctgtacggt    1080

-continued

```
ccggaaccga tccgtcgtgt tctgtgggag actatcaagg atgctttctc tgctatcccg   1140
ggtgttaaat tctacttccc ggaagacact ccggaaaact ctgttctgcg tgtacgtgac   1200
aaaaccatgc agggtatccc gacctacgac gaactgaaat ggatcgactg gctgccgaac   1260
ggtgctcacc tgttctttc tccgatcgct aaagtatccg gagaggacgc tatgatgcag   1320
tatgctgtta ccaaaaaacg ttgtcaggaa gctggtctgg atttcattgg taccttcact   1380
gtaggtatgc gcgaaatgca tcatattgtt tgcatcgttt tcaacaaaaa agacctgatt   1440
cagaagcgca aagttcagtg gctgatgcgt accctgatcg acgactgtgc tgctaacggt   1500
tggggtgaat accgtaccca cctggcattc atggaccaga tcatggaaac ctacaactgg   1560
aacaactctt ctttcctgcg tttcaacgaa gttctgaaaa acgctgttga cccgaacggt   1620
atcatcgctc cgggtaaatc tggtgtttgg ccgtctcagt actctcacgt tacctggaaa   1680
ctgtaa                                                             1686
```

<210> SEQ ID NO 68
<211> LENGTH: 561
<212> TYPE: PRT
<213> ORGANISM: Artificial Sequence
<220> FEATURE:
<223> OTHER INFORMATION: Synthetic protein derived from Penicillium
simplicissium vanillyl alcohol oxidase, having a glycine residue
inserted after the initiating methionine

<400> SEQUENCE: 68

```
Met Gly Ser Lys Thr Gln Glu Phe Arg Pro Leu Thr Leu Pro Pro Lys
1               5                   10                  15

Leu Ser Leu Ser Asp Phe Asn Glu Phe Ile Gln Asp Ile Ile Arg Ile
                20                  25                  30

Val Gly Ser Glu Asn Val Glu Val Ile Ser Ser Lys Asp Gln Ile Val
            35                  40                  45

Asp Gly Ser Tyr Met Lys Pro Thr His Thr His Asp Pro His His Val
        50                  55                  60

Met Asp Gln Asp Tyr Phe Leu Ala Ser Ala Ile Val Ala Pro Arg Asn
65                  70                  75                  80

Val Ala Asp Val Gln Ser Ile Val Gly Leu Ala Asn Lys Phe Ser Phe
                85                  90                  95

Pro Leu Trp Pro Ile Ser Ile Gly Arg Asn Ser Gly Tyr Gly Gly Ala
                100                 105                 110

Ala Pro Arg Val Ser Gly Ser Val Val Leu Asp Met Gly Lys Asn Met
            115                 120                 125

Asn Arg Val Leu Glu Val Asn Val Glu Gly Ala Tyr Cys Val Val Glu
        130                 135                 140

Pro Gly Val Thr Tyr His Asp Leu His Asn Tyr Leu Glu Ala Asn Asn
145                 150                 155                 160

Leu Arg Asp Lys Leu Trp Leu Asp Val Pro Asp Leu Gly Gly Gly Ser
                165                 170                 175

Val Leu Gly Asn Ala Val Glu Arg Gly Val Gly Tyr Thr Pro Tyr Gly
            180                 185                 190

Asp His Trp Met Met His Ser Gly Met Glu Val Val Leu Ala Asn Gly
        195                 200                 205

Glu Leu Leu Arg Thr Gly Met Gly Ala Leu Pro Asp Pro Lys Arg Pro
    210                 215                 220

Glu Thr Met Gly Leu Lys Pro Glu Asp Gln Pro Trp Ser Lys Ile Ala
225                 230                 235                 240
```

His Leu Phe Pro Tyr Gly Phe Gly Pro Tyr Ile Asp Gly Leu Phe Ser
                245                 250                 255

Gln Ser Asn Met Gly Ile Val Thr Lys Ile Gly Ile Trp Leu Met Pro
                260                 265                 270

Asn Pro Gly Gly Tyr Gln Ser Tyr Leu Ile Thr Leu Pro Lys Asp Gly
                275                 280                 285

Asp Leu Lys Gln Ala Val Asp Ile Ile Arg Pro Leu Arg Leu Gly Met
            290                 295                 300

Ala Leu Gln Asn Val Pro Thr Ile Arg His Ile Leu Leu Asp Ala Ala
305                 310                 315                 320

Val Leu Gly Asp Lys Arg Ser Tyr Ser Ser Lys Thr Glu Pro Leu Ser
                325                 330                 335

Asp Glu Glu Leu Asp Lys Ile Ala Lys Gln Leu Asn Leu Gly Arg Trp
                340                 345                 350

Asn Phe Tyr Gly Ala Leu Tyr Gly Pro Glu Pro Ile Arg Arg Val Leu
                355                 360                 365

Trp Glu Thr Ile Lys Asp Ala Phe Ser Ala Ile Pro Gly Val Lys Phe
                370                 375                 380

Tyr Phe Pro Glu Asp Thr Pro Glu Asn Ser Val Leu Arg Val Arg Asp
385                 390                 395                 400

Lys Thr Met Gln Gly Ile Pro Thr Tyr Asp Glu Leu Lys Trp Ile Asp
                405                 410                 415

Trp Leu Pro Asn Gly Ala His Leu Phe Phe Ser Pro Ile Ala Lys Val
                420                 425                 430

Ser Gly Glu Asp Ala Met Met Gln Tyr Ala Val Thr Lys Lys Arg Cys
            435                 440                 445

Gln Glu Ala Gly Leu Asp Phe Ile Gly Thr Phe Thr Val Gly Met Arg
        450                 455                 460

Glu Met His His Ile Val Cys Ile Val Phe Asn Lys Lys Asp Leu Ile
465                 470                 475                 480

Gln Lys Arg Lys Val Gln Trp Leu Met Arg Thr Leu Ile Asp Asp Cys
                485                 490                 495

Ala Ala Asn Gly Trp Gly Glu Tyr Arg Thr His Leu Ala Phe Met Asp
            500                 505                 510

Gln Ile Met Glu Thr Tyr Asn Trp Asn Asn Ser Ser Phe Leu Arg Phe
        515                 520                 525

Asn Glu Val Leu Lys Asn Ala Val Asp Pro Asn Gly Ile Ile Ala Pro
        530                 535                 540

Gly Lys Ser Gly Val Trp Pro Ser Gln Tyr Ser His Val Thr Trp Lys
545                 550                 555                 560

Leu

<210> SEQ ID NO 69
<211> LENGTH: 852
<212> TYPE: DNA
<213> ORGANISM: Candida magnoliae

<400> SEQUENCE: 69
atggctaaga acttctccaa cgtcgagtac cccgccccgc ctccggccca caccaagaac       60
gagtcgctgc aggtccttga cctgttcaag ctgaatggca aggttgccag catcactggc      120
tcgtccagcg gtattggcta cgctctggct gaggccttcg cgcaggtcgg cgctgacgtc      180
gccatctggt acaacagcca cgacgctact ggcaaggctg aggccctcgc caagaagtac      240
ggcgtcaagg tcaaggccta caggcgaaac gtgagcagct ctgacgccgt gaagcagacg      300

-continued

```
atcgagcagc agatcaagga cttcggccac ctcgacattg tcgtggcgaa cgccggcatt    360
ccctggacga agggtgccta catcgaccag gacgacgaca agcacttcga ccaggtcgtt    420
gacgtcgatc tgaagggtgt tggatacgtc gcgaagcacg ctggccgtca cttccgcgag    480
cgcttcgaga aggagggcaa gaagggcgcc cttgtgttca cggcctccat gtctggccac    540
attgtgaacg tgccccagtt ccaggccacg tacaacgcgg ccaaggctgg cgtgcgccac    600
ttcgcgaagt cgctggccgt cgagttcgcg ccgttcgcgc gcgtgaactc tgtgtcgccg    660
ggctacatca acacggagat ctcggacttc gtgccccagg agacgcagaa caagtggtgg    720
tcgctcgtgc cccttggccg cggcggagag acggccgagc tcgttggcgc ctacctgttc    780
cttgcatctg acgccggctc gtacgccact ggtacggaca tcattgttga cggtggctac    840
acgcttccct aa                                                        852
```

<210> SEQ ID NO 70
<211> LENGTH: 283
<212> TYPE: PRT
<213> ORGANISM: Candida magnoliae

<400> SEQUENCE: 70

```
Met Ala Lys Asn Phe Ser Asn Val Glu Tyr Pro Ala Pro Pro Pro Ala
1               5                   10                  15

His Thr Lys Asn Glu Ser Leu Gln Val Leu Asp Leu Phe Lys Leu Asn
            20                  25                  30

Gly Lys Val Ala Ser Ile Thr Gly Ser Ser Ser Gly Ile Gly Tyr Ala
        35                  40                  45

Leu Ala Glu Ala Phe Ala Gln Val Gly Ala Asp Val Ala Ile Trp Tyr
    50                  55                  60

Asn Ser His Asp Ala Thr Gly Lys Ala Glu Ala Leu Ala Lys Lys Tyr
65                  70                  75                  80

Gly Val Lys Val Lys Ala Tyr Lys Ala Asn Val Ser Ser Asp Ala
                85                  90                  95

Val Lys Gln Thr Ile Glu Gln Ile Lys Asp Phe Gly His Leu Asp
            100                 105                 110

Ile Val Val Ala Asn Ala Gly Ile Pro Trp Thr Lys Gly Ala Tyr Ile
        115                 120                 125

Asp Gln Asp Asp Asp Lys His Phe Asp Gln Val Val Asp Val Asp Leu
130                 135                 140

Lys Gly Val Gly Tyr Val Ala Lys His Ala Gly Arg His Phe Arg Glu
145                 150                 155                 160

Arg Phe Glu Lys Glu Gly Lys Lys Gly Ala Leu Val Phe Thr Ala Ser
                165                 170                 175

Met Ser Gly His Ile Val Asn Val Pro Gln Phe Gln Ala Thr Tyr Asn
            180                 185                 190

Ala Ala Lys Ala Gly Val Arg His Phe Ala Lys Ser Leu Ala Val Glu
        195                 200                 205

Phe Ala Pro Phe Ala Arg Val Asn Ser Val Ser Pro Gly Tyr Ile Asn
    210                 215                 220

Thr Glu Ile Ser Asp Phe Val Pro Gln Glu Thr Gln Asn Lys Trp Trp
225                 230                 235                 240

Ser Leu Val Pro Leu Gly Arg Gly Gly Glu Thr Ala Glu Leu Val Gly
                245                 250                 255

Ala Tyr Leu Phe Leu Ala Ser Asp Ala Gly Ser Tyr Ala Thr Gly Thr
            260                 265                 270
```

Asp Ile Ile Val Asp Gly Gly Tyr Thr Leu Pro
        275                 280

<210> SEQ ID NO 71
<211> LENGTH: 852
<212> TYPE: DNA
<213> ORGANISM: Artificial Sequence
<220> FEATURE:
<223> OTHER INFORMATION: Synthetic gene derived from Candida magnoliae
      NADPH-dependent carbonyl reductase, having numerous codons
      replaced with others encoding the same amino acids to reduce the
      free energy of folding

<400> SEQUENCE: 71

```
atggctaaaa acttctctaa cgttgaatac ccggctccgc cgccagctca caccaaaaac      60
gaatctctgc aggttctgga cctgttcaaa ctgaacggta aggttgcttc tatcaccggt     120
tcttcttctg gtatcggtta cgctctggct gaagcattcg ctcaggtagg tgctgacgtt     180
gctatctggt acaactctca cgacgctact ggtaaggctg aagctctggc taaaaaatac     240
ggtgttaaag ttaaagctta caaggctaac gtttcttctt ctgacgctgt aaaacagacc     300
atcgaacagc agatcaaaga cttcggtcac ctggacatcg ttgttgctaa cgctggtatc     360
ccgtggacca aggtgctta catcgaccag gacgacgata acacttcga tcaggttgtt      420
gacgttgatc tgaaaggtgt tggttatgtt gctaaacacg ctggccgtca cttccgtgag     480
cgtttcgaaa aggaaggtaa gaaggcgct ctggttttca ccgcttctat gtctggtcac     540
atcgttaacg taccgcagtt tcaggctacc tacaacgctc taaagctgg tgttcgtcac     600
ttcgctaaat ctctggctgt agaattcgct ccgttcgctc gtgttaactc tgtttctccg     660
ggctacatca acaccgaaat ctctgacttt gtaccgcagg aaactcagaa caatggtgg     720
tctctggtac cgctgggccg tggtggcgaa actgctgaac tggttggtgc ttacctgttt     780
ctggcttctg acgctggttc ttacgctacc ggcactgaca tcatcgttga cggtggttac     840
accctgccgt aa                                                        852
```

<210> SEQ ID NO 72
<211> LENGTH: 1602
<212> TYPE: DNA
<213> ORGANISM: Saccharomyces cerevisiae

<400> SEQUENCE: 72

```
atgacagaag ataatattgc tccaatcacc tccgttaaag tagttaccga caagtgcacg      60
tacaaggaca acgagctgct caccaagtac agctacgaaa atgctgtagt tacgaagaca     120
gctagtggcc gcttcgatgt aacgcccact gttcaagact acgtgttcaa acttgacttg     180
aaaaagccgg aaaaactagg aattatgctc attgggttag gtggcaacaa tggctccact     240
ttagtggcct cggtattggc gaataagcac aatgtggagt tcaaaactaa ggaaggcgtt     300
aagcaaccaa actacttcgg ctccatgact caatgttcta ccttgaaact gggtatcgat     360
gcggagggga atgacgttta tgctcctttt aactctctgt tgcccatggt tagcccaaac     420
gactttgtcg tctctggttg ggacatcaat aacgcagatc tatacgaagc tatgcagaga     480
agtcaagttc tcgaatatga tctgcaacaa cgcttgaagg cgaagatgtc cttggtgaag     540
cctcttcctt ccatttacta ccctgatttc attgcagcta atcaagatga gagagccaat     600
aactgcatca atttggatga aaaaggcaac gtaaccacga gggtaagtg acccatctg     660
caacgcatca gacgcgatat ccagaatttc aaagaagaaa acgcccttga taaagtaatc     720
```

-continued

```
gttctttgga ctgcaaatac tgagaggtac gtagaagtat ctcctggtgt taatgacacc      780
atggaaaacc tcttgcagtc tattaagaat gaccatgaag agattgctcc ttccacgatc      840
tttgcagcag catctatctt ggaaggtgtc ccctatatta atggttcacc gcagaatact      900
tttgttcccg gcttggttca gctggctgag catgagggta cattcattgc gggagacgat      960
ctcaagtcgg gacaaaccaa gttgaagtct gttctggccc agttcttagt ggatgcaggt     1020
attaaaccgg tctccattgc atcctataac catttaggca ataatgacgg ttataactta     1080
tctgctccaa aacaatttag gtctaaggag atttccaaaa gttctgtcat agatgacatc     1140
atcgcgtcta atgatatctt gtacaatgat aaactgggta aaaagttga ccactgcatt      1200
gtcatcaaat atatgaagcc cgtcggggac tcaaaagtgg caatggacga gtattacagt     1260
gagttgatgt taggtggcca taaccggatt tccattcaca atgtttgcga agattcttta     1320
ctggctacgc ccttgatcat cgatcttta gtcatgactg agttttgtac aagagtgtcc      1380
tataagaagg tggacccagt taagaagat gctggcaaat cgagaactt ttatccagtt       1440
ttaaccttct tgagttactg gttaaaagct ccattaacaa gaccaggatt tcacccggtg     1500
aatggcttaa acaagcaaag aaccgcctta gaaaatttt taagattgtt gattggattg      1560
ccttctcaaa acgaactaag attcgaagag agattgttgt aa                        1602
```

<210> SEQ ID NO 73
<211> LENGTH: 533
<212> TYPE: PRT
<213> ORGANISM: Saccharomyces cerevisiae

<400> SEQUENCE: 73

| Met | Thr | Glu | Asp | Asn | Ile | Ala | Pro | Ile | Thr | Ser | Val | Lys | Val | Thr |
|---|---|---|---|---|---|---|---|---|---|---|---|---|---|---|
| 1 | | | | 5 | | | | | 10 | | | | | 15 |

| Asp | Lys | Cys | Thr | Tyr | Lys | Asp | Asn | Glu | Leu | Leu | Thr | Lys | Tyr | Ser | Tyr |
|---|---|---|---|---|---|---|---|---|---|---|---|---|---|---|---|
| | | | 20 | | | | | 25 | | | | | 30 | | |

| Glu | Asn | Ala | Val | Val | Thr | Lys | Thr | Ala | Ser | Gly | Arg | Phe | Asp | Val | Thr |
| | | 35 | | | | | 40 | | | | | 45 | | | |

| Pro | Thr | Val | Gln | Asp | Tyr | Val | Phe | Lys | Leu | Asp | Leu | Lys | Lys | Pro | Glu |
| 50 | | | | | 55 | | | | | 60 | | | | | |

| Lys | Leu | Gly | Ile | Met | Leu | Ile | Gly | Leu | Gly | Gly | Asn | Asn | Gly | Ser | Thr |
| 65 | | | | | 70 | | | | | 75 | | | | | 80 |

| Leu | Val | Ala | Ser | Val | Leu | Ala | Asn | Lys | His | Asn | Val | Glu | Phe | Gln | Thr |
| | | | | 85 | | | | | 90 | | | | | 95 | |

| Lys | Glu | Gly | Val | Lys | Gln | Pro | Asn | Tyr | Phe | Gly | Ser | Met | Thr | Gln | Cys |
| | | | 100 | | | | | 105 | | | | | 110 | | |

| Ser | Thr | Leu | Lys | Leu | Gly | Ile | Asp | Ala | Glu | Gly | Asn | Asp | Val | Tyr | Ala |
| | | | 115 | | | | | 120 | | | | | 125 | | |

| Pro | Phe | Asn | Ser | Leu | Leu | Pro | Met | Val | Ser | Pro | Asn | Asp | Phe | Val | Val |
| | | 130 | | | | | 135 | | | | | 140 | | | |

| Ser | Gly | Trp | Asp | Ile | Asn | Asn | Ala | Asp | Leu | Tyr | Glu | Ala | Met | Gln | Arg |
| 145 | | | | | 150 | | | | | 155 | | | | | 160 |

| Ser | Gln | Val | Leu | Glu | Tyr | Asp | Leu | Gln | Gln | Arg | Leu | Lys | Ala | Lys | Met |
| | | | | 165 | | | | | 170 | | | | | 175 | |

| Ser | Leu | Val | Lys | Pro | Leu | Pro | Ser | Ile | Tyr | Tyr | Pro | Asp | Phe | Ile | Ala |
| | | | 180 | | | | | 185 | | | | | 190 | | |

| Ala | Asn | Gln | Asp | Glu | Arg | Ala | Asn | Asn | Cys | Ile | Asn | Leu | Asp | Glu | Lys |
| | | | 195 | | | | | 200 | | | | | 205 | | |

| Gly | Asn | Val | Thr | Thr | Arg | Gly | Lys | Trp | Thr | His | Leu | Gln | Arg | Ile | Arg |
| | 210 | | | | | 215 | | | | | 220 | | | | |

```
Arg Asp Ile Gln Asn Phe Lys Glu Glu Asn Ala Leu Asp Lys Val Ile
225                 230                 235                 240

Val Leu Trp Thr Ala Asn Thr Glu Arg Tyr Val Glu Val Ser Pro Gly
            245                 250                 255

Val Asn Asp Thr Met Glu Asn Leu Leu Gln Ser Ile Lys Asn Asp His
            260                 265                 270

Glu Glu Ile Ala Pro Ser Thr Ile Phe Ala Ala Ser Ile Leu Glu
            275                 280                 285

Gly Val Pro Tyr Ile Asn Gly Ser Pro Gln Asn Thr Phe Val Pro Gly
            290                 295                 300

Leu Val Gln Leu Ala Glu His Glu Gly Thr Phe Ile Ala Gly Asp Asp
305                 310                 315                 320

Leu Lys Ser Gly Gln Thr Lys Leu Lys Ser Val Leu Ala Gln Phe Leu
                325                 330                 335

Val Asp Ala Gly Ile Lys Pro Val Ser Ile Ala Ser Tyr Asn His Leu
            340                 345                 350

Gly Asn Asn Asp Gly Tyr Asn Leu Ser Ala Pro Lys Gln Phe Arg Ser
            355                 360                 365

Lys Glu Ile Ser Lys Ser Ser Val Ile Asp Asp Ile Ile Ala Ser Asn
370                 375                 380

Asp Ile Leu Tyr Asn Asp Lys Leu Gly Lys Lys Val Asp His Cys Ile
385                 390                 395                 400

Val Ile Lys Tyr Met Lys Pro Val Gly Asp Ser Lys Val Ala Met Asp
            405                 410                 415

Glu Tyr Tyr Ser Glu Leu Met Leu Gly Gly His Asn Arg Ile Ser Ile
            420                 425                 430

His Asn Val Cys Glu Asp Ser Leu Leu Ala Thr Pro Leu Ile Ile Asp
            435                 440                 445

Leu Leu Val Met Thr Glu Phe Cys Thr Arg Val Ser Tyr Lys Lys Val
            450                 455                 460

Asp Pro Val Lys Glu Asp Ala Gly Lys Phe Glu Asn Phe Tyr Pro Val
465                 470                 475                 480

Leu Thr Phe Leu Ser Tyr Trp Leu Lys Ala Pro Leu Thr Arg Pro Gly
                485                 490                 495

Phe His Pro Val Asn Gly Leu Asn Lys Gln Arg Thr Ala Leu Glu Asn
            500                 505                 510

Phe Leu Arg Leu Leu Ile Gly Leu Pro Ser Gln Asn Glu Leu Arg Phe
            515                 520                 525

Glu Glu Arg Leu Leu
        530

<210> SEQ ID NO 74
<211> LENGTH: 1605
<212> TYPE: DNA
<213> ORGANISM: Artificial Sequence
<220> FEATURE:
<223> OTHER INFORMATION: Synthetic gene derived from Saccharomyces
      cerevisiae myo-inositol-1-phosphate synthase, having numerous
      codons replaced with others encoding the same amino acids to
      reduce free energy of folding, and a gly codon inserted after
      the initiating met codon

<400> SEQUENCE: 74
atgggtaccg aagataacat cgctccaatc acttctgtta agttgtaac tgacaaatgt      60 acttacaaag acaacgaact gctgactaaa tactcttacg aaaacgctgt agtaactaaa    120
```

```
actgcttctg gtcgtttcga tgttactccg actgttcagg actacgtatt caaactggat    180
ctgaagaaac cggaaaagct gggtatcatg ctgatcggcc tgggtggtaa caacggctct    240
actctggttg catctgttct ggcaaacaaa cacaacgtag aattccagac taaggaaggt    300
gttaaacagc cgaactactt tggttctatg actcagtgtt ctactctgaa gctgggcatt    360
gatgctgaag gtaacgacgt ttacgctccg ttcaactctc tgctgccgat ggtatctccg    420
aacgacttcg ttgtttctgg ttgggatatc aacaacgcgg atctgtacga agcaatgcag    480
cgttctcagg ttctggaata tgatctgcaa cagcgtctga aggctaagat gtctctggtt    540
aagccactgc cgtccatcta ctacccggat tttatcgcag ctaaccagga cgaacgtgct    600
aacaactgta tcaacctgga cgaaaagggt aacgttacta cccgtggtaa gtggactcac    660
ctgcagcgta tccgtcgtga tatccagaac ttcaaagagg aaaacgcact ggacaaagtt    720
atcgtactgt ggactgctaa cactgaacgt tacgtagaag tatccccggg tgtaaacgat    780
actatggaaa acctgctgca atctatcaag aacgaccacg aggaaatcgc tccgtccacc    840
atcttcgctg ctgcatctat cctggaaggc gtaccgtaca tcaacggctc tccgcagaac    900
actttcgtac cgggtctggt acagctggcg aacacgaag gtaccttcat cgctggtgac    960
gatctgaaat ctggccagac taaactgaaa tctgtactgg cacagttcct ggttgacgct   1020
ggtatcaaac cggtttctat cgcttcttat aaccacctgg gtaacaacga cggctacaac   1080
ctgtctgctc cgaaacagtt ccgttctaaa gaatctctca aatcctctgt aatcgacgac   1140
atcatcgctt ctaacgacat cctgtacaac gacaaactgg gtaagaaagt agatcactgt   1200
atcgttatca aatacatgaa accggttggt gattctaaag ttgctatgga cgaatactac   1260
tctgaactga tgctgggcgg tcacaaccgt atctctatcc acaacgtttg tgaagactct   1320
ctgctggcta ccccgctgat catcgacctg ctggttatga ctgaattctg taccgtgta   1380 tcttacaaga aagttgaccc ggttaaagaa gatgctggca aattcgaaaa cttctacccg   1440
gttctgacct tcctgtctta ctggctgaaa gctccgctga ctcgtccagg cttccacccg   1500
gttaacggtc tgaacaaaca gcgtaccgct ctggaaaact tcctgcgtct gctgatcggc   1560
ctgccgtccc agaacgaact gcgtttcgaa gaacgtctgc tgtaa            1605
```

<210> SEQ ID NO 75
<211> LENGTH: 534
<212> TYPE: PRT
<213> ORGANISM: Artificial Sequence
<220> FEATURE:
<223> OTHER INFORMATION: Synthetic protein derived from Saccharomyces
      cerevisiae myo-inositol-1-phosphate synthase, having a glycine
      residue inserted after the initiating methionine

<400> SEQUENCE: 75

Met Gly Thr Glu Asp Asn Ile Ala Pro Ile Thr Ser Val Lys Val Val
1               5                   10                  15

Thr Asp Lys Cys Thr Tyr Lys Asp Asn Glu Leu Leu Thr Lys Tyr Ser
                20                  25                  30

Tyr Glu Asn Ala Val Val Thr Lys Thr Ala Ser Gly Arg Phe Asp Val
            35                  40                  45

Thr Pro Thr Val Gln Asp Tyr Val Phe Lys Leu Asp Leu Lys Lys Pro
        50                  55                  60

Glu Lys Leu Gly Ile Met Leu Ile Gly Leu Gly Gly Asn Asn Gly Ser
65                  70                  75                  80

Thr Leu Val Ala Ser Val Leu Ala Asn Lys His Asn Val Glu Phe Gln
                85                  90                  95

-continued

```
Thr Lys Glu Gly Val Lys Gln Pro Asn Tyr Phe Gly Ser Met Thr Gln
            100                 105                 110

Cys Ser Thr Leu Lys Leu Gly Ile Asp Ala Glu Gly Asn Asp Val Tyr
        115                 120                 125

Ala Pro Phe Asn Ser Leu Leu Pro Met Val Ser Pro Asn Asp Phe Val
    130                 135                 140

Val Ser Gly Trp Asp Ile Asn Asn Ala Asp Leu Tyr Glu Ala Met Gln
145                 150                 155                 160

Arg Ser Gln Val Leu Glu Tyr Asp Leu Gln Gln Arg Leu Lys Ala Lys
                165                 170                 175

Met Ser Leu Val Lys Pro Leu Pro Ser Ile Tyr Tyr Pro Asp Phe Ile
            180                 185                 190

Ala Ala Asn Gln Asp Glu Arg Ala Asn Asn Cys Ile Asn Leu Asp Glu
        195                 200                 205

Lys Gly Asn Val Thr Thr Arg Gly Lys Trp Thr His Leu Gln Arg Ile
    210                 215                 220

Arg Arg Asp Ile Gln Asn Phe Lys Glu Glu Asn Ala Leu Asp Lys Val
225                 230                 235                 240

Ile Val Leu Trp Thr Ala Asn Thr Glu Arg Tyr Val Glu Val Ser Pro
                245                 250                 255

Gly Val Asn Asp Thr Met Glu Asn Leu Leu Gln Ser Ile Lys Asn Asp
            260                 265                 270

His Glu Glu Ile Ala Pro Ser Thr Ile Phe Ala Ala Ser Ile Leu
        275                 280                 285

Glu Gly Val Pro Tyr Ile Asn Gly Ser Pro Gln Asn Thr Phe Val Pro
    290                 295                 300

Gly Leu Val Gln Leu Ala Glu His Glu Gly Thr Phe Ile Ala Gly Asp
305                 310                 315                 320

Asp Leu Lys Ser Gly Gln Thr Lys Leu Lys Ser Val Leu Ala Gln Phe
                325                 330                 335

Leu Val Asp Ala Gly Ile Lys Pro Val Ser Ile Ala Ser Tyr Asn His
            340                 345                 350

Leu Gly Asn Asn Asp Gly Tyr Asn Leu Ser Ala Pro Lys Gln Phe Arg
        355                 360                 365

Ser Lys Glu Ile Ser Lys Ser Val Ile Asp Asp Ile Ile Ala Ser
    370                 375                 380

Asn Asp Ile Leu Tyr Asn Asp Lys Leu Gly Lys Lys Val Asp His Cys
385                 390                 395                 400

Ile Val Ile Lys Tyr Met Lys Pro Val Gly Asp Ser Lys Val Ala Met
                405                 410                 415

Asp Glu Tyr Tyr Ser Glu Leu Met Leu Gly Gly His Asn Arg Ile Ser
            420                 425                 430

Ile His Asn Val Cys Glu Asp Ser Leu Leu Ala Thr Pro Leu Ile Ile
        435                 440                 445

Asp Leu Leu Val Met Thr Glu Phe Cys Thr Arg Val Ser Tyr Lys Lys
    450                 455                 460

Val Asp Pro Val Lys Glu Asp Ala Gly Lys Phe Glu Asn Phe Tyr Pro
465                 470                 475                 480

Val Leu Thr Phe Leu Ser Tyr Trp Leu Lys Ala Pro Leu Thr Arg Pro
                485                 490                 495

Gly Phe His Pro Val Asn Gly Leu Asn Lys Gln Arg Thr Ala Leu Glu
            500                 505                 510
```

```
        Asn Phe Leu Arg Leu Leu Ile Gly Leu Pro Ser Gln Asn Glu Leu Arg
            515                 520                 525

Phe Glu Glu Arg Leu Leu
            530

<210> SEQ ID NO 76
<211> LENGTH: 2043
<212> TYPE: DNA
<213> ORGANISM: Hypomyces rosellus

<400> SEQUENCE: 76
atgaaacacc ttttaacact cgctctttgc ttcagcagca tcaatgctgt tgctgtcacc      60
gtccctcaca aggccgtagg aactggaatt cctgaaggga gtcttcagtt cctgagcctt     120
cgagcctcag cacctatcgg aagcgccatt tctcgcaaca actgggccgt cacttgcgac     180
agtgcacagt cgggaaatga atgcaacaag gccattgatg caacaaggga tacctttgg      240 cacacattct atgcgccaa cggggatcca agcccctc acacatacac gattgacatg        300
aagacaactc agaacgtcaa cggcttgtct atgctgcctc gacaggatgg taaccaaaac     360
ggctggatcg gtcgccatga ggtttatcta agctcagatg cacaaactg gggcagccct      420 gttgcgtcag gtagttggtt cgccgactct actacaaaat actccaactt tgaaactcgc     480
cctgctcgct atgttcgtct tgtcgctatc actgaagcga atggccagcc ttggactagc     540
attgcagaga tcaacgtctt ccaagctagt tcttacacag ccccccagcc tggtcttgga     600
cgctggggtc cgactattga cttaccgatt gttcctgcgg ctgcagcaat tgaaccgaca     660
tcgggacgag tccttatgtg gtcttcatat cgcaatgatg catttggagg atcccctggt     720
ggtatcactt tgacgtcttc ctgggatcca tccactggta ttgtttccga ccgcactgtg     780
acagtcacca agcatgatat gttctgccct ggtatctcca tggatggtaa cggtcagatc     840
gtagtcacag gtggcaacga tgccaagaag accagtttgt atgattcatc tagcgatagc     900
tggatcccgg gacctgacat gcaagtggct cgtgggtatc agtcatcagc taccatgtca     960
gacggtcgtg ttttttaccat ggaggctcc tggagcggtg gcgtatttga aagaatggc     1020 gaagtctata gcccatcttc aaagacatgg acgtccctac ccaatgccaa ggtcaaccca    1080
atgttgacgg ctgacaagca aggattgtac cgttcagaca accacgcgtg gctctttgga    1140
tggaagaagg gttcggtgtt ccaagcggga cctagcacag ccatgaactg gtactatacc    1200
agtggaagtg gtgatgtgaa gtcagccgga aaacgccagt ctaaccgtgg tgtagcccct    1260
gatgccatgt gcggaaacgc tgtcatgtac gacgccgtta aggaaagat cctgaccttt     1320 ggcggctccc cagattatca agactctgac gccacaacca acgcccacat catcaccctc    1380
ggtgaacccg gaacatctcc caacactgtc tttgctagca tgggttgta cttgcccga     1440 acgtttcaca cctctgttgt tcttccagac ggaagcacgt ttattacagg aggccaacga    1500
cgtggaattc cgttcgagga ttcaaccccg gtatttacac tgagatcta cgtccctgaa    1560 caagacactt tctacaagca gaaccccaac tccattgttc gcgtctacca tagcatttcc    1620
cttttgttac ctgatggcag ggtatttaac ggtggtggtg gtctttgtgg cgattgtacc    1680
acgaatcatt tcgacgcgca aatctttacg ccaaactatc tttacaatag caacggcaat    1740
ctcgcgacac gtcccaagat taccagaacc tctacacaga gcgtcaaggt cggtggcaga    1800
attacaatct cgacggattc ttcgattagc aaggcgtcgt tgattcgcta tggtacagcg    1860
acacacacgg ttaatactga ccagcgccgc attcccctga ctctgacaaa caatggagga    1920
aatagctatt cttccaagt tcctagcgac tctggtgttg cttgcctgg ctactggatg     1980
```

-continued

```
ttgttcgtga tgaactcggc cggtgttcct agtgtggctt cgacgattcg cgttactcag    2040
tga                                                                  2043
```

<210> SEQ ID NO 77
<211> LENGTH: 680
<212> TYPE: PRT
<213> ORGANISM: Hypomyces rosellus

<400> SEQUENCE: 77

```
Met Lys His Leu Leu Thr Leu Ala Leu Cys Phe Ser Ser Ile Asn Ala
1               5                   10                  15

Val Ala Val Thr Val Pro His Lys Ala Val Gly Thr Gly Ile Pro Glu
            20                  25                  30

Gly Ser Leu Gln Phe Leu Ser Leu Arg Ala Ser Ala Pro Ile Gly Ser
        35                  40                  45

Ala Ile Ser Arg Asn Asn Trp Ala Val Thr Cys Asp Ser Ala Gln Ser
    50                  55                  60

Gly Asn Glu Cys Asn Lys Ala Ile Asp Gly Asn Lys Asp Thr Phe Trp
65                  70                  75                  80

His Thr Phe Tyr Gly Ala Asn Gly Asp Pro Lys Pro His Thr Tyr
                85                  90                  95

Thr Ile Asp Met Lys Thr Thr Gln Asn Val Asn Gly Leu Ser Met Leu
            100                 105                 110

Pro Arg Gln Asp Gly Asn Gln Asn Gly Trp Ile Gly Arg His Glu Val
        115                 120                 125

Tyr Leu Ser Ser Asp Gly Thr Asn Trp Gly Ser Pro Val Ala Ser Gly
    130                 135                 140

Ser Trp Phe Ala Asp Ser Thr Thr Lys Tyr Ser Asn Phe Glu Thr Arg
145                 150                 155                 160

Pro Ala Arg Tyr Val Arg Leu Val Ala Ile Thr Glu Ala Asn Gly Gln
                165                 170                 175

Pro Trp Thr Ser Ile Ala Glu Ile Asn Val Phe Gln Ala Ser Ser Tyr
            180                 185                 190

Thr Ala Pro Gln Pro Gly Leu Gly Arg Trp Gly Pro Thr Ile Asp Leu
        195                 200                 205

Pro Ile Val Pro Ala Ala Ala Ile Glu Pro Thr Ser Gly Arg Val
    210                 215                 220

Leu Met Trp Ser Ser Tyr Arg Asn Asp Ala Phe Gly Gly Ser Pro Gly
225                 230                 235                 240

Gly Ile Thr Leu Thr Ser Ser Trp Asp Pro Ser Thr Gly Ile Val Ser
                245                 250                 255

Asp Arg Thr Val Thr Val Thr Lys His Asp Met Phe Cys Pro Gly Ile
            260                 265                 270

Ser Met Asp Gly Asn Gly Gln Ile Val Val Thr Gly Gly Asn Asp Ala
        275                 280                 285

Lys Lys Thr Ser Leu Tyr Asp Ser Ser Ser Asp Ser Trp Ile Pro Gly
    290                 295                 300

Pro Asp Met Gln Val Ala Arg Gly Tyr Gln Ser Ser Ala Thr Met Ser
305                 310                 315                 320

Asp Gly Arg Val Phe Thr Ile Gly Gly Ser Trp Ser Gly Val Phe
                325                 330                 335

Glu Lys Asn Gly Glu Val Tyr Ser Pro Ser Ser Lys Thr Trp Thr Ser
            340                 345                 350
```

```
Leu Pro Asn Ala Lys Val Asn Pro Met Leu Thr Ala Asp Lys Gln Gly
        355                 360                 365

Leu Tyr Arg Ser Asp Asn His Ala Trp Leu Phe Gly Trp Lys Lys Gly
        370                 375                 380

Ser Val Phe Gln Ala Gly Pro Ser Thr Ala Met Asn Trp Tyr Tyr Thr
385                 390                 395                 400

Ser Gly Ser Gly Asp Val Lys Ser Ala Gly Lys Arg Gln Ser Asn Arg
                405                 410                 415

Gly Val Ala Pro Asp Ala Met Cys Gly Asn Ala Val Met Tyr Asp Ala
                420                 425                 430

Val Lys Gly Lys Ile Leu Thr Phe Gly Gly Ser Pro Asp Tyr Gln Asp
            435                 440                 445

Ser Asp Ala Thr Thr Asn Ala His Ile Ile Thr Leu Gly Glu Pro Gly
        450                 455                 460

Thr Ser Pro Asn Thr Val Phe Ala Ser Asn Gly Leu Tyr Phe Ala Arg
465                 470                 475                 480

Thr Phe His Thr Ser Val Val Leu Pro Asp Gly Ser Thr Phe Ile Thr
                485                 490                 495

Gly Gly Gln Arg Arg Gly Ile Pro Phe Glu Asp Ser Thr Pro Val Phe
                500                 505                 510

Thr Pro Glu Ile Tyr Val Pro Glu Gln Asp Thr Phe Tyr Lys Gln Asn
            515                 520                 525

Pro Asn Ser Ile Val Arg Val Tyr His Ser Ile Ser Leu Leu Leu Pro
        530                 535                 540

Asp Gly Arg Val Phe Asn Gly Gly Gly Gly Leu Cys Gly Asp Cys Thr
545                 550                 555                 560

Thr Asn His Phe Asp Ala Gln Ile Phe Thr Pro Asn Tyr Leu Tyr Asn
                565                 570                 575

Ser Asn Gly Asn Leu Ala Thr Arg Pro Lys Ile Thr Arg Thr Ser Thr
                580                 585                 590

Gln Ser Val Lys Val Gly Gly Arg Ile Thr Ile Ser Thr Asp Ser Ser
            595                 600                 605

Ile Ser Lys Ala Ser Leu Ile Arg Tyr Gly Thr Ala Thr His Thr Val
        610                 615                 620

Asn Thr Asp Gln Arg Arg Ile Pro Leu Thr Leu Thr Asn Asn Gly Gly
625                 630                 635                 640

Asn Ser Tyr Ser Phe Gln Val Pro Ser Asp Ser Gly Val Ala Leu Pro
                645                 650                 655

Gly Tyr Trp Met Leu Phe Val Met Asn Ser Ala Gly Val Pro Ser Val
                660                 665                 670

Ala Ser Thr Ile Arg Val Thr Gln
        675                 680

<210> SEQ ID NO 78
<211> LENGTH: 2046
<212> TYPE: DNA
<213> ORGANISM: Artificial Sequence
<220> FEATURE:
<223> OTHER INFORMATION: Synthetic gene derived from Hypomyces rosellus
      galactose oxidase, having numerous codons replaced with others
      encoding the same amino acids to reduce free energy of folding and
      a gly codon inserted after the initiating met codon to insert a
      restriction site

<400> SEQUENCE: 78
atgggcaagc atctgctgac tctggcactg tgtttctctt ctatcaacgc tgttgctgta      60
```

-continued

```
accgttccgc ataaggctgt tggtaccggt atcccggaag gttctctgca gttcctgtct      120
ctgcgtgctt ctgctccgat cggttctgct atctctcgta caactgggc agttacctgc      180
gactccgcac agtctggtaa cgaatgcaac aaagctatcg acggtaacaa agacactttt    240
tggcacactt tctatggcgc taacggcgac ccgaaaccgc cgcacaccta ccaccatcgat   300
atgaaaacca ctcagaacgt aaacggcctg tctatgctgc cgcgccagga tggtaaccag   360
aacggttgga ttggtcgtca tgaggtatat ctgtcttccg atggtactaa ctggggttct   420
ccggtagctt ctggctcctg gttcgctgac tctaccacca aatactctaa cttcgagact   480
cgtccggcac gctatgtacg cctggttgct attactgagg caaacggtca gccgtggacc   540
tctatcgcag aaattaacgt tttccaggca tcttcttaca ccgctccgca gccgggtctg   600
ggtcgctggg gtccgactat tgacctgccg atcgttccgg cagctgctgc tattgagccg   660
acttctggtc gtgttctgat gtggtcttct taccgtaacg acgctttcgg tggttctccg   720
ggcggcatca ccctgacctc ttcttgggat ccgtctactg gcatcgtttc cgatcgtacc   780
gtaactgtta ctaagcacga tatgttttgt ccgggtattt ctatggatgg caacggccag   840
attgtagtaa ctggtggcaa cgacgctaaa aaaacctctc tgtatgattc ctcctctgat    900
tcttggatcc cgggtccgga catgcaggta gctcgcggtt atcagtcttc cgctactatg   960
tctgatggcc gtgttttcac tattggtggt tcttggtctg gcggcgtatt tgagaaaaac   1020
ggtgaagttt actctccatc ctccaaaact tggacttccc tgccgaacgc taaagttaac   1080
ccgatgctga ctgcagataa gcagggcctg taccgttccg ataaccacgc atggctgttt   1140
ggctggaaaa aaggctccgt atttcaggct ggtccgtcta ctgctatgaa ctggtactat   1200
acttctggtt ctggcgatgt taagtccgct ggcaagcgtc agtctaaccg tggcgtagca   1260
ccggatgcta tgtgcggtaa cgctgttatg tacgatgctg taaagggcaa gattctgact   1320
tttggtggct ctccggacta tcaggactcc gacgctacta ctaacgcaca tatcattact   1380
ctgggtgagc cgggtaccctc tccgaacact gtatttgcat ctaacggcct gtactttgct   1440
cgtacctttc acacctctgt agtactgccg gatggttcca cttttatcac tggcggtcag   1500
cgccgcggta ttccgttcga ggactctact ccggttttca ccccggagat ctacgtaccg   1560
gagcaggata ctttctacaa gcagaacccg aactccattg ttcgtgtata ccactctatc   1620
tctctgctgc tgccggatgg tcgtgtattt aacggtggtg gtggtctgtg tggcgactgt   1680
actactaacc atttcgatgc gcagattttt accccgaact atctgtataa ctctaacggt   1740
aacctggcaa ctcgcccgaa aattactcgc acttctaccc agtctgtaaa ggtaggcggc   1800
cgtatcacca tctctaccga ctcttctatc tctaaagctt ctctgattcg ctatggtacc   1860
gctacccata ctgtaaacac tgaccagcgt cgtatcccgc tgaccctgac caacaacggt   1920
ggtaactctt actcttttca ggttccgtct gactctggtg ttgctctgcc gggttactgg   1980
atgctgttcg ttatgaactc tgctggtgtt ccgtctgttg cttctaccat ccgtgttacc   2040
cagtag                                                                2046
```

<210> SEQ ID NO 79
<211> LENGTH: 681
<212> TYPE: PRT
<213> ORGANISM: Artificial Sequence
<220> FEATURE:
<223> OTHER INFORMATION: Synthetic protein derived from Hypomyces rosellus galactose oxidase, having a glycine residue inserted after the initiating methionine

<400> SEQUENCE: 79

```
Met Gly Lys His Leu Leu Thr Leu Ala Leu Cys Phe Ser Ser Ile Asn
 1               5                  10                  15

Ala Val Ala Val Thr Val Pro His Lys Ala Val Gly Thr Gly Ile Pro
             20                  25                  30

Glu Gly Ser Leu Gln Phe Leu Ser Leu Arg Ala Ser Ala Pro Ile Gly
             35                  40                  45

Ser Ala Ile Ser Arg Asn Asn Trp Ala Val Thr Cys Asp Ser Ala Gln
 50                  55                  60

Ser Gly Asn Glu Cys Asn Lys Ala Ile Asp Gly Asn Lys Asp Thr Phe
 65                  70                  75                  80

Trp His Thr Phe Tyr Gly Ala Asn Gly Asp Pro Lys Pro His Thr
                 85                  90                  95

Tyr Thr Ile Asp Met Lys Thr Thr Gln Asn Val Asn Gly Leu Ser Met
             100                 105                 110

Leu Pro Arg Gln Asp Gly Asn Gln Asn Gly Trp Ile Gly Arg His Glu
             115                 120                 125

Val Tyr Leu Ser Ser Asp Gly Thr Asn Trp Gly Ser Pro Val Ala Ser
 130                 135                 140

Gly Ser Trp Phe Ala Asp Ser Thr Thr Lys Tyr Ser Asn Phe Glu Thr
 145                 150                 155                 160

Arg Pro Ala Arg Tyr Val Arg Leu Val Ala Ile Thr Glu Ala Asn Gly
             165                 170                 175

Gln Pro Trp Thr Ser Ile Ala Glu Ile Asn Val Phe Gln Ala Ser Ser
             180                 185                 190

Tyr Thr Ala Pro Gln Pro Gly Leu Gly Arg Trp Gly Pro Thr Ile Asp
             195                 200                 205

Leu Pro Ile Val Pro Ala Ala Ala Ile Glu Pro Thr Ser Gly Arg
             210                 215                 220

Val Leu Met Trp Ser Ser Tyr Arg Asn Asp Ala Phe Gly Gly Ser Pro
 225                 230                 235                 240

Gly Gly Ile Thr Leu Thr Ser Ser Trp Asp Pro Ser Thr Gly Ile Val
             245                 250                 255

Ser Asp Arg Thr Val Thr Val Thr Lys His Asp Met Phe Cys Pro Gly
             260                 265                 270

Ile Ser Met Asp Gly Asn Gly Gln Ile Val Val Thr Gly Gly Asn Asp
             275                 280                 285

Ala Lys Lys Thr Ser Leu Tyr Asp Ser Ser Ser Asp Ser Trp Ile Pro
 290                 295                 300

Gly Pro Asp Met Gln Val Ala Arg Gly Tyr Gln Ser Ser Ala Thr Met
 305                 310                 315                 320

Ser Asp Gly Arg Val Phe Thr Ile Gly Gly Ser Trp Ser Gly Val
             325                 330                 335

Phe Glu Lys Asn Gly Glu Val Tyr Ser Pro Ser Ser Lys Thr Trp Thr
             340                 345                 350

Ser Leu Pro Asn Ala Lys Val Asn Pro Met Leu Thr Ala Asp Lys Gln
             355                 360                 365

Gly Leu Tyr Arg Ser Asp Asn His Ala Trp Leu Phe Gly Trp Lys Lys
             370                 375                 380

Gly Ser Val Phe Gln Ala Gly Pro Ser Thr Ala Met Asn Trp Tyr Tyr
 385                 390                 395                 400

Thr Ser Gly Ser Gly Asp Val Lys Ser Ala Gly Lys Arg Gln Ser Asn
                 405                 410                 415
```

-continued

```
Arg Gly Val Ala Pro Asp Ala Met Cys Gly Asn Ala Val Met Tyr Asp
                420             425             430

Ala Val Lys Gly Lys Ile Leu Thr Phe Gly Gly Ser Pro Asp Tyr Gln
            435             440             445

Asp Ser Asp Ala Thr Thr Asn Ala His Ile Ile Thr Leu Gly Glu Pro
        450             455             460

Gly Thr Ser Pro Asn Thr Val Phe Ala Ser Asn Gly Leu Tyr Phe Ala
465             470             475             480

Arg Thr Phe His Thr Ser Val Val Leu Pro Asp Gly Ser Thr Phe Ile
                485             490             495

Thr Gly Gly Gln Arg Arg Gly Ile Pro Phe Glu Asp Ser Thr Pro Val
            500             505             510

Phe Thr Pro Glu Ile Tyr Val Pro Glu Gln Asp Thr Phe Tyr Lys Gln
        515             520             525

Asn Pro Asn Ser Ile Val Arg Val Tyr His Ser Ile Ser Leu Leu Leu
    530             535             540

Pro Asp Gly Arg Val Phe Asn Gly Gly Gly Leu Cys Gly Asp Cys
545             550             555             560

Thr Thr Asn His Phe Asp Ala Gln Ile Phe Thr Pro Asn Tyr Leu Tyr
                565             570             575

Asn Ser Asn Gly Asn Leu Ala Thr Arg Pro Lys Ile Thr Arg Thr Ser
            580             585             590

Thr Gln Ser Val Lys Val Gly Gly Arg Ile Thr Ile Ser Thr Asp Ser
        595             600             605

Ser Ile Ser Lys Ala Ser Leu Ile Arg Tyr Gly Thr Ala Thr His Thr
    610             615             620

Val Asn Thr Asp Gln Arg Arg Ile Pro Leu Thr Leu Thr Asn Asn Gly
625             630             635             640

Gly Asn Ser Tyr Ser Phe Gln Val Pro Ser Asp Ser Gly Val Ala Leu
                645             650             655

Pro Gly Tyr Trp Met Leu Phe Val Met Asn Ser Ala Gly Val Pro Ser
            660             665             670

Val Ala Ser Thr Ile Arg Val Thr Gln
    675             680
```

SYNTHETIC GENES FOR ENHANCED EXPRESSION

CROSS-REFERENCE TO RELATED APPLICATION

This application is a continuation-in-part and claims priority of application Ser. No. 09/494,921, filed Jan. 31, 2000 now U.S. Pat. No. 6,366,860.

STATEMENT REGARDING FEDERALLY SPONSORED RESEARCH OR DEVELOPMENT

This invention was made in part with government support under Grant Nos. 1R43DK55951-01 and 1R43GM60822-01, awarded by the National Institutes of Health. The government thus has certain rights in the invention.

BACKGROUND OF THE INVENTION

The field of the invention is synthetic nucleic acid sequences for improved amplification and expression in a host organism, and methods of creating them.

It has been a goal of biotechnology to promote the expression of cloned genes for analysis of gene structure and function and also for commercial-scale synthesis of desirable gene products. DNA cloning methods have enabled the genetic modification of bacteria and unicellular eukaryotes to produce heterologous gene products. In principle, the genes may originate from almost any source, including other bacteria, animal cells or plant cells. Although this expression of heterologous genes is a function of a variety of complex factors, maximizing the expression of cloned sequences has been under intense and rapid development. Plasmid and viral vectors have been developed in both prokaryotes and eukaryotes that enhance the level of expression of cloned genes. In some cases the vector itself contains the regulatory elements controlling the expression of genes which are not normally expressed in the host cell so that a high level of expression of heterologous genes can be obtained.

Several problems exist, however, in the expression of many proteins across phyla and even across species. Post-translational handling and modification of expressed proteins by the host cell often does not mimic that of the heterologous gene's own cell type. Frequently, even if the protein is expressed in a useful form, heterologous genes are poorly expressed. Low yields of expressed protein may make manufacture of commercially useful quantities impossible or prohibitively costly. Vectors designed to enhance expression are not able to overcome some expression problems if the regulatory elements of the vector are not the constraint on robust expression. Other cellular or translational constraints are at issue.

Genes encoding poorly expressed proteins are often themselves difficult to clone and amplify as well. This can be due to secondary structure inherent in the gene, for example caused by high G-C content. Some methods have been used to reduce these difficulties, such as the use of DMSO or betaine to bring G-C and A-T melting behaviors more into alignment, or the use of ammonium sulfate (hydrogen binding cations) to destabilize G-C bonding during PCR. The problem with these methods is that the effects of the additives are concentration dependent, so variations in template size and G-C content mean lengthy optimization procedures. Additionally, these steps do nothing to facilitate subsequent expression of the nucleic acid once it has been cloned.

The frequency of particular codon usage in *Escherichia coli* and other enteric bacteria has long been known, and it has been hypothesized that replacement of certain rare codons encoding a particular amino acid in a heterologous eukaryotic or prokaryotic gene with a codon that is more commonly used by the selected host bacterium (or eukaryotic host cell) would enhance expression (see, e.g., Kane, *Curr Opin Biotechnol* 6:494–500 (1995) and Zahn, *J Bacteriol.*, 178:2926–2933 (1996)). This is based on the theory that rare codons have only a few tRNAs per cell and that transcription of heterologous sequences having numerous occurrences of these rare codons is limited by too few available tRNAs for those codons. However, simple replacement of rare codons does not reliably improve expression of heterologous genes, and no broadly applicable method exists to select which codon changes are best to increase expression of heterologous sequences. Further, it is not known in detail how codon usage is related to expression level.

Many gene products, often from bacteria, are commonly used as research and assay reagents, and various microbial enzymes increasingly are finding applications as industrial catalysts (see, for example, Rozzell, J. D., "Commercial Scale Biocatalysis: Myths and Realities," *Bioorganic and Medicinal Chemistry*, 7:2253–2261 (1999), herein incorporated by reference). Some have substantial commercial value. Examples include heat-stable Taq polymerase from *Thermus aquaticus*, restriction enzymes such as Eco RI from *E. coli*, lipase from *Pseudomonas cepacia*, β-amylase from Bacillus sp., penicillin amidase from *E. coli* and Bacillus sp., glucose isomerase from the genus *Streptomyces*, and dehalogenase from *Pseudomonas putida*. Genes from bacteria may express easily in commercially useful host strains, but many do not. In particular, genes from many bacteria have significantly different codon preferences from enteric bacteria. For example, filamentous bacteria such as streptomycetes and various strains of the genus Bacillus, Pseudomonas, and the like can be difficult to express abundantly in enteric bacteria such as *E. coli*. An example of a Pseudomonas gene that is difficult to express in *E. coli* is the enzyme methionine gamma-lyase, useful for the assay of L-homocysteine and/or L-methionine as described in U.S. Pat. No. 5,885,767 (herein incorporated by reference). This assay is particularly useful in the diagnosis and treatment of homocystinuria, a serious genetic disorder characterized by an accumulation of elevated levels of L-homocysteine, L-methionine and metabolites of L-homocysteine in the blood and urine. Homocystinuria is more fully described in Mudd et al., "Disorders of transsulfuration," In: Scriver et al., eds., *The Metabolic and Molecular Basis of Inherited Disease*, McGraw-Hill Co., New York, 7th Edition, 1995, pp. 1279–1327 (herein incorporated by reference). In developing an assay for the accurate quantitation of L-homocysteine and L-methionine according to the methods described in U.S. Pat. No. 5,885,767, obtaining large amounts of methionine gamma-lyase is necessary. However, this Pseudomonas gene contains a number of codons that are less commonly found in genes of desirable bacterial hosts for expression such as *E. coli*.

Similarly, genes from other organisms, such as yeast or mammals, can have utility as therapeutic agents, reagents, or catalysts. Examples include erythropoietin, human growth hormone, and eukaryotic oxidoreductases such as amino acid dehydrogenases, disulfide reductases, and alcohol dehydrogenases.

Because plasmid vectors designed to enhance expression with a variety of promotors or other regulatory elements often do not resolve the difficulty in expressing certain genes, and because no systematic approach exists for codon replacement to aid amplification of nucleic acids or their expression, there is clearly a need for an improved method for amplification and expression of genes, including genes from mammals and other animals, plants, yeast, fungi, and various bacteria such as *streptomycetes, Bacillus, Pseudomonas* and the like introduced into enteric bacterial hosts such as *E. coli*.

SUMMARY OF THE INVENTION

In one embodiment, the invention is directed to a method of making a synthetic nucleic acid sequence. The method comprises providing a starting nucleic acid sequence, which optionally encodes an amino acid sequence, and determining the predicted $\Delta G_{folding}$ of the sequence. The starting nucleic acid sequence can be a naturally occurring sequence or a non-naturally occurring sequence. The starting nucleic acid sequence is modified by replacing at least one codon from the starting nucleic acid sequence with a different corresponding codon to provide a modified nucleic acid sequence. As used herein, "codon" generally refers to a nucleotide triplet which codes for an amino acid or translational signal (e.g., a stop codon), but can also mean a nucleotide triplet which does not encode an amino acid, as would be the case if the synthetic or modified nucleic acid sequence does not encode a protein (e.g., upstream regulatory elements, signaling sequences such as promotors, etc.). As used herein, a "different corresponding codon" refers to a codon which does not have the identical nucleotide sequence, but which encodes the identical amino acid. The predicted $\Delta G_{folding}$ of the modified nucleic acid sequence is determined and compared with the $\Delta G_{folding}$ of the starting nucleic acid sequence. In accordance with the invention, the predicted $\Delta G_{folding}$ of the starting nucleic acid sequence can be determined before or after the modified starting nucleic acid is provided.

Thereafter, it is determined whether the $\Delta G_{folding}$ of the modified nucleic acid sequence is increased relative to the $\Delta G_{folding}$ of the starting nucleic acid sequence by a desired amount, such as at least about 2%, at least about 10%, at least about 20%, at least about 30%, or at least about 40%. If the $\Delta G_{folding}$ of the modified nucleic acid sequence is not increased by the desired amount, the modified nucleic acid sequence is further modified by replacing at least one codon from the modified nucleic acid sequence with a different corresponding codon to provide a different modified nucleic acid sequence. These steps are repeated until the $\Delta G_{folding}$ of the modified nucleic acid sequence is increased by the desired amount to ultimately provide a final nucleic acid sequence, which is the desired nucleic acid sequence.

In one embodiment, the invention is a synthetic polynucleotide designed by the methods of the invention. This includes a nucleic acid having the sequence of a polynucleotide designed by the methods or a sequence complementary thereto.

In another embodiment, the invention includes a method of physically creating a tangible synthetic polynucleotide comprising creating a physical embodiment of the synthetic polynucleotide made using the nucleic acid/polynucleotide design methods of the invention, and the physical embodiments of the tangible synthetic polynucleotide prepared by this method (i.e., physical embodiments of the synthetic sequences, and copies of such sequences created by other methods.

The modified and/or final nucleic acid sequence can then be physically created. By the present invention, a desired nucleic acid sequence can be created that is more highly expressed in a selected host, such as *E. coli*, an insect cell, yeast, or a mammalian cell, than the starting sequence. By "more highly expressed" is meant more protein product is produced by the same host than would be with the starting sequence, preferably at least 5% more, more preferably at least 10% more, and most preferably at least 20% more.

Preferably the codon replacement is in a region of the starting nucleic acid sequence or modified nucleic acid sequence containing secondary structure. It is also preferred that the different corresponding codon is one that occurs with higher frequency in the selected host. In a particularly preferred embodiment, the desired amino acid sequence is expressed in *Escherichia coli*, and the amino acid sequence is from a bacterium of the genus *Pseudomonas*, and the different corresponding codon is selected to be one that occurs with higher frequency in a selected host, such as *Escherichia coli* than does the replaced codon. Alternatively, or in addition, the different corresponding codon is selected as one that has fewer guanine or cytosine residues than the replaced codon.

In a particularly preferred embodiment, the starting nucleic acid sequence is derived, e.g., converted, from an amino acid sequence native to an organism different from the desired host for expression, for example *Pseudomonas*.

The method of the invention also provides a modified, final sequence that is more amplifiable than the starting sequence. In other words, the final sequence is amplified more readily in a full length form, more rapidly or in greater quantity.

In another embodiment, the invention is directed to a synthetic nucleic acid sequence having a plurality of codons and encoding a methionine gamma-lyase protein from *Pseudomonas putida*. As used herein, the phrase "nucleic acid sequence encoding a protein" means that the nucleic acid sequence encodes at least the functional domain of the protein. The sequence having no more than about 95% homology, preferably no more than about 90% homology, more preferably no more than about 85% homology, still more preferably no more than about 80% homology, to a naturally occurring methionine gamma-lyase gene from *Pseudomonas putida*. At least about 5%, preferably at least about 10%, more preferably at least about 20%, still more preferably at least about 30%, even more preferably at least about 40%, of the codons in the synthetic nucleic acid sequence are different from codons found in the naturally occurring gene.

In one aspect, the codons in the synthetic nucleic acid sequence encode the same amino acids as the codons in the naturally occurring gene. In another aspect, at least one of the codons in the synthetic nucleic acid sequence encodes an amino acid different from the numerically corresponding amino acid found in the naturally occurring sequence. In yet another aspect, at least one of the different codons in the synthetic nucleic acid sequence is in an area of secondary structure in the naturally occurring gene.

In another embodiment, the invention is directed to synthetic genes derived from any source, e.g., eukaryotic or prokaryotic, for improved expression in heterologous or homologous expression hosts. The synthetic nucleic acid sequences of the invention are comprised on non-naturally occurring polymers of nucleic acids, each sequence having a biological function encoded by the sequence. The biological function can be direct (e.g., the nucleic acid sequence possesses the function, as in a promotor, for example) or indirect (e.g., the nucleic acid serves as a template to encode another molecule such as RNA or protein which has a function), and is generally one that is known from a similar naturally occurring or synthetic sequence. However, the biological function of the synthetic sequence created using the methods of the invention need not be identical to a known or predicted biological function in a known starting sequence. For example, the function may be enhanced in the synthetic sequence, or an enzyme may act on one or more different substrates, use more or different co-factors, catalyze reactions at a different rate, etc. The synthetic sequences further have no more than about 95% homology to a known starting sequence, and have a different free energy of folding than does the starting sequence. Finally, the synthetic sequences of the invention have the characteristic that they are better expressed (e.g., more highly expressed, expressed under different conditions, or expressed with more desired characteristics) in a selected host cell than the starting sequence would be if expressed in the selected host cell. The host cell is generally heterologous, but may be homologous for the starting sequence (the artificial synthetic sequence, not being found in nature, has no homologous host).

In one aspect, the synthetic nucleic acid sequence comprises a plurality of codons which encode amino acids and proteins. In preferred embodiments, the difference between the synthetic sequence and the starting sequence is that the synthetic sequence has at least one codon which is different from the starting sequence at the same amino acid position in the protein sequence. This codon may encode a different amino acid, the same amino acid, insert or delete an amino acid from that position, or encode a restriction site. Members of the oxidoreductase family are disclosed, and all members of this family or sequences encoding oxidoreductase functionality are among preferred sequences. Other preferred sequences include those encoding decarboxylase, formate dehydrogenase, hydantoinase, and vanillyl alcohol oxidase functions. Any sequence encoding a biological function from any source can be improved using the methods of the invention for enhanced expression or functionality.

In another embodiment, the invention is directed to a method of creating a synthetic nucleic acid. The method comprises providing a sense nucleic acid sequence having a 5' end and a 3' end and providing an antisense nucleic acid sequence having a 5' end and a 3' end. Preferably the sense and antisense nucleic acid sequences are between about 10 and about 200 bases, more preferably between about 80 and about 120 bases. The 3' end of the sense sequence has a plurality of bases complimentary to a plurality of bases of the 3' end of the antisense sequence, thereby forming an area of overlap. Preferably the area of overlap is at least 6 bases, more preferably at least 10 bases, still more preferably at least 15 bases. The 5' end of the sense sequence extends beyond the 3' end of the antisense sequence, and the 5' end of the antisense sequence extends beyond the 3' end of the sense sequence. The method further comprises annealing the sense and antisense sequences at the area of overlap. A polymerase and free nucleotides are added to the sequences. Said nucleotides may be naturally occurring, i.e., A, T, C, G, or U, or they may be non-natural, e.g., iso-cytosine, iso-guanine, xanthine, and the like. The sequences can be annealed before or after addition of the polymerase and free nucleotides. The sequences are extended, wherein the area of overlap serves to prime the extension of the sense and antisense sequences in the 3' direction, forming a double stranded product. The extended sequence can then be amplified. Further, a second step to the method can be added where the double stranded first extension product is separated into an extended sense strand and an extended antisense strand and a second set of sense and antisense nucleic acid sequences are provided having a 5' end and a 3' end. Each has a plurality of bases on its 3' end complementary to a plurality of bases on the 3' end of the extended sense or antisense strand respectively, thereby forming second and third areas of overlap. A polymerase and free nucleotides are added to the sequences and separated strands, wherein the second and third areas of overlap serve to prime a second extension of the sequences and strands that encompasses the sequence of the first sense and antisense nucleic acid sequences and the second sense and antisense nucleic acid sequences.

DESCRIPTION OF THE DRAWINGS

These and other features and advantages of the present invention will be better understood by reference to the following detailed description when considered in conjunction with the accompanying figures wherein:

FIG. 1A: DNA sequence of synthetic mdeA gene (1200 bps with GCT insertion; SEQ ID NO. 3), called synmdeA. Nco I and BamH I cloning sites are engineered at 5= end and 3= end. The bold face uppercase nucleotides are the changed nucleotides from the original mdeA gene sequence.

FIG. 1B: First DNA segment, mdeA1 (426 bps; SEQ ID NO. 4), with Nco I and Pst I cloning sites.

FIG. 1C: Second segment, mdeA2 (414 bps; SEQ ID NO. 6), with Pst I and EcoR I cloning sites.

FIG. 1D: Third segment, mdeA3 (367 bps; SEQ ID NO. 8), with EcoR I and BamH I cloning sites.

FIG. 2A: First round of amplification using long oligonucleotides to generate template (tpA1, tpA2, or tpA3) DNA for each of the three synmdeA segments mdeA1, mdeA2 or mdeA3. PCR amplification relies on overlapping sections of each oligonucleotide, which serves to prime the extension of the neighboring segment.

FIG. 2B: Second round of amplification using the two short oligonucleotides to amplify the full-length segments, mdeA1, mdeA2 or mdeA3. The short oligonucleotides overlap with the 5' ends of the sense and antisense strands to form a template primed by the tpA1, tpA2, or tpA3 strands, resulting in the filling in of both 5' and 3' ends of mdeA1, mdeA2 and mdeA3 after the second round of PCR.

FIG. 4A is a gel showing expression of a synthetic *P. putida* methionine gamma lyase synmdeA in BL21/pTM vector prior to and after induction with IPTG. All cultures were grown at 37° C. synmdeA was cloned into pET15b (available from Novagen) under the control of T7 RNA polymerase promotor. Lanes are: M—prestained protein molecular weight standards, high range, as indicated on the figure; 1 and 2—three hours induction with 0.1 mM IPTG; 3—three hours induction with 0.5 mM IPTG; 4—three hours induction with 1 mM IPTG; 5—three hours induction with 2 mM IPTG; 6—not induced.

FIG. 4B is a gel showing the poor expression of native *P. putida* methionine gamma lyase (mdeA) in pSIT vector prior to and after induction with IPTG. All cultures were grown at 37° C. The induced samples contain extra bands at about 28 kD due to premature termination of mdeA translation.

Native mdeA was cloned into the pSIT vector under the control of the T7 RNA polymerase promotor. Lanes are: M—prestained protein molecular weight standards, high range, as indicated on the figure; 1—not induced; 2 and 3—three hours induction with 0.5 mM IPTG; 4 and 5—three hours induction with 1 mM IPTG.

FIG. 5 shows expression in *E. coli* of two genes with very different $\Delta G_{folding}$, naphthalene dioxygenase (NDO) from *Pseudomonas putida* ($\Delta G$=−256.1 kcal/mol) and methionine gamma lyase (mgl I) from *T. vaginalis* ($\Delta G$=−152.5 kcal/mol). Lanes 1–4 are NDO products, and 5–9 are MGL 1 products. Lanes are as follows: M1—multimark multi-colored standard; M2—prestained protein molecular weight standards; 1—not induced; 2—three hours induction with 0.02% L-arabinose; 3—three hours induction with 0.04% L-arabinose; 4—three hours induction with 0.08% L-arabinose; 5—not induced; 6—three hours induction with 0.02% L-arabinose; 7—three hours induction with 0.04% L-arabinose; 8—three hours induction with 0.08% L-arabinose; 9—three hours induction with 0.10% L-arabinose. Both genes were cloned into the pBAD vector. Cells were grown at 37° C. Expression of mgl I, having a less negative $\Delta G_{folding}$ was superior to NDO expression.

Figure 6:
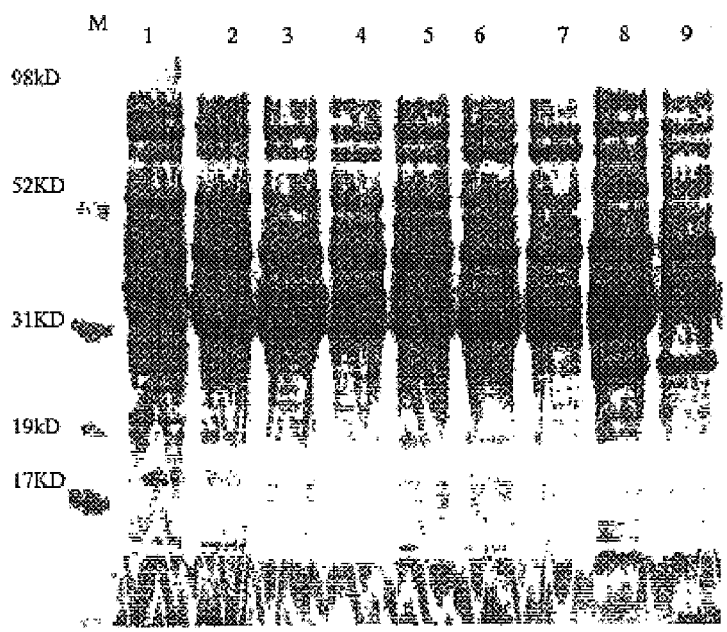

FIG. 6 is a gel showing expression of native and synthetic genes developed using the methods of the invention. Lane 1 is a negative control (empty pBAD vector); Lanes 2 and 3 show expression of synthetic aldehyde reductase 2 containing an A25 to G25 mutation (synALR2mut) induced at 30° C. and 37° C., respectively; Lanes 4 and 5 show expression of native yeast putative reductase 1 (YPR1) induced at 30° C. and 37° C., respectively; Lanes 6 and 7 show the synthetic version, synYPR1, induced at 30° C. and 37° C., respectively; and Lanes 8 and 9 show expression of synthetic aldehyde reductase 1 (synALR1) induced at 30° C. and 37° C., respectively. All sequences except synALR1 were induced for 3 hours with L-arabinose. synALR1 was cloned into a different vector and induced for 3 hours with IPTG.

Figure 7:
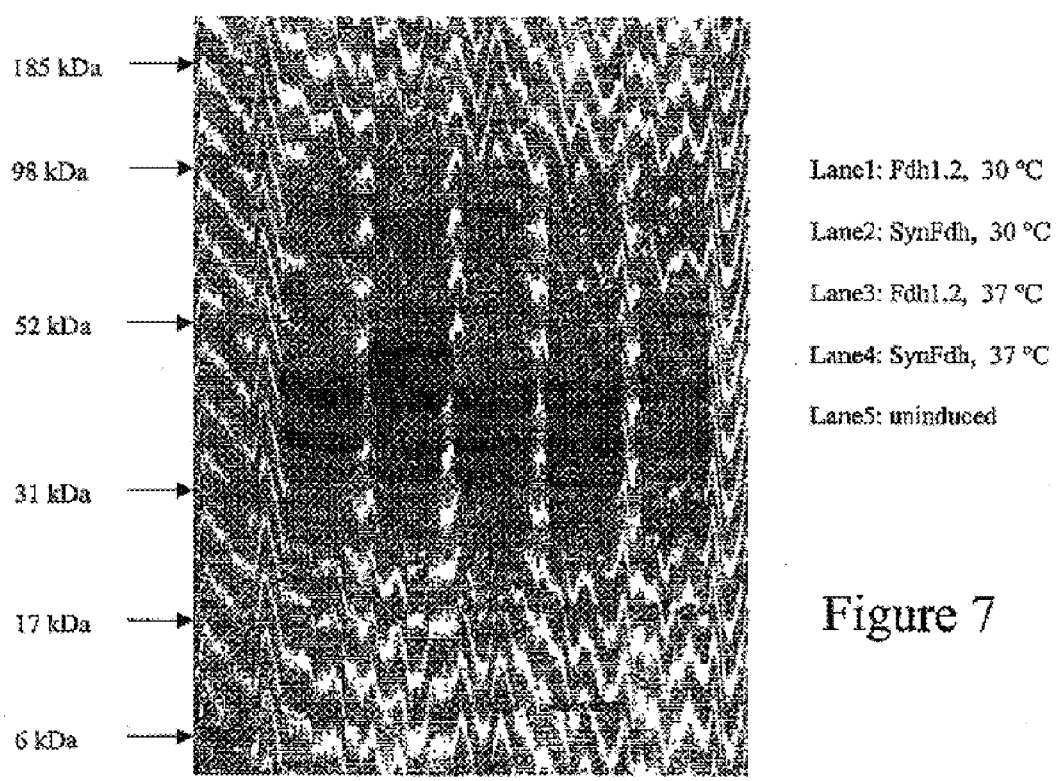

FIG. 7 is a gel comparing expression of native and synthetic formate dehydrogenase (Fdh1.2 and synFdh, respectively) induced with L-arabinose for 3 hours at 30° C. and 37° C., and uninduced. Lane 1 is Fdh1.2 induced at 30° C.; Lane 2 is synFdh at 30° C.; Lane 3 is Fdh1.2 at 37° C.; Lane 4 is synFdh at 37° C.; and Lane 5 is uninduced Fdh1.2.

Figure 8:
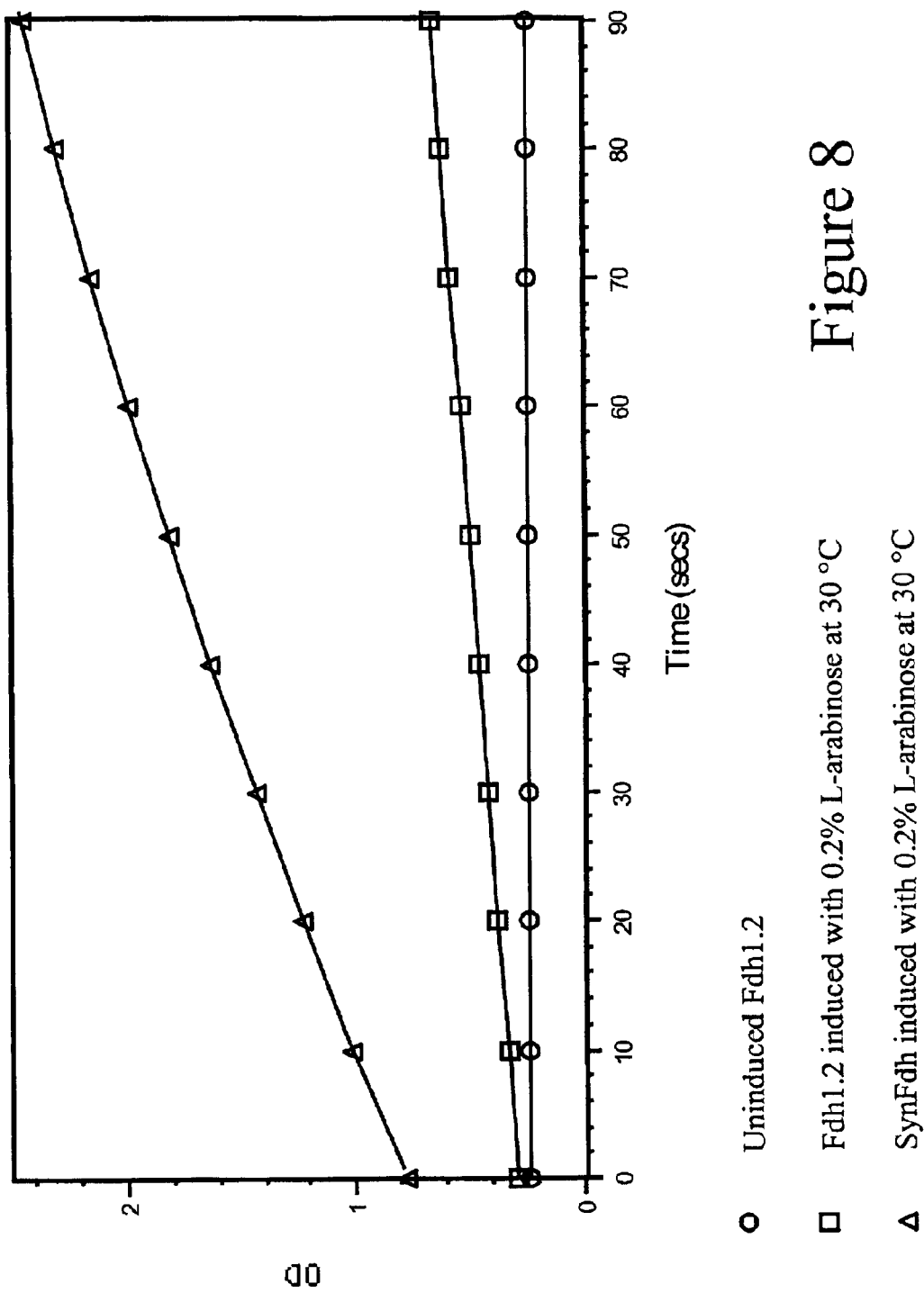

FIG. 8 graphically represents enzyme activity of synthetic formate dehydrogenase (synFdh) created using the methods of the invention (open triangles) as compared to native Fdh1.2 (open squares, induced; open circles uninduced), using an assay to catalyze the oxidation of formate in the presence of $NAD^+$.

DETAILED DESCRIPTION OF THE INVENTION

In one embodiment, the invention is directed to developing nucleic acid sequences that enhance expression of the encoded protein in a heterologous host. The frequency of particular codon usage for *E. coli* and other enteric bacteria is shown in Table 1, below. This table is derived from the 2000 Novagen Catalog, page 196, herein incorporated by reference. However, the information in this table does not tell one of skill in molecular biology which codons should be replaced to enhance expression, if indeed any replacements will enhance expression. Considerations other than simple codon replacement are clearly important. It has been discovered that the composition of the full gene (or fragment to be expressed) is more important than a particular codon exchange, and heterologous expression can be enhanced by replacement of codons in the sequence's open reading frame alone, independent of promotors or other regulatory sequence.

TABLE 1

| aa | Codon | /1000[1] | Fraction[2] | aa | Codon | /1000[1] | Fraction[2] |
|---|---|---|---|---|---|---|---|
| Gly | GGG | 1.89 | 0.02 | Trp | UGG | 7.98 | 1.00 |
| Gly | GGA | 0.44 | 0.00 | stop | UGA | 0.00 | (stop) |
| Gly | GGU | 52.99 | 0.59 | Cys | UGU | 3.19 | 0.49 |
| Gly | GGC | 34.55 | 0.38 | Cys | UGC | 3.34 | 0.51 |
| Glu | GAG | 15.68 | 0.22 | stop | UAG | 0.00 | (stop) |
| Glu | GAA | 57.20 | 0.78 | stop | UAA | 0.00 | (stop) |
| Asp | GAU | 21.63 | 0.33 | Tyr | UAU | 7.40 | 0.25 |
| Asp | GAC | 43.26 | 0.67 | Tyr | UAC | 22.79 | 0.75 |
| Val | GUG | 13.50 | 0.16 | Leu | UUG | 2.61 | 0.03 |
| Val | GUA | 21.20 | 0.26 | Leu | UUA | 1.74 | 0.02 |
| Val | GUU | 43.26 | 0.51 | Phe | UUU | 7.40 | 0.24 |
| Val | GUC | 5.52 | 0.07 | Phe | UUC | 24.10 | 0.76 |
| Ala | GCG | 23.37 | 0.26 | Ser | UCG | 2.03 | 0.04 |
| Ala | GCA | 25.12 | 0.28 | Ser | UCA | 1.02 | 0.02 |
| Ala | GCU | 30.78 | 0.35 | Ser | UCU | 17.42 | 0.34 |
| Ala | GCC | 9.00 | 0.10 | Ser | UCC | 19.02 | 0.37 |
| Arg | AGG | 0.15 | 0.00 | Arg | CGG | 0.15 | 0.00 |
| Arg | AGA | 0.00 | 0.00 | Arg | CGA | 0.29 | 0.01 |
| Ser | AGU | 1.31 | 0.03 | Arg | CGU | 42.10 | 0.74 |
| Ser | AGC | 10.31 | 0.20 | Arg | CGC | 13.94 | 0.25 |
| Lys | AAG | 16.11 | 0.26 | Gln | CAG | 33.83 | 0.86 |
| Lys | AAA | 46.46 | 0.74 | Gln | CAA | 5.37 | 0.14 |
| Asn | AAU | 2.76 | 0.06 | His | CAU | 2.61 | 0.17 |
| Asn | AAC | 39.78 | 0.94 | His | CAC | 12.34 | 0.83 |
| Met | AUG | 24.68 | 1.00 | Leu | CUG | 69.69 | 0.83 |
| Ile | AUA | 0.15 | 0.00 | Leu | CUA | 0.29 | 0.00 |
| Ile | AUU | 10.16 | 0.17 | Leu | CUU | 3.63 | 0.04 |
| Ile | AUC | 50.09 | 0.83 | Leu | CUC | 5.52 | 0.07 |
| Thr | ACG | 3.63 | 0.07 | Pro | CCG | 27.58 | 0.77 |
| Thr | ACA | 2.03 | 0.04 | Pro | CCA | 5.23 | 0.15 |
| Thr | ACU | 18.87 | 0.35 | Pro | CCU | 2.76 | 0.08 |
| Thr | ACC | 29.91 | 0.55 | Pro | CCC | 0.15 | 0.00 |

[1]Expected number of occurrences per 1000 codons in enteric bacterial genes whose codon usage is identical to that compiled in the frequency table.
[2]Fraction of occurrences of the codon in its synonymous codon family.

The present invention encompasses highly amplifiable, expressible oligonucleotides, polynucleotides, and/or genes and is directed to methods of designing and physically creating these nucleic acid sequences. In one embodiment, the present invention is directed to a method of designing and physically creating genes that express well when introduced into heterologous expression hosts, such as from eukaryotic sources into prokaryotic hosts, e.g., common enteric bacterial host microorganisms such as *E. coli*. The invention allows expression of genes from various organisms, such as mammals and other animals, plants, yeast, fungi, and bacteria (e.g., pigs, Saccharomyces, streptomycetes, Bacillus, Pseudomonas and the like) in prokaryotic hosts such as *E. coli* and eukaryotic hosts at commercially viable levels, even proteins with typically low yields, such as methionine gamma-lyase from *P. putida*. As used herein, the terms "polypeptide," "protein" and "amino acid sequence" are used interchangeably and mean oligomeric polyamides of at least two amino acids, whether or not they encompass the full-length polypeptide encoded by a gene or merely a portion of it. "Heterologous" indicates that the sequence is not native to the host used or identical to a sequence which naturally occurs in the host used, or refers to a host which is not the natural source of a nucleic acid or peptide sequence. "Designing" means conceiving a sequence of nucleotides in a form that can be written or printed. Such sequence may correspond to the coding region of an entire gene, or only a portion of it, and may also include additional bases added at a particular location or position, for example to create desired restriction sites or to insert mutations to enhance the protein's function. "Physically creating" means preparing a chemical entity such as an oligonucleotide/polynucleotide or polypeptide, whether by synthesis by chemical and/or enzymatic methods, biosynthesis, a combination of synthesis and PCR, or by any other methods known in the art. "PCR" means polymerase chain reaction.

In the present invention, the sequence of a gene is modified to enhance its ability to be amplified, for example by PCR methods, and/or to improve its expression in a selected host, for example, an enteric bacterium such as $E.$ $coli$. This is achieved by designing a nucleotide sequence preferably using codons preferred by the host, calculating the $\Delta G_{folding}$ of the nucleic acid sequence (the amount of energy required for or released by folding in solution, in kcal/mole), modifying the sequence by replacing one or more codons in the sequence in one or more areas of predicted secondary structure with less preferred codons to reduce predicted secondary structure, and recalculating the $\Delta G_{folding}$ of the modified nucleic acid sequence. The replacement of codons and recalculation of the free energy of folding may be repeated as many times as desired. One, some, or all codons encoding a particular amino acid may be replaced in the region of secondary structure, or throughout the entire coding region of the sequence. The result is a modified final nucleic acid sequence, for example a synthetic gene encoding a desired complete or partial protein, whether a mutant protein or one having the desired structural and functional attributes of a native protein. The final synthetic sequence may be optimized for only a single selected host, but the methods of the invention are readily operably for a starting sequence from any source for expression in any selected host, whether animal, plant, fungal, prokaryotic, etc.

As used herein, the term "synthetic" gene, nucleic acid, oligonucleotide, polynucleotide, primer, or the like means a nucleic acid sequence that is not found in nature; in other words, not merely a heterologous sequence to a particular organism, but one which is heterologous in the sense that it has been designed and/or created in a laboratory, and is altered in some way, and that it does not have exactly the nucleotide (or possibly amino acid) sequence that its naturally occurring source, template, or homolog has. A synthetic nucleic acid or amino acid sequence as used herein can refer to a theoretical sequence or a tangibly, physically created embodiment. It is intended that synthetic sequences designed by the method be included in the invention in any form, e.g., paper or computer readable ("theoretical"), and physically created nucleic acids or proteins. Physically created nucleic acids and proteins of the invention are part of the invention, whether derived directly from the designed sequence, or copies of such sequences (e.g., made by PCR, plasmid replication, chemical synthesis, and the like). The term "synthetic nucleic acid" can include, for example, nucleic acid sequences derived or designed from wholly artificial amino acid sequences, or nucleic acid sequences with single or multiple nucleotide changes as compared to the naturally occurring sequence, those created by random or directed mutagenesis, chemical synthesis, DNA shuffling methods, DNA reassembly methods, or by any means known to one of skill in the art (see e.g., techniques described in Sambrook and Russell, "Molecular Cloning; A Laboratory Manual," $3^{rd}$ Ed., Cold Spring Harbor Laboratory Press (2001), herein incorporated by reference). Such alterations can be done without changing the amino acid sequence encoded by the nucleic acid sequence, or can modify the amino acid sequence to leave a desired function of the encoded protein unaltered or enhanced. As used herein, "nucleic acid" means a naturally occurring or synthetic nucleic acid, which can be composed of natural or synthetic nitrogen bases, a deoxyribose or ribose sugar, and a phosphate group.

"Secondary structure" refers to regions of a nucleic acid sequence that, when single stranded, have a tendency to form double-stranded hairpin structures or loops. Such structures impede transcription (or amplification in vitro) and translation of affected regions in the nucleic acid sequence. Nucleic acids can be evaluated for their likely secondary structure by calculating the predicted $\Delta G_{folding}$ of each possible structure that could be formed in a particular strand of nucleic acid. Energy must be released overall to form a base-paired structure, and a structure's stability is determined by the amount of energy it releases. The more negative the $\Delta G_{folding}$ (i.e., the lower the free energy), the more stable that structure is and the more likely the formation of that double-stranded structure.

Computer programs exist that can predict the secondary structure of a nucleic acid by calculating its free energy of folding. One example is the mfold program, which can be found at http://mfold2.wustl.edu/~mfold/dna/form1.cgi (using free energies derived from SantaLucia $Proc. Natl.$ $Acad. Sci. USA$ 95:1460–1465 (1998); see also Zuker, $Science,$ 244, 48–52, (1989); Jaeger et al., $Proc. Natl. Acad.$ $Sci.$ USA, Biochemistry, 86:7706–7710 (1989); Jaeger et al., Predicting Optimal and Suboptimal Secondary Structure for RNA. in "Molecular Evolution: Computer Analysis of Protein and Nucleic Acid Sequences", R. F. Doolittle ed., $Methods\ in\ Enzymology,$ 183, 281–306 (1989); all herein incorporated by reference). Another example of such a computer program is the Vienna RNA Package, available at http://www.ks.uiuc.edu/~ivo/RNA/, which predicts secondary structure by using two kinds of dynamic programming algorithms: the minimum free energy algorithm of Zuker and Stiegler ($Nucl. Acid. Res.$ 9: 133–148 (1981)) and the partition function algorithm of McCaskill ($Biopolymers$ 29, 1105–1119 (1990)). Distances (dissimilarities) between secondary structures can be computed using either string alignment or tree-editing (Shapiro & Zhang 1990). Finally, an algorithm is provided to design sequences with a predefined structure (inverse folding).

Modifications to reduce secondary structure in DNA sequences by altering codon usage can be made in several ways. As used herein, "replacing codons" or "altering codon usage" means altering at least one of the nucleotides making up the three nucleotides of the codon triplet. It is understood that this change can occur at a "wobble" position to leave the amino acid encoded unchanged, or at another position or to a base that results in a change in the encoded amino acid. For example, the codon changes can be designed to swap out codons for a particular amino acid in the sequence (e.g., at a designated position in the sequence) which are not common in the selected host (following e.g., Kane, supra, or Zahn, supra). Further, codons can be replaced to reduce the G-C content of the naturally occurring codon.

The inventive methods of the present invention produce sequences with superior expression characteristics because they take more than one variable into account. The methods involve designing a nucleic acid sequence based on a desired amino acid sequence using the codons most commonly used for each amino acid in the chosen host organism (of course, an additional step of analyzing the $\Delta G_{folding}$ of a native sequence may be performed as well). Next, the predicted free energy of folding for the designed sequence is calculated using a computer program as described previously. The program mfold is used in the Examples provided herein, although any similar program may be used in the practice of this invention. In calculating the predicted $\Delta G_{folding}$ the full-length nucleotide sequence can be analyzed as a single entity, or the full-length sequence can be divided into shorter segments and the predicted $\Delta G_{folding}$ for each segment can be calculated separately, and then added together.

After the predicted $\Delta G_{folding}$ is calculated, changes to the sequence are made to try to reduce the formation of secondary structure. Regions of predicted secondary structure are identified using, for example, one of the computer programs previously described, and changes are made in codons in these identified regions. Preferably, codon changes are selected to favor more frequently occurring codons in the host organism selected to express the synthetic gene. Thus, one or more codons in regions of predicted high secondary structure are changed to the second or third most commonly used codon choice for the chosen host organism, and the predicted $\Delta G_{folding}$ is recalculated. This process of codon changes and recalculation of the predicted $\Delta G_{folding}$ is repeated until the predicted $\Delta G_{folding}$ of the sequence examined (e.g., the entire sequence or a portion) is increased (made less negative) by greater than about 2%, preferably greater than about 10%, more preferably greater than about 30%, as calculated by $\Delta G_{folding}$/(number of bases in the sequence analyzed). The starting sequence for the step of designing a sequence (e.g., the naturally occurring sequence) is set as 100%. It is likely that the change in $\Delta G_{folding}$ between the starting sequence and the final product will be smaller when the starting sequence is a completely synthetic sequence based solely on preferred codon usage than when the starting sequence is a naturally occurring sequence from a heterologous organism. $\Delta G_{folding}$ for segments analyzed separately can be added to arrive at a $\Delta G_{folding}$ for the entire sequence, or the $\Delta G_{folding}$ for the entire sequence can be determined in a single calculation. Once the $\Delta G_{folding}$ for the entire sequence has been so determined, it is divided by the sequence length in bases to arrive at a uniform measure of $\Delta G_{folding}$ for comparison of sequences of unequal length.

It is also possible that a synthetic sequence may have a more negative $\Delta G_{folding}$ than its counterpart native sequence. This condition may occur when codon choices must be made to accommodate a particular expression host, or when the native sequence has very little secondary structure to begin with. Preferably, this situation occurs in cases where the native sequence does not have a great deal of secondary structure (see, e.g., Example 9 and Fdh2.1 and SynFdh). Regardless, in such cases, the difference in $\Delta G$/base between the native sequence and the more negative synthetic sequence is preferably less than 0.1 kcal/(mol)(base), more preferably less than 0.05 kcal/(mol)(base), and most preferably less than about 0.03 kcal/(mol)(base).

Several variants can be analyzed to illustrate the advantages of the inventive method, summarized in Table 2 below. A naturally occurring (native) mdeA gene from P. putida (SEQ. ID NO. 1) was used as the starting sequence, and its $\Delta G_{folding}$ was calculated (all $\Delta G_{folding}$ results reported herein were carried out assuming a temperature of 37° C., Na$^+$=1 M, and Mg$^{++}$=0) and set at 100%. This sequence was modified by replacing rare arginine codons (termed "repmdeA;" modifications derived from Zahn, supra) with one found most commonly in E. coli (SEQ ID NO. 28). The change in $\Delta G_{folding}$/base from this replacement was 1.9%. A more significant alteration of mdeA was performed by replacing all of the rare codons mentioned in Kane, supra. This sequence was made by exchanging agg, aga, and cga codons with cgt (arginine), cta codons with ctg (leucine), ata with atc (isoleucine), and ccc with ccg (proline) (termed "raremdeA;" SEQ ID NO. 29). As seen in Table 2, below, this exchange also did not significantly impact the $\Delta G$ of the sequence, resulting in a change in $\Delta G_{folding}$/base of only 1% as compared to the native sequence. Simply replacing a rare codon does not necessarily increase $\Delta G_{folding}$, and in fact, could lower $\Delta G_{folding}$ creating or failing to resolve problems in transcription or translation, or in amplification by PCR methods.

Because the codons known in the art to be rare and potentially to have an impact on expression did not significantly improve the $\Delta G_{folding}$ of the sequence, all codons of mdeA's open reading frame were exchanged for the most common codons in enteric bacteria from Table 1, above (a sequence termed "optmdeA;" SEQ ID NO. 30). The $\Delta G_{folding}$ of this sequence was increased 31.8% by this change compared to mdeA, a significant improvement. However, when the sequence optmde A was analyzed for regions of predicted secondary structure, replacements of codons in areas of high secondary structure were made to generate the designed sequence synmdeA (SEQ ID NO. 3). The predicated $\Delta G_{folding}$ was recalculated for this sequence, and a superior sequence with a greatly improved $\Delta G_{folding}$ was created. In this case, $\Delta G_{folding}$ was increased (made less negative) by 40.7% compared to the starting native sequence. Thus, it is clear that the inventive methods of developing the synthetic sequences go well beyond any suggestions in the art pertaining to codon exchange.

TABLE 2

| Sequence | $\Delta G$ (kcal/mol) | $\Delta G$/base | % Change in $\Delta G$ |
| --- | --- | --- | --- |
| mdeA (1197 bp) | −256.6 | −0.214 | 0% |
| repmdeA (1197 bp) | −251.8 | −0.210 | 1.9% |
| raremdeA (1197 bp) | −254.0 | −0.212 | 1.0% |
| optmdeA (1200 bp) | −175.5 | −0.146 | 31.8% |
| synmdeA (1200 bp) | −152.5 | −0.127 | 40.7% |

The method described herein of formulating synthetic sequences for improved expression can be used for any nucleic acid sequence, even those being expressed in homologous hosts, or with relatively little predicted secondary structure. Most commonly, however, the need to improve expression will arise when expressing proteins in heterologous hosts. Regardless, any starting sequence, preferably with a $\Delta G_{folding}$/base of about −0.05 kcal/(mole)(base) or less, and more preferably with $\Delta G_{folding}$/base of about −0.15 kcal/(mole)(base) or less, and most preferably with a $\Delta G_{folding}$/base of −0.2 kcal/(mole)(base) or less can be improved for better expression using the methods of the invention. When a $\Delta G_{folding}$ less than about −0.20 kcal/(mole)(base) or an increase of at least about 2% from the starting sequence is reached, the actual sequence of the synthetic DNA can be physically created. Such physical creation of the designed oligonucleotide sequence can be accomplished by any of the methods known in the prior art, for example by oligonucleotide synthesis, or by the nucleic acid synthesis methods of the invention (described more fully below).

Additionally, the invention takes advantage of the improved secondary structure characteristics of the synthetic nucleic acid for enhanced amplification capability, for example using PCR methods. Some of the same features of native nucleic acid sequence that make them difficult to express in heterologous hosts may also make them difficult to clone or amplify. High secondary structure in one or more regions of the nucleic acid can make cloning or PCR difficult or impossible to perform on the intact nucleic acid or even on segments of the nucleic acid. However, using the methods of the invention to reduce the secondary structure, the resulting nucleic acid templates have better properties for polymerization and amplification. Making synthetic nucleic acids that amplify easily has important ramifications for common molecular biology procedures such as site directed mutagenesis. For example, using the methods of the invention, a nucleic acid sequence encoding a particular protein (a native protein, a protein with one or more desired mutations, or a completely artificial protein) can be designed using codons used more commonly in a desired expression host cell, and the predicted $\Delta G_{folding}$ may then optimized as described herein. Regardless of the features of the polymerase, or any particular weaknesses it may have (e.g., poor processivity), the probability of accurate full length synthesis of the copy strand from the template is improved using the synthetic nucleic acid of the invention because the regions of secondary structure have been reduced. Codons are replaced overall to minimize $\Delta G_{folding}$ in kcal/(mole) (base), but in specific locations also to alter the amino acid sequence encoded by the nucleotide sequence, resulting in a nucleic acid sequence encoding a particular protein with improved amplification and expression properties.

In one embodiment of this invention, the design and preparation of synthetic genes are used in application of directed evolution, gene shuffling and molecular breeding methods. Examples of gene shuffling and molecular breeding are described in U.S. Pat. No. 5,605,793, U.S. Pat. No. 5,811,238, U.S. Pat. No. 5,830,721, U.S. Pat. No. 5,837,458, U.S. Pat. No. 5,965,408, U.S. Pat. No. 5,958,672, U.S. Pat. No. 6,001,574, all herein incorporated by reference. Genes to be shuffled or recombined are designed and/or physically created based on the incorporation of preferred codons as described in the present invention. Such synthetic genes can also be created with greater homology, improving the reassembly of fragments in gene reassembly and shuffling methods. The advantage of the use of genes designed and physically created as described herein is the improved formation and expression of the shuffled or recombined genes. Such improved expression facilitates screening by providing higher levels of the gene products that are to be detected. The time required for screening can be reduced, or certain enzymatic activities can be detected more easily. Improvements in gene products, whether enzymes or metabolites produced by the actions of two or more different proteins derived through molecular breeding or directed evolution methods, can be detected more readily. Genes designed and produced according to the methods of the present invention can also be incorporated into kits for screening or other purposes. An example of an enzyme screening kit is found in U.S. Pat. No. 6,004,788, herein incorporated by reference.

Another embodiment of the invention, illustrated in the examples below, involves an improved method of synthesizing a nucleic acid. Usual methods of synthesizing a desired nucleic acid sequence which is not found in nature involves difficult and expensive chemical synthesis. The synthesis method of the invention to create a synthetic sequence involves an amplification method, such as PCR, using synthesized oligonucleotides designed to be overlapping, having as many adjacent sense and antisense strands as desired or required to complete the synthetic gene of choice. The oligonucleotides serve as both the template and primer in this PCR-based synthesis strategy.

The examples described herein demonstrate one implementation of the method for the physical creation of a synthetic gene. Two rounds of PCR reactions were carried out on three segments of the synmdeA gene, and six oligonucleotides per segment were used to construct the synthetic gene. The segments were ligated, amplified, excised, and inserted into an expression vector. The first round of amplification involved creating four long oligonucleotides (around 100 bps) based on the synthetic sequence. These long oligonucleotides were used to generate template DNA for various segments of the sequence. Longer synthetic sequences are best broken into shorter segments in this method for easier amplification. The first round PCR amplification relies on overlapping sections of each long oligonucleotide, to create areas of overlap. The areas of overlap serve to prime the extension of the neighboring segment. The areas of overlap can be any length that is sufficient for specificity and long enough for polymerase recognition/attachment, preferably at least 10 bases and more preferably at least 15 bases of overlap.

The second round of amplification used two short oligonucleotides (each about 30 nucleotides) to amplify the full-length segments. The short oligonucleotides overlap the 5' ends of the sense and antisense strands from the previous round to form a template of each segment primed by the first round strands, resulting in the filling in of both 5' and 3' ends after the second round of PCR. The segments derived from this two-round PCR are ligated together to form the unitary synthetic sequence. Preferably, this is facilitated using naturally occurring or synthesized restriction sites. Such sites enhance unidirectional cloning, ligation, etc.

It is understood that any nucleic acid and any reaction conditions that do not require exactly this sort of overlap and/or priming (e.g., RNA, RNA polymerases) can be used to create a modified nucleic acid of the invention without departing from the scope of the invention, and that other means of synthesizing the desired gene of interest are possible using methods known in the art. It is further understood that the gene or nucleic acid can be synthesized in one or several pieces. Likewise, many vectors and host species and strains other than those used herein can be used successfully in the practice of the invention.

The invention is described more fully in the following Examples, which are presented for illustrative purposes only and are not intended to limit the scope of the invention. In the embodiment of the invention disclosed by the Examples, a synthetic gene was designed which encodes the enzyme methionine gamma-lyase. Methods and vectors for its cloning and expression are provided, although other methods/vectors can be used.

EXAMPLE 1

Design of a Synthetic Gene Sequence

In these Examples, a specific synthetic gene sequence is disclosed encoding naturally occurring *P. putida* methionine gamma-lyase gene sequence, and consists of codons common to enteric bacteria such as *E. coli*. Also described are three gene fragments derived from the complete synthetic methionine gamma-lyase gene that have unique cloning sites at each end of each fragment.

Materials:

DNA taq polymerase and T4 DNA ligase were purchased from Roche (Branchburg, N.J.). Restriction endonucleases were purchased from New England Biolabs. Any suitable expression vector, such as pET15b expression vector and *E. coli* BL21(DE3), available from Novagen Madison, Wis.), may be used to express the synthetic sequences. pBAD expression vector and *E. coli* LMG 194 were purchased from Invitrogen (Carlsbad, Calif.). pGEM-3Z, pGEM-5Zf (+) cloning vectors and *E. coli* JM109 were purchased from Promega (Madison, Wis.). The oligonucleotides for PCR amplification were synthesized by IDT Inc. (Coralville, Iowa). QIAquick gel extraction kit and QIAprep spin miniprep kit were purchased from QIAGEN, Inc. (Valencia, Calif.).

Equipment:
Thermocycler Perkin Elmer model 9600 (1991).
Centrifuge
Water bath incubator
Culture incubator
Electrophoresis devices Software:
mfold—Prediction of RNA secondary structure by free energy minimization; Versions 2.0 and 3.0: suboptimal folding with temperature dependence. Michael Zuker and John Jaeger; Macintosh version developed by Don Gilbert DNA strider 1.01—a C program for DNA and protein sequence analysis designed and written by Christian Marck, Service de Biochime-Departement de Biologie, Institut de Recherche Fondamentale Commissariat a l' Energie Atomique-France HyperPCR—a Hypercard v. 20 stack to determine the optimal annealing temperature for PCR reaction and complementarity between the 3' ends of the two oligos and for internal complementarity of each 3' end. Developed by Brian Osborne, Plant Gene Expression Center, 800 Buchanan St., Albany, Calif. 94710

Amplify 1.2—for analyzing PCR experiments. Bill Engels 1992, University of Wisconsin, Genetics, Madison, Wis. 53706, WREngels@macc.wisc.edu Lasergene 99—a complete DNA sequence analysis system. DNASTAR, Inc., 1228 South Park St., Madison, Wis. 53715.

Design of Synthetic DNA Sequence Encoding *Pseudomonas putida* Methionine Gamma-Lyase.

The DNA sequence of naturally occurring mdeA gene was obtained from Entrez nucleotide Query (NID g2217943) (SEQ ID. NO. 1). Based on this DNA sequence and the amino acid sequence deduced from its open reading frame, several of the original codons were changed to codons that are more commonly used in enteric bacteria. The resulting designed sequence is shown in FIG. 1A (SEQ ID NO. 2). After changing codons to those more commonly used in *E. coli*, the computer program mfold was run to calculate the predicted $\Delta G_{folding}$ the sequence. The computer program was then used to generate an image of the predicted oligonucleotide, and regions of predicted secondary structure were identified. Codons in regions of high secondary structure were changed to the second most commonly used codon for that amino acid in *E coli*, and the predicted $\Delta G_{folding}$ the sequence was recalculated.

In addition, the sequence was modified to incorporate a non-naturally occurring glycine at amino acid position 2. The synthetic sequence therefore does not encode a protein identical to the naturally occurring polypeptide encoded by the *P. putida* methionine gamma-lyase gene. The modification of the sequence was incorporated to facilitate unidirectional cloning of the synthetic sequence into the cloning and expression vectors using an Nco I restriction site. The modified DNA sequence was termed synmdeA (SEQ ID NO. 2). In this Example, approximately fifty percent of the codons were changed from those found in the naturally-occurring gene.

EXAMPLE 2

Amplification of the Synthetic DNA Fragments mdeA1, mdeA2, mdeA3

Oligonucleotide Design:

Oligonucleotide primers were synthesized on the basis of the nucleic sequence of the synmdeA gene, whose sequence was determined from the process described in Example 1. The synmdeA gene, with 1200 bps of coding sequence (1207 bps with residual bases from restriction sites included) (SEQ ID NO. 3), was broken down into three fragments, mdeA1, mdeA2, and mdeA3. The first cloning fragment, mdeA1, contained a Nco I cloning site at the 5' end and a Pst I cloning site at the 3' end, and was 426 bps after the double stranded product was digested (SEQ ID NO. 4), 441 bps after second round amplification but before digestion (FIG. 1B; SEQ ID NO. 5). The second cloning fragment, mdeA2, contained a Pst I cloning site at the 5' end and an EcoRI cloning site at the 3' end, and was 410 bps after digestion (SEQ ID NO. 6), 430 bps after second round amplification but before digestion (FIG. 1C; SEQ ID NO. 7). The third one, mdeA3, contained an EcoR I cloning site at the 5' end and a BamH I cloning site at the 3' end, and was 366 bps after digestion (SEQ ID NO. 8), 383 bps after second round amplification but before digestion (FIG. 1D; SEQ ID NO. 9). The segments were the product of internal restriction sites occurring in the synmdeA sequence. Restriction sites were chosen that roughly divided the sequence into three equal segments, and which correspond to common multiple cloning sites on commercially available vectors.

To synthesize the segments, or fragments, four long oligonucleotides (98–117 bps), and two short oligonucleotides (~30 bps) were designed for each fragment, and with the help of computer software, their self-folding secondary structures were minimized as much as possible in order to maximize the DNA synthesis during PCR reactions. All the oligonucleotides had secondary structure $\Delta G$'s less negative than the $\Delta G$'s of the two overlapping annealed fragments, decreasing the probability of secondary structure forming instead of oligonucleotide hybridization.

Two short oligonucleotides and four long oligonucleotides were designed for each of the three segments. They were designed to have 17 to 18 bps overlap with each other. Underlined nucleotides indicate the annealing regions between two adjacent oligonucleotides.

1. First Segment of synmdeA: mdeA1

The sequences of these oligonucleotides was as follows:

```
mdePr1-1 (33 bps):   5' CAA GAG GCC ATG GGT CAC GGC TCC AAC AAA CTG 3' (sense)         (SEQ ID NO. 10)

mdePr1-2 (114 bps):  5' CAC GGC TCC AAC AAA CTG CCG GGC TTT GCT ACC CGC             (SEQ ID NO. 11)
                     GCT ATC CAC CAC GGT TAT GAC CCG CAG GAT CAC GGT GGT GCA CTG
                     GTT CCG CCG GTT TAC CAG ACT GCT ACT TTC ACC 3' (sense)
```

```
mdePr1-3 (116 bps):   5' GC TTC CAG CAG GTT GAG GGT CGG GTT GGA GAT ACG          (SEQ ID. NO. 12)
                      GGA GTA GAA GTG ACC AGC CTG TTC GCC AGC AAA GCA CGC AGC GCC
                      GTA TTC AAC GGT CGG GAA GGT GAA AGT AGC AGT GTG 3' (antisense)

mdePr1-4 (117 bps):   5' CTG AAC CTG CTG GAA GCA CGT ATG GCA TCT CTG AA          (SEQ ID NO. 13)
                      GGC GGC GAA GCT GGT CTG GCG GTG GCA TCT GGT ATG GGC GCG ATC
                      ACC TCT ACC CTG TGG ACC CTG CTG CGT CCG GGT GAC 3' (sense)

mdePr1-5 (116 bps):   5' GC CAT ATC TAC GTG ACG CAG TTT AAC GCC GAA TTC ACC      (SEQ ID NO. 14)
                      GAT ACC GTG GTG CAG GAA AGC AAA AGT ACA ACC ATA CAG GGT GTT
                      GCC CAG CAG AAC TTC GTC ACC CGG ACG CAG CAG 3' (antisense)

mdePr1-6 (33 bps):    5' CAG TGC CTG CAG CTG AGC CAT ATC TAC GTG ACG 3' (antisense)  (SEQ ID NO. 15)
```

2. Second Segment, mdeA2
The sequences of these oligonucleotides was as follows:

```
mdePr2-1 (33 bps):    5' GCT GAC CTG GAG GCA CTG GAA GCG GCT ATG ACC 3' (sense)   (SEQ ID NO. 16)

mdePr2-2 (114 bps):   5' CTG GAG GCT GCT ATG ACC CCG GCT ACC CGT GTT ATC         (SEQ ID NO. 17)
                      TAC TTC GAA TCC CCG GCT AAC CCG AAC ATG CAC ATG GCT GAC ATC
                      GCA GGT GTT GCT AAA ATC GCT CGT AAG CAC GGC 3' (sense)

mdePr2-3 (115 bps):   5' G GTA TTT AGT AGC GGA GTG AAC AAC CAG GTC AGC GCC       (SEQ ID NO. 18)
                      CAG TTC CAG CGG ACG TTG CAG GTA CGG AGT ACA GTA GGT GTT ATC
                      AAC AAC TAC GGT AGC GCC GTG CTT ACG AGC GAT 3' (antisense)

mdePr2-4 (111 bps):   5' CAC TCC GCT ACT AAA TAC CTG TCC GGC CAC GGC GAC        (SEQ ID NO. 19)
                      ATC ACT GCT GGC ATC GTA GTA GGC TCC CAG GCA CTG GTT GAC CGT
                      ATC CGT CTG CAA GGT CTG AAA GAC ATG ACC 3' (sense)

mdePr2-5 (115):       5' G TAC CTG AGC GTT AGC ACA GTG ACG GTC CAT ACG CAG GTT   (SEQ ID NO. 20)
                      CAG GGT CTT GAT ACC ACG CAT CAG CAG TGC TGC GTC GTG CGG GGA
                      CAG AAC AGC GCC GGT CAT GTC TTT CAG ACC 3' (antisense)

mdePr2-6 (33):        5' C CAG GAA TTC AGC CAG TAC CTG AGC GTT AGC AC 3' (antisense)  (SEQ ID NO. 21)
```

3. Third Segment, mdeA3
The sequences of these oligonucleotides was as follows:

```
mdePr3-1 (31 bps):    5' T CTT AAT GAA TTC CTG GCT CGT CAG CCG CAG 3' (sense)    (SEQ ID NO. 22)

mdePr3-2 (105 bps):   5' CTG GCT CGT CAG CCG CAG GTA GAA CTG ATC CAC TAT         (SEQ ID NO. 23)
                      CCG GGC CTG GCT TCC TTC CCG CAG TAC ACT CTG GCA CGT CAG CAG
                      ATG TCC CAG CCG GGC GGT ATG ATC 3' (sense)

mdePr3-3 (106 bps):   5' C GTC ACC CAG GGA AAC CGC ACG GGA GAA CAG CTG CAG       (SEQ ID NO. 24)
                      AGC GTT CAT GAA ACG ACG ACC AGC GCC GAT GCC ACC CTT CAG TTC
                      GAA AGC GAT CAT GCC ACC CGG CTG 3' (antisense)

mdePr3-4 (106 bps)    5' GCG GTT TCC CTG GGT GAC GCT GAA TCC CTG GCG CAG        (SEQ ID NO. 25)
                      CAC CCG GCA TCC ATG ACT CAC TCC TCC TAC ACT CCG GAA GAA CGT
                      GCG CAC TAC GGC ATC TCC GAA GGC C 3' (sense)

mdePr3-5 (98 bps):    5' CA AGC GCT AGC CTT CAG AGC CTG CTG AAC GTC TGC CAG      (SEQ ID NO. 26)
                      CAG ATC ATC GAT GTC TTC CAG ACC AAC AGA CAG ACG AAC CAG GCC
                      TTC GGA GAT GCC GTA 3' (antisense)

mdePr3-6 (32 bps):    5' T GGT GGA TCC TCA AGC GCT AGC CTT CAG AGC C 3' (antisense)  (SEQ ID NO. 27)
```

Amplification of Segmental DNA: mdeA1, mdeA2, mdeA3:

Each segment synthesis took two rounds of amplification. The first round was to generate the template for the second round using the four long oligonucleotides with overlapping ends (e.g., 3' or 5' sense ends overlapping neighboring 5' or 3' antisense ends). The second round amplification was using the two short nucleotides and the template from the first. Standard PCR reaction mixture was used with 100 µl reaction volume, 0.2 mM dNTPs (final concentration), and 60 to 90 pmoles of each oligonucleotide.

To synthesize the template for mdeA1, termed tpA1, mdePr1-2 (71 pmoles), mdePr1-3 (74 pmoles), mdePr1-4 (77 pmoles), and mdePr1-5 (64 pmoles) were used. MdePr2-2 (64 pmoles), mdePr2-3 (73 pmoles), mdePr2-4 (67 pmoles), and mdePr2-5 (74 pmoles) were used to synthesize mdeA2 template, termed tpA2. To synthesize mdeA3 template, termed tpA3, mdePr3-2 (66 pmoles), mdePr3-3 (62.6 pmoles), mdePr3-4 (60 pmoles), and mdePr3-5 (82 pmoles) were used. The strategy is shown in FIG. 2A. Based on the estimated annealing temperatures between the oligonucleotides above, the PCR reaction conditions were as follows: first denaturation at 94° C. for 2 min; then 10 cycles of denaturation at 94° C. for 30 sec; annealing at 51° C. for 40 sec, and extension at 72° C. for 1 min. This was followed by 20 cycles of denaturation at 94° C. for 30 sec; 65° C. for 55 sec; 72° C. for 1 min; then a final extension at 72° C. for 7 min. The PCR was carried out using a Perkin-Elmer Gene Amp 9600.

The PCR products were separated on 2% agarose gels run with a 1 kb DNA ladder (NEB); product bands of the expected size (411 bps for tpA1, 401 bps for tpA2, and 360 bps for tpA3) were cut out and extracted using QIAquick gel extraction kit. The products were then used as the templates for second round PCR reactions to synthesize mdeA1, mdeA2, and mdeA3 DNAs. The strategy for the second round amplification is shown in FIG. 2B.

For the second round, mdePr1-1 (80 pmoles), mdePr1-6 (67 pmoles), and 1 μl of 50 μl gel purified template tpA1 (above) were used to amplify the mdeA1 segment, again with the 3' end of mdePr1-1 and mdePr1-6 overlapping the 5' end of the template, and each 3' end (of oligonucleotide or template) priming the extension of the full length segment product. Similarly, mdePr2-1 (86 pmoles), mdePr2-6 (86 pmoles), and 1 μl template tpA2; mdePr3-1 (74 pmoles), mdePr3-6 (84 pmoles), and 1 μl tpA3 were used to amplify mdeA2 and mdeA3 segment respectively. The PCR reaction conditions were as follows: first denaturation at 94° C. for 2 min; then 25 cycles of denaturation at 94° C. for 30 sec, annealing at 51° C. for 40 sec, and extension at 72° C. for 30 sec; followed by a final extension at 72° C. for 7 min.

The PCR-amplified products were identified by size on the 2% agarose gel, a 441 bp-band for mdeA1, a 430 bp-band for mdeA2, and a 383 bp-band for mdeA3. The DNAs from the bands were extracted by using QIAquick gel extraction kit.

EXAMPLE 3

Cloning the Synthetic DNA Fragments mdeA1, mdeA2, and mdeA3 into an Appropriate Vector The vector pGEM-5Z (Promega, 3003 bps), and the purified PCR mdeA1 DNA were double cut with Nco I and Pst I; pGEM-3Z (Promega, 2743 bps), and the purified PCR mdeA2 DNA were double cut with Pst I and EcoR I restriction enzymes; pGEM-3Z and purified PCR mdeA3 DNA were double cut with EcoR I and BamH I restriction enzymes. These vectors carry the multiple cloning site arrangement from pUC18, and are ampicillin resistant. All restriction digestion reactions were incubated overnight at 37° C. The digested products were then purified by gel electrophoresis on a 2% agarose gel followed by extraction of the DNA using a QIAquick gel extraction kit.

Figure 3:
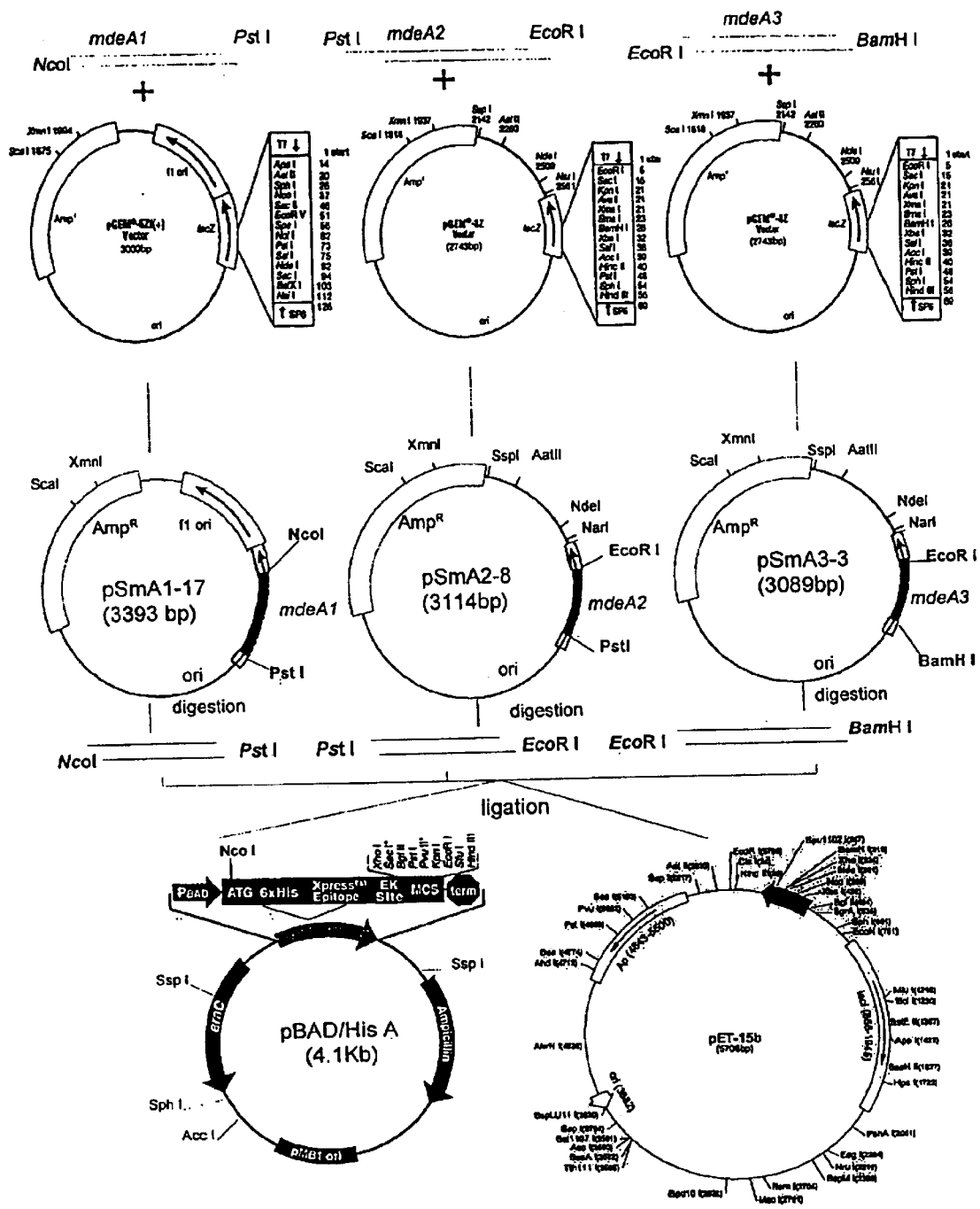
FIG. 3 is a schematic of the cloning strategy for mdeA1, mdeA2 and mdeA3 into cloning and expression vectors. The amplified segments are ligated into the multiple cloning site of the illustrated vector in the top row, then *E. coli* are transformed with the plasmids. Individual plasmids containing each segment are selected in the second row, and the plasmids are double-digested to extract the insert, which is then ligated into an expression vector as shown in the last row.

The purified, double cut pGEM-5Z and mdeA1 were ligated with T4 DNA ligase and buffers (NEB) and incubated overnight at 16° C. Similarly, the double cut pGEM-3z and mdeA2, and double cut pGEM-3z and mdeA3, were ligated with T4 DNA ligase, but they were incubated at 12° C. because EcoR I site requires lower temperature to anneal. Several reactions were carried out for each construct to ensure optimization of molar ratios between vector and insert (e.g. 1:1, 1:3, and 3:1 vector:insert ratio). FIG. 3 illustrates the multiple cloning site and ligation of inserts into the vectors.

E. coli JM109 competent cells (Promega or Bio 101) were transformed with the ligation reactions described above using a standard heat shock transformation procedure (Sambrook et al., 1989, supra). To select for colonies containing mdeA1, mdeA2, and mdeA3 clones, the cells were grown on LB+Ampicillin (50 μg/μl) plates.

Transformant colonies were first tested with PCR screening using the mdePr1-1, mdePr1-6, mdePr2-1, mdePr2-6, mdePr3-1, and mdePr3-6 as the primers for mdeA1, mdeA2, and mdeA3 clones respectively. The PCR reaction volume was 25 μl with 0.2 mM dNTPs and 20 pmoles of each primers. The templates were picked directly from the colonies, and the conditions were as follows: first denaturation at 94° C. for 4 min; then 25 cycles of denaturation at 94° C. for 30 s; annealing at 57° C. for 40 s; and extension at 72° C. for 30 s; then a final extension at 72° C. for 7 min. The positive colonies containing mdeA1, mdeA2, or mdeA3 clones were identified by the presence of 441 bp, 430 bp, or 383 bp bands respectively.

To further confirm that the colony actually carried the mdeA1, mdeA2, or mdeA3 construct, restriction mapping of its plasmid was done by cutting the plasmid with Nco I+Pst I, Pst I+EcoR I, or EcoR I+BamH I. The presence of a 426 bp-band (mdeA1), a 414 bp-band (mdeA2), or a 367 bp-band (mdeA3) would be expected on 2% agarose gel if the plasmid carries the proper insert.

EXAMPLE 4

Sequencing of the Synthetic mdeA1, mdeA2 and mdeA3 DNA Fragments

After isolating plasmids containing the mdeA 1, mdeA2 and mdeA3 inserts, the clones were submitted to the UCLA sequencing facility (Los Angeles, Calif.) for sequencing. M13 forward and reverse primers were used. Clones that carried the correct DNA sequence of mdeA1, mdeA2, and mdeA3 were selected and named pSmA1-17, pSmA2-8, and pSmA3-3.

EXAMPLE 5

Construction of Full-Length synmdeA Encoding Methionine Gamma-Lyase

The colonies containing pSmA1-17, pSmA2-8, and pSmA3-3 were cultured with LB+ampicillin (50 μg/μl) overnight at 37° C. Plasmids were extracted using QIAprep spin miniprep kit (QIAGEN, Inc., Valencia, Calif.). The plasmids pSmA1-17, pSmA2-8, and pSmA3-3 were double cut overnight at 37° C. with Nco I/Pst I, Pst I/EcoR I, and EcoR I/BamH I restriction enzymes respectively. A pET15b vector (Novagen) was cut with Nco I/BamH I restriction enzymes, and a pBAD/His C vector (Invitrogen) was cut with Nco I/Bgl II. The double cut DNAs were separated on 2% agarose gel, and the bands corresponding to mdeA1 (426 bps), mdeA2 (414 bps), mdeA3 (367 bps), pET15b (5 k bps), and pBAD/His C (4 kbs) were isolated and purified using QIAquick gel extraction kit.

Purified mdeA1, mdeA2, and mdeA3 DNAs were then ligated into double cut pET15b at Nco I and BamH I, or pBAD/His C at Nco I and Bgl II cloning sites using T4 DNA ligase overnight at 12° C.

The resulting plasmids were transformed into E. coli JM109 competent cells using a standard heat shock transformation procedure (Sambrook et al., 1989, supra). To select the positive clones containing synmdeA, the cells were grown on LB+Ampicillin (50 μg/μl) plates overnight at 37° C.

The transformant colonies were first checked with the PCR screening method described above by using mdePr1-1 and mdePr3-6 as the primer probes. A 1200 bp-band was expected on the agarose gel if the colony contained synmdeA clones. Selected pET15b and pBAD/His C vectors carrying the synmdeA insert were named pTM-1 and pBM-1 overexpression plasmids, respectively. The PCR positive colonies were then further confirmed by using a restriction mapping method, with Nco I and BamH I restriction enzymes used on pTM-1, and Nco I and Hind III restriction enzymes used on pBM-1. Again, 1200 bp-bands were seen on 2% agarose gels.

Plasmids pTM-1 and pBM-1 were transferred to expression host E. coli BL21(DE3) and LMG 194 by first plasmid extraction, followed by transformation.

EXAMPLE 6

Over-Expression of Synthetic L-Methionine-Alpha-Gamma-Lyase Gene

Host E. coli strains carrying pTM-1 and pBM-1, referred to as BL/pTM01 and LMG/pBM01 respectively, were grown on LB+ampicillin plate and RMG+ampicillin plate respectively. A single colony from each plate was then picked and cultured overnight in LB+ampicillin liquid medium. Then 5 ml of LB+ampicillin was inoculated with 100 μl of each overnight culture, and each was incubated for 2 hours at 37° C. with shaking or until O.D.$_{600}$ (nm) reached 0.8–0.9. Initially, 1 ml of each culture was removed as a non-induced control. BL/pTM01 culture was then induced to express protein by adding IPTG to a final concentration of 2 mM, and LMG/pBM01 culture was induced with a final concentration of 0.02% L-arabinose. Incubation was continued at 37° C. for 3 hours. Samples of 1 ml were collected every hour. All samples were centrifuged at 12,000× g for 3 minutes. The cells were then lysed by resuspension in 1× NuPAGE sample buffer (Novex) containing 50 mM DTT, and incubation at 97° C. for 3 minutes. After centrifugation for 10 min at 12,000× g, the supernatants were separated along with protein size markers by SDS-page on 4%–20% gradient polyacrylamide gel (NuPAGE MES SDS, Novex) for 1 hour at 150 volts. The gels were stained by Coomassie blue for 2 hours and destained in 10% acetic acid, 20% methanol solution, followed by destaining in 7% acetic acid, 5% methanol. 43 kD bands corresponding to a molecular weight marker were seen on the destained gels (FIG. 4). These bands corresponded to the major protein in the induced samples. As seen in FIG. 4, expression of synmdeA was vastly superior to expression of the native enzyme, seen in FIG. 5. The native enzyme expressed poorly in E. coli, and was a truncated portion of the complete gene. Attempted expression of the native gene gave a protein of apparent molecular weight approximately 28 kD, indicating that a substantial part of the enzyme was missing. The protein showed no methionine gamma-lyase activity. Without wishing to be bound to any particular mechanism, it is hypothesized that the truncation was caused by an interruption in translation at a rare codon. This speculation is supported by the fact that an interruption at this point would result in a polypeptide product having a molecular weight of approximately 28 kD.

EXAMPLE 7

Comparison of Native mdeA and synmdeA Gene Expression

To demonstrate the usefulness of the synthetic gene for the expression of difficult to express genes in E. coli, the synmdeA gene was expressed in E coli using the vector pET15b. This gene encodes a methionine β lyase enzyme, but contains an additional amino acid relative to the native protein described by Soda and co-workers (e.g., U.S. Pat. No. 5,863,788). The results are shown in the gel in FIG. 4A.

Based on the density of the band corresponding to the methionine-gamma lyase enzyme of approximate molecular weight 40,000 we estimate the level of expression to be 10% or more of the total protein in the crude cell lysate of the E. coli host. By contrast, expression of the native mdeA gene in the vector pSIT is substantially less under the same induction conditions (FIG. 4B). In the experiment shown in FIG. 4B, all samples were incubated at 37° C. The induced samples contain extra bands of about 28 kD which indicate that premature termination of the enzyme occurred during translation of the native gene. Both the native and synthetic gene vectors are under the control of T7 RNA polymerase promoters.

To put these results into another context, the expression reported by Soda and coworkers in U.S. Pat. Nos. 5,861,154 and 5,863,788 is reported to be 0.82 units/mg. Using the specific activity of the purified enzyme of 20.4 units/mg reported by Soda in Anal Biochime. 138, 421–424 (1984), the expression level is estimated to be no more than 4% of the total protein in the E. coli host. This estimate is an upper limit on the expression reported by Soda because the reported activity involves some partial purification of the enzyme prior to assay.

EXAMPLE 8

Comparison of Expression of Genes with Different $\Delta G_{folding}$

FIG. 5 is a gel showing expression of two genes with different $\Delta G_{folding}$. Naphthalene Dioxygenase from P. putida has a $\Delta G_{folding}$ of −256.1 kcal/mol. This very low free energy would not be expected, under the principles of the invention, to express well. In fact, as seen in lanes 1–4 of FIG. 5, it does not. By contrast, another gene, methionine gamma lyase (mgl 1) from T. vaginalis has a $\Delta G_{folding}$ of −152.5 kcal/mol. As can be seen from lanes 6–9 of FIG. 5, this protein can be induced and expresses well under the conditions used. Both genes were cloned into the pBAD vector and grown at 37° C.

EXAMPLE 9

Synthesis of Improved Eukaryotic Genes and Their Expression in Prokaryotic Hosts Oxidoreductases The enzyme family of oxidoreductases is large and complex, and many members function to stereoselectively oxidize and reduce functional groups such as C=O, C=C, and C=N. In pharmaceutical and agricultural industries, for example, these enzymes are used to prepare drugs and chemicals requiring e.g., chiral compounds. For example, they can be used to stereoselectively reduce ketones to produce chiral alcohols consisting predominantly of a single stereoisomer. In this Example, the methods of the invention were used to create highly expressible oxidoreductases. Properties of exemplary original oxidoreductase genes and their synthetic analogs are discussed and shown in Table 3 below, and the superiority of the synthetic sequences in ΔG, expression, and enzyme activity can be seen.

Keto Reductases

These enzymes reduce keto esters, aldehydes, and other ketones into equivalent alcohol products.

NADPH-Dependent Aldehyde Reductase 1, ALR1: The native gene encoding a NADPH-dependent aldehyde reductase (ALR) is from a red yeast, Sporobolomyces salmonicolor (also known as Sporidiobolus salmonicolor), and catalyzes the reduction of a variety of carbonyl compounds.

The gene is 969 bp (SEQ ID NO. 31) and encodes a polypeptide of 35,232 Da. The deduced amino acid sequence (SEQ ID NO. 32) shows a high degree of similarity to other members of the aldo-keto reductase superfamily. The synthetic aldehyde reductase 1 gene (synALR1; SEQ ID No. 33) was created using the known protein sequence.

Aldehyde Reductase 2. ALR2: This gene, encoding an NADPH-dependent aldehyde reductase (AR2) in *Sporobolomyces salmonicolor* AKU4429, reduces ethyl 4-chloro-3-oxobutanoate (4-COBE) to ethyl (S)-4-chloro-3-hydroxybutanoate (Kita et al., *Appl Environ Microbiol* 1999 Dec; 65(12):5207–11). The ALR2 gene (SEQ ID NO. 34) is 1,032 bp long and encodes a 37,315-Da polypeptide. The deduced amino acid sequence (SEQ ID NO. 35) exhibits significant levels of similarity to the amino acid sequences of members of the mammalian 3-beta-hydroxysteroid dehydrogenase-plant dihydroflavonol 4-reductase superfamily but not to the amino acid sequences of members of the aldo-keto reductase superfamily or to the amino acid sequence of an aldehyde reductase previously isolated from the same organism (K. Kita, et al.,*Appl. Environ. Microbiol.* 62:2303–2310, 1996; SEQ ID NO. 32). The synthetic version of ALR2, or synALR2mut (SEQ ID NO. 36) contains a mutation at position 25 of the amino acid sequence (SEQ ID NO. 37), replacing alanine with glycine to introduce a mutation that allows the enzyme to use both NADH and NADPH as a cofactor.

Reductase 1 from yeast, YPR1: This enzyme is a good general ketone reductase. The "native" sequence, related to Accession No. X80642 (Miosga et al.), was cloned into pBAD with a GGT insertion after the initiating ATG (SEQ ID NO. 38). This addition resulted in a glycine at position 2 in the amino acid sequence in both the "native" and the synthetic YPR1 peptide sequence (SEQ ID NO. 39) to add a restriction site for ease of cloning. SEQ ID NO. 40 is the synthetic sequence, having a 15.1% improvement in $\Delta G_{folding}$.

Yeast GCY1: SEQ ID NO. 41 is a nuclear gene for a yeast protein showing unexpectedly high homology with mammalian aldo/keto reductases as well as with p-crystallin, one of the prominent proteins of the frog eye lens. The coding region is 939 bases and encodes a protein of 312 amino acids (SEQ ID NO. 42; estimated MW 35,000). A synthetic analog was made, synGCY1 (SEQ ID NO. 43), having a GGC insertion after ATG (to facilitate cloning into the pBAD vector), which results in the insertion of a glycine after the initiating methionine in the synthetic peptide sequence (SEQ ID NO. 44).

Reductase Gre2 from yeast: This gene and related protein product were originally sequenced as part of the yeast genome (Goffeau et al., Accession Nos. NC_001147 and NP_014490). The native gene (SEQ ID NO. 45) was not cloned, and its protein sequence (SEQ ID NO. 46) is based on the best open reading frame. However, the synthetic gene synGRE2 (SEQ ID NO. 47) derived from the wild-type sequence was modified by addition of a GGC insertion (to add a restriction site), cloned, and expressed as a protein (SEQ ID NO. 48). The protein's reductase function has been confirmed.

Yeast Aldo-Keto Reductase Gre3: This gene and related protein encode a keto-aldose reductase (Goffeau et al., Accession Nos. NC_001140 and NP_011972). The "native" sequence (SEQ ID NO. 49) has been modified to insert an ATT at the second codon position (inserting isoleucine in SEQ ID NO. 50) to add a restriction site for cloning. The "native" Gre3 protein exhibits reductase activity at 30° C. and 37° C. as shown in Table 3 below.

CMKR (S1): The product of this gene (SEQ ID NO. 69) is an NADPH-dependent carbonyl reductase (S1) from *Candida magnoliae*, which catalyzes the reduction of ethyl 4-chloro-3-oxobutanoate (COBE) to ethyl (S)-4-chloro-3-hydroxybutanoate (CHBE), with a 100% enantiomeric excess. This is a useful chiral building block for the synthesis of pharmaceuticals. The S1 gene is 849 bp and encodes a polypeptide of 30,420 Da. The deduced amino acid sequence (SEQ ID NO. 70) has a high degree of similarity to those of other members of the short-chain alcohol dehydrogenase superfamily.

TABLE 3

Properties of Native and Synthetic Genes

| Gene name | length (bps) | Molecular Weight (kD) | $\Delta G$ (kcal/mole) | $\Delta G$/base (kcal/mole · base) | % $\Delta G$ difference between native and synthetic | Activity at 30° C. (u/ml) | Activity at 37° C. (u/ml) |
|---|---|---|---|---|---|---|---|
| nativeALR1 | 972 | 35.2 | −152.5 | −0.157 | 100 | ND | ND |
| synALR1 | 972 | 35.2 | −85.8 | −0.0883 | 56.3 | 75.5 | 9.25 |
| nativeALR2 | 1032 | 37.3 | −162.2 | −0.1572 | 100 | ND | ND |
| synALR2mut | 1032 | 37.3 | −101.2 | −0.0981 | 62.4 | 4.13 | 7.0 |
| nativeYPR1 | 942 | 34.8 | −89.4 | −0.0949 | 100 | 4.15 | 6.23 |
| synYPR1 | 942 | 34.8 | −75.9 | −0.0806 | 84.9 | 11.791 | 16.609 |
| nativeGCY1 | 939 | 35.1 | −76.6 | −0.0816 | 100 | 0.105 | 0.533 |
| synGCY1 | 942 | 35.1 | −73.2 | −0.0777 | 95.2 | 4.00 | 4.53 |
| nativeGRe2 | 1029 | 38.2 | −103.3 | −0.1004 | 100 | ND | ND |
| synGRE2 | 1032 | 38.2 | −71.6 | −0.0694 | 69.1 | ND | ND |
| nativeGRE3 | 987 | 37.2 | −89 | −0.0902 | 100 | 0.35 | 0.52 |
| synGRE3 | 987 | 37.2 | −65.5 | −0.0664 | 73.6 | 1.2 | 1.1 |
| native CMKR | 852 | 30.6 | −145.4 | −0.1706 | 100 | ND | ND |
| synCMKR | 852 | 30.6 | −70.5 | −0.0827 | 48.5 | ND | 239.16 |
| pKDDC | 1461 | 54.0 | −244.4 | −0.1673 | 100 | ND | ND |
| synAAAD | 1464 | 54.0 | −133.9 | −0.0915 | 54.7 | ND | ND |
| Fdh1.2 | 1098 | 40.6 | −76.1 | −0.0693 | 100 | 0.48 | 0.54 |
| synFdh | 1098 | 40.6 | −98 | −0.0893 | 128.9 | 2.48 | 0.19 |

ND = not determined.

Other Sequences

L-Aromatic Amino Acid Decarboxylase from Pig Kidney: L-Aromatic amino acid decarboxylase (dopa decarboxylase; DDC) is a pyridoxal 5'-phosphate (PLP)-dependent homodimeric enzyme that catalyzes the decarboxylation of L-dopa and other L-aromatic amino acids. A cDNA that codes for the protein from pig kidney was cloned by Moore et al., Biochem J 1996 Apr 1;315 (Pt 1):249–56. Using this pKDDC sequence (SEQ ID NO. 53; Accession No. S82290) and its deduced amino acid sequence (SEQ ID NO 54), a synthetic decarboxylase, synAAAD was constructed with a GGT insertion (SEQ ID NO 55) to insert a glycine in the amino acid sequence (SEQ ID NO. 56). The synAAAD nucleic acid sequence had a nearly 50% improvement in AG (see Table 3).

Formate Dehydrogenase (Fdh1.2): The formate dehydrogenase (Fdh1.2) DNA (SEQ ID NO. 57) and protein sequence (SEQ ID NO. 58) is from Candida boidinii (Accession No. AJ245934). In order to create a Nco I restriction site for cloning into expression vector pBAD/HisA, a glycine codon was inserted after the first methionine codon (SEQ ID NO. 59). The resultant recombinant protein, synFdh (SEQ ID NO. 60) has an inserted glycine after the initiating methionine as compared to the native protein. Native Fdh1.2 and synFdh otherwise encode the same protein sequence. The synthetic sequence had 199 out of 366 codons changed as compared to native Fdh1.2 to optimize expression in E. coli (see Table 4 below). Homology at the DNA level of Fdh1.2 and synFdh is about 78.5%. Expression of synFdh is 5-fold higher based on activity measurements than expressed native Fdh1.2.

The $\Delta G$ of Fdh1.2 is $-76.1$ kcal/mole ($-0.069$ kcal/mol-base) and the $\Delta G$ of synFdh is $-98.0$ kcal/mole ($-0.089$ kcal/mol·base). Because native Fdh1.2 does not have high secondary structure, it was possible to optimize the sequence for expression according to methods of the invention without increasing, and in fact, slightly decreasing, the $\Delta G_{folding}$. FIG. 7 shows expression data of Fdh1.2 compared with synFdh at 30° C. and 37° C. As shown in FIG. 8, synFdh, induced with 0.2% L-arabinose at 30° C., exhibits higher catalytic activity than does induced native Fdh1.2 or uninduced Fdh1.2 in the oxidation of formate in the presence of $NAD^+$ ($NAD^+ + HCO_2^- \rightarrow NADH + CO_2$). These figures demonstrate the superior expression characteristics of the synthetic Fdh sequence as compared to the native sequence.

TABLE 4

Codon Preference of C. boidinii and E. coli for Selected Amino Acids

| Amino Acid | C. boidinii Codon | E. coli Codon |
|---|---|---|
| R (Arg) | AGA (13/13) | AGA (0); CGT (0.74) |
| N (Asn) | AAT (14/16) | AAT (0.06), AAC (0.94) |
| D (Asp) | GAT (22/24) | GAT (0.33), GAC (0.67) |
| Q (Gln) | CAA (9/9) | CAA (0.14), CAG (0.86) |
| L (Leu) | TTA (22/32) | TTA (0.02), CTG (0.83) |
| P (Pro) | CCA (11/14) | CCA (0.15), CCG (0.77) |
| T (Thr) | ACT (11/22) | ACT (0.35), ACC (0.55) |

Hydantoinase: The hydantoinase gene from Pseudomon asputida (SEQ ID NO. 61) and its deduced amino acid sequence (SEQ ID NO. 62) (Accession No. AAC00209) were used to create synthetic hydantoinase gene (SEQ ID NO. 63) and protein (SEQ ID NO. 64) products. This gene product is useful to make non-natural α-amino acids. To create the synthetic gene and protein, a glycine was added after the first methionine so that the gene could be subcloned into the pBAD/HisA expression vector. The nucleic acid sequence is 1491 bp, and in its native form has a free energy of folding of $-287.6$ kcal/mole. The synthetic hydantoinase has a $\Delta G$ of $-155.5$ kcal/mole. Homology at the nucleic acid level between the native and synthetic hydantoinase is 78.4%.

Vanillyl Alcohol Oxidase, VaoA: A vanillyl-alcohol oxidase gene (SEQ ID NO. 65) and its deduced amino acid sequence (SEQ ID NO. 66) from Penicillium simplicissimum was used. VaoA oxidizes vanillyl alcohol and related aromatic alcohols. To create the synthetic gene (SEQ ID NO. 67) and protein (SEQ ID NO. 68), a glycine was added after the first methionine so that the gene could be subcloned into the pBAD/HisA expression vector. The sequence is 1686 bp long and the native form has a $\Delta G$ of $-176.8$ kcal/mole; $\Delta G$ of synVaoA is $-164.6$ kcal/mole. The genes have 77% homology at the nucleic acid level.

Myo-Inositol-1-Phosphate Synthase (Ino1): INO-1 (SEQ. ID NO. 73) cyclizes D-glucose 6-phosphate to myo-inositol 1-phosphate, which is a precursor for coenzyme Q. The native ino-1 gene (SEQ. ID NO. 72) is 1602 bps. The $\Delta G$ is $-152.2$ kcal/mole. The synthetic ino-1 gene, called synIno-1 (SEQ. ID NO. 74) has a GGT insertion to create the cloning site, which inserts a glycine residue in the synINO protein (SEQ. ID NO. 75). synIno-1 is 1605 bps and has a $\Delta G$ of $-131.8$ kcal/mole. The similarity at DNA level of the ino 1 and synIno 1 is 77.4%.

Galactose Oxidase (GAO): The gaoA gene (SEQ. ID. NO. 76), encoding the secreted copper-containing enzyme galactose oxidase (SEQ. ID. NO. 77), was isolated from the Deuteromycete fungus Dactylium dendroides (Accession number: M86819; also called Hypomyces rosellus). $\Delta G$ for the native DNA is $-244$ kcal/mole and $\Delta G$ for the synthetic gene (synGAO, SEQ. ID. NO. 78) is $-195.3$ kcal/mole. The open reading frame for galactose oxidase (GAO) is 2046 bp. At the DNA level, synGAO and GAO have 76.6% identity. Glactose oxidase oxidizes galactose, and can be used in the quantitative determination of galactose level in blood. The synthetic galactose oxidase protein (SEQ. ID. NO. 79) has a glycine inserted in the second amino acid position.

The Gibbs free energy (AG) of all DNA foldings described in this Example were determined using mfold2 provided by Washington University School of Medicine (http://mfold2.wustl.edu). The conditions used for calculation of the free energy of DNA folding were 37° C., $Na^+ = 1M$ and $Mg^{++} = 0$.

Assays of enzyme activities of the keto reductases were determined photometrically using Ethyl 4-chloroacetoacetate as a substrate. The reaction mixture (1.0 ml) comprised 50 mM potassium phosphate buffer (pH 6.5), 250 M NADPH, 5 mM substrate, and cell lysate. The reaction was measured at room temperature. One unit of the enzyme was defined as the amount catalyzing the oxidation of 1 mole NADPH/min. Formate dehydrogenase activity was assayed by mixing sodium formate with NAD+, and measuring NADH recycling activity on a spectrophotometer at 340 nm.

As seen by the results generated in this example, the methods of the invention are widely applicable to unrelated genes from both prokaryotes and eukaryotes, and result in improved expression and enzymatic activity when expressed in a heterologous prokaryotic or eukaryotic host cell.

The preceding description has been presented with references to presently preferred embodiments of the invention. Persons skilled in the art and technology to which this invention pertains will appreciate that alterations and changes in the described genes, proteins, and methods can be practiced without meaningfully departing from the principle, spirit and scope of this invention.

Accordingly, the foregoing description should not be read as pertaining only to the precise genes, proteins, and methods described and shown in the accompanying drawings, but rather should be read as consistent with and as support for the following claims, which are to have their fullest and fairest scope.

What is claimed is:

1. A synthetic nucleic acid sequence comprising a non-naturally occurring polymer of nucleic acids that is at least 90% homologous to SEQ ID NO. 78 or its complementary sequence.

* * * * *